(12) United States Patent
Berezov et al.

(10) Patent No.: US 12,419,888 B2
(45) Date of Patent: Sep. 23, 2025

(54) METHODS OF TREATING ELEVATED PLASMA CHOLESTEROL

(71) Applicants: INSTITUT DE CARDIOLOGIE DE MONTREAL, Montréal (CA); Affina Biotechnologies, Inc., Valhalla, NY (US)

(72) Inventors: Alan Berezov, White Plains, NY (US); Alexander Vinitsky, New York, NY (US); Steve Poirier, Montréal (CA); Gaétan Mayer, Montréal (CA)

(73) Assignees: INSTITUT DE CARDIOLOGIE DE MONTREAL, Montréal (CA); AFFINA BIOTECHNOLOGIES, INC., Valhalla, NY (US)

( * ) Notice: Subject to any disclaimer, the term of this patent is extended or adjusted under 35 U.S.C. 154(b) by 0 days.

(21) Appl. No.: 17/547,704

(22) Filed: Dec. 10, 2021

(65) Prior Publication Data
US 2022/0296593 A1    Sep. 22, 2022

Related U.S. Application Data

(60) Provisional application No. 63/124,276, filed on Dec. 11, 2020.

(51) Int. Cl.
| | | |
|---|---|---|
| *A61K 31/502* | (2006.01) | |
| *A61K 31/192* | (2006.01) | |
| *A61K 31/216* | (2006.01) | |
| *A61K 31/22* | (2006.01) | |
| *A61K 31/366* | (2006.01) | |
| *A61K 31/395* | (2006.01) | |
| *A61K 31/397* | (2006.01) | |
| *A61K 31/40* | (2006.01) | |
| *A61K 31/405* | (2006.01) | |
| *A61K 31/437* | (2006.01) | |
| *A61K 31/454* | (2006.01) | |
| *A61K 31/4545* | (2006.01) | |
| *A61K 31/47* | (2006.01) | |
| *A61K 31/4709* | (2006.01) | |
| *A61K 31/505* | (2006.01) | |

(Continued)

(52) U.S. Cl.
CPC .......... *A61K 31/502* (2013.01); *A61K 31/192* (2013.01); *A61K 31/216* (2013.01); *A61K 31/22* (2013.01); *A61K 31/366* (2013.01); *A61K 31/395* (2013.01); *A61K 31/397* (2013.01); *A61K 31/40* (2013.01); *A61K 31/405* (2013.01); *A61K 31/437* (2013.01); *A61K 31/454* (2013.01); *A61K 31/4545* (2013.01); *A61K 31/47* (2013.01); *A61K 31/4709* (2013.01); *A61K 31/505* (2013.01); *A61K 31/519* (2013.01); *A61K 31/527* (2013.01); *A61K 31/55* (2013.01); *A61P 3/06* (2018.01); *C07D 401/06* (2013.01); *C07D 401/12* (2013.01); *C07D 401/14* (2013.01); *C07D 403/12* (2013.01); *C07D 417/14* (2013.01); *C07D 471/04* (2013.01); *C07D 471/10* (2013.01); *C07D 471/14* (2013.01); *C07D 487/04* (2013.01); *C07D 491/052* (2013.01)

(58) Field of Classification Search
CPC ......... A61P 3/06; A61K 31/395; A61K 31/40; A61K 31/4545; A61K 31/22; A61K 31/454; A61K 31/47; A61K 31/4709; A61K 31/519; A61K 31/527; A61K 31/444; A61K 45/06; A61K 31/502; A61K 31/192; A61K 31/216; A61K 31/366; A61K 31/397; A61K 31/405; A61K 31/437; A61K 31/505; A61K 31/55; C07D 401/06; C07D 401/12; C07D 401/14; C07D 403/12; C07D 417/14; C07D 471/04; C07D 471/10; C07D 471/14; C07D 487/04; C07D 491/052; C07D 403/14; C07D 405/14; C07D 409/14; C07D 413/14; C07D 487/14; C07D 491/107
See application file for complete search history.

(56) References Cited

U.S. PATENT DOCUMENTS 6,492,358 B2 * 12/2002 Sui ...................... C07D 495/04
                                                          546/85
2008/0004261 A1    1/2008  Gutierrez et al.
(Continued)

FOREIGN PATENT DOCUMENTS

JP    WO 2013/137371 A1 *  9/2013  ........... C07D 239/42
JP    2017-105765 A          6/2017
(Continued)

OTHER PUBLICATIONS

Gibbons, G.F. The Role of Cytochrome P450 in the Regulation of Cholesterol Biosynthesis, Lipids, 2002, vol. 37(12); 1163-1170 (Year: 2002).*

(Continued)

*Primary Examiner* — Amy L Clark
*Assistant Examiner* — Chihyi Lee
(74) *Attorney, Agent, or Firm* — Clark & Elbing LLP

(57) ABSTRACT

The present invention relates to compounds of Table 1, which are encompassed by Formula I and/or Formula II, III, IV, V, or VI, and pharmaceutically acceptable salts, solvates or compositions thereof. Compounds of Table 1 are PCSK9 interacting small molecules that modulate PCSK9 activity and significantly increase low density lipoprotein receptor expression and activity, lower total circulating cholesterol and are useful for treating and delaying the onset of diseases that are associated with elevated cholesterol.

5 Claims, 5 Drawing Sheets

(51) Int. Cl.
*A61K 31/519* (2006.01)
*A61K 31/527* (2006.01)
*A61K 31/55* (2006.01)
*A61P 3/06* (2006.01)
*C07D 401/06* (2006.01)
*C07D 401/12* (2006.01)
*C07D 401/14* (2006.01)
*C07D 403/12* (2006.01)
*C07D 417/14* (2006.01)
*C07D 471/04* (2006.01)
*C07D 471/10* (2006.01)
*C07D 471/14* (2006.01)
*C07D 487/04* (2006.01)
*C07D 491/052* (2006.01)

(56) References Cited

U.S. PATENT DOCUMENTS

2009/0176769 A1 7/2009 Anderson et al.
2019/0134056 A1* 5/2019 Tolias .................. A61K 31/536

FOREIGN PATENT DOCUMENTS

| WO | WO-2009/072643 A1 | 6/2009 | |
|----|---|---|---|
| WO | WO-2011/002067 A1 | 1/2011 | |
| WO | WO-2011/084985 A1 | 7/2011 | |
| WO | WO-2011/147780 A1 | 12/2011 | |
| WO | WO 2013/137371 A1 * | 9/2013 | ........... C07D 239/42 |

OTHER PUBLICATIONS

Ahamad, S. et al. Development of small-molecule PCSK9 inhibitors for the treatment of hypercholesterolemia. Drug discovery today, 2022. vol. 27, No. 5:1332-1349. (Year: 2022).*
CAS Registry No. 374634-94-3 (Entered STN Registry on Dec. 10, 2001). (Year: 2001).*
Communication enclosing the Partial European Search Report for European Application No. 21213891.1, dated Aug. 26, 2022 (15 pages).
Extended European Search Report for European Patent Application No. 21213891.1, dated Dec. 9, 2022 (13 pages).

* cited by examiner

METHODS OF TREATING ELEVATED PLASMA CHOLESTEROL

FIELD OF THE INVENTION

The present invention is directed to compounds, pharmaceutically acceptable salts or solvates thereof, pharmaceutical compositions including one or more compounds of Formula I, methods of synthesizing or manufacturing one or more compounds of Formula I, and use of one or more compounds of Formula I as modulators of proprotein convertase subtilisin/kexin 9 and therefore low density lipoprotein receptor expression and activity. Compounds featured herein are useful for lowering total circulating cholesterol, and treating, reducing the symptoms of, delaying the onset of, reducing the likelihood of occurrence of, or delaying the progression of diseases that are associated with elevated cholesterol.

BACKGROUND OF THE INVENTION

The worldwide prevalence of atherosclerotic cardiovascular diseases (ASCVD) such as heart attacks and stroke is a major public health and economic burden that is still expected to increase in the next decades (Mackay et al., *World Health Organization.* 2004:112p; Heidenreich et al., *Circulation.* 2011; 123(8):933-944). Elevated circulating low-density lipoprotein cholesterol (LDL-cholesterol; LDLc) is positively correlated with premature development of ASCVD and death (Kannel et al., Ann Intern Med. 1961; 55:33-50; Müller et al., *Acta Med Scand Suppl.* 1938(89): 75-84; Yusuf et al., *Lancet.* 2004; 364(9438):937-952). Sub-endothelial accumulation of LDLc in blood vessels is an important initiating event in atherosclerosis, leading to pathological accumulation of lipids, cell debris, chronic inflammation leading to severe ASCVD (Mackay et al., *World Health Organization.* 2004:112p; Lusis, *Nature.* 2000; 407(6801):233-241). Through binding of apolipoprotein B100 (ApoB100), atherogenic plasma LDL particles are mainly cleared by LDL receptor (LDLR)-mediated endocytosis in the liver (Brown et al., *Science.* 1986; 232(4746): 34-47). Heterozygous familial hypercholesterolemia (HeFH) is a common, underdiagnosed and undertreated genetic disease that affects 1 in 250 people (Nordestgaard et al., *Eur Heart J.* 2013; 34(45):3478-3490a). FH patients inherit genetic mutations mostly in LDLR but also in APOB, ARH and APOE loci and have lifelong very high levels of circulating LDLc and premature development of ASCVD generally in their first decades of life (Section 2.1.3) (Marduel et al., *Hum Mutat.* 2013; 34(1):83-87; Rader et al., *J Clin Invest.* 2003; 111(12):1795-1803). In 2003, a third FH locus was identified in patients having a gain-of-function mutation in the gene encoding for proprotein convertase subtilisin/kexin type 9 (PCSK9) (Seidah et al., *Proc Nat/ Acad Sci USA.* 2003; 100(3):928-933; Abifadel et al., *Nat Genet.* 2003; 34(2):154-156; Abifadel et al., *Atherosclerosis.* 2012; 223(2):394-400), a natural inducer of LDLR degradation (Maxwell et al., *Proc Natl Acad Sci USA.* 2004; 101(18):7100-7105; Benjannet et al., *J Biol Chem.* 2004; 279(47):48865-48875; Park et al., *J Biol Chem.* 2004; 279 (48):50630-50638). A renewed clinical enthusiasm for new therapies originated from the discovery of loss-of-function genetic mutations at the PCSK9 locus that robustly lower circulating LDLc (>80%) and reduce cardiovascular events up to ~88% in humans without any adverse effects (Section 2.1.3) (Cohen et al., *Nat Genet.* 2005; 37(2):161-165; Berge et al., *Arteriosclerosis, thrombosis, and vascular biology.* 2006; 26(5):1094-1100; Hooper et al., *Atherosclerosis.* 2007; 193(2):445-448; Zhao et al., *Am J Hum Genet.* 2006; 79(3):514-523; Cohen et al., *N Engl J Med.* 2006; 354(12): 1264-1272). Accordingly, PCSK9 was highlighted as a highly safe, genetically validated and unprecedented powerful target to lower LDLc and to protect against ASCVD events such as heart attacks and stroke.

In hepatocytes (Seidah et al., *Proc Natl Acad Sci USA.* 2003; 100(3):928-933), PCSK9 limits the capacity of the liver to clear excess of circulating LDLc by directly binding and inducing the degradation of the LDL receptor (Maxwell et al., *Proc Nat/Acad Sci USA.* 2004; 101(18):7100-7105; Zhang et al., *J Biol Chem.* 2007; 282(25):18602-18612). Clinical trials using anti-PCSK9 monoclonal antibodies that block PCSK9-LDLR interaction have shown to significantly reduce LDLc levels up to 70%, on top of statins, as compared to ~30% when statin is used as monotherapy (Stein et al., *N Engl J Med.* 2012; 366(12):1108-1118; Stein et al., *Lancet.* 2012; 380(9836):29-36; McKenney et al., *J Am Coll Cardiol.* 2012; 59(25):2344-2353). In patients with stable cardiovascular disease, GLAGOV, FOURIER, OSLER and EBBINGHAUS Phase 3 clinical trials demonstrated that monthly-injected monoclonal PCSK9 antibodies significantly reduced LDLc, atherosclerotic plaque progression and prevented major cardiovascular events without any other adverse effects over a 2-year period (Nicholls et al., *JAMA.* 2016; 316(22):2373-2384; Sabatine et al., *N Engl J Med.* 2017; 376(18):1713-1722; Koren et al., *JAMA Cardiol.* 2017; Sabatine et al., *N Engl J Med.* 2015; 372(16): 1500-1509). With Pfizer that recently discontinued its PCSK9 Bococizumab program due to appearance of anti-drug antibodies and lack of efficacy (Ridker et al., *N Engl J Med.* 2017; 376(16):1517-1526; Ridker et al., *N Engl J Med.* 2017; 376(16):1527-1539), only two PCSK9 monoclonal antibodies that got approval in 2015 (Repatha®, Amgen and Praluent®, Sanofi-Regeneron) are currently used in the clinic. Alnylam Pharmaceuticals is developing PCSK9 RNA interfering injectable drugs that could potentially be used in the clinic at lower cost, but safety still remains to be demonstrated in much larger clinical trials (Ray et al., *N Engl J Med.* 2017; 376(15):1430-1440). Currently, there are no validated, cost-effective, and orally available small molecule LDLR enhancers (i.e., PCSK9 inhibitors) under development to fill the urgent needs of new lipid-lowering therapies for patients with high cardiovascular risk.

A recent international meta-analysis of over 200 clinical studies including more than 2 million participants with over 20 million person-years of follow-up and over 150 000 cardiovascular events unequivocally establishes a direct causal link between LDLc and incidence of major adverse cardiac events (MACE) such as heart attacks and stroke (Ference et al., *Eur Heart J.* 2017). There is a consensus between clinicians and scientists that any mechanism significantly and specifically lowering plasma LDLc concentration reduces the risk of ASCVD (Silverman et al., *JAMA.* 2016; 316(12):1289-1297). A separate meta-analysis of data from 170 000 participants in 26 randomized trials concluded that annual rate of MACE decreases by 20% for each mmol/L reduction of circulating LDLc (~25% in normolipidemic patients) (O'Keefe et al., *J Am Coll Cardiol.* 2004; 43(11):2142-2146; Baignet et al., *Lancet.* 2010; 376(9753): 1670-1681). Indeed, it is expected that PCSK9 inhibitors that increase LDLR levels and lower LDLc by >50% will prevent MACE by 50% over a 5-year period. Indeed, recent data from FOURIER and ODYSSEY Outcomes Phase 3 trials (PCSK9 mAbs from Amgen and Sanofi-Regeneron) revealed that additional ~50% LDLc lowering in hypercholesterolemic patients on maximally-tolerated statin therapy have up to 24% reduction in primary endpoint (Coronary Heart Disease death, myocardial infarction, ischemic stroke, unstable angina requiring hospitalization) and 30% reduction of all-cause mortality after only 3 years of treatment as compared to placebo (Sabatine et al., *N Engl J Med*. 2017; 376(18):1713-1722; Schwartz et al., *N Engl J Med*. 2018). Unfortunately, due to high annual costs (~6,000$-14,000$/year/patient) and chronic need of lipid-lowering therapies for the indicated group of patients, anti-PCSK9 antibodies do not reach incremental cost-effectiveness threshold and prescriptions are highly rejected from payers for high-risk patients with FH or history of ASCVD even with proven cardiovascular event reduction rates (Kazi et al., *JAMA*. 2016; 316(7):743-753; Knowles et al., *Circulation*. 2017; 135(22):2204-2206).

Statins, currently the most prescribed class of lipid-lowering drugs, decrease LDLc in the bloodstream by ~30-40% mainly by increasing LDLR levels in the liver (Kapur et al., *Vasc Health Risk Manag*. 2008; 4(2):341-353). In addition, combination of statins with ezetimibe, bile-acid sequestrants, or niacin produces an additional 10 to 20% decrease in LDLc (Hou et al., *Endocrinol Metab Clin North Am*. 2009; 38(1):79-97). However, even if these therapies can help achieve significant reductions in LDLc, more efficient lipid-lowering therapies are still needed, especially for patients with FH or history of ASCVD with very high, uncontrolled, LDLc levels.

About 42 million high-risk individuals (8.4% of adult population) in North America and Europe alone are either statin-intolerant and/or fail to achieve recommended LDLc targets despite changing their diets, exercising and on maximally tolerated statin therapies (Kazi et al., *JAMA*. 2016; 316(7):743-753; Bruckert et al., *Cardiovasc Drugs Ther*. 2005; 19(6):403-414; Mozaffarian et al., *Circulation*. 2015; 131(4):e29-322). In order to fill these important clinical needs, PCSK9 inhibitors or any therapies that strongly increase LDLR could be suitable to significantly reduce LDLc and prevent MACE in those high-risk patients. Indeed, a meta-regression analysis from 312,175 participants highlighted that upregulation of LDLR expression by statin and non-statin therapies is the key target to reduce LDLc and to drastically reduce major cardiovascular events.[34]

There remains a need for improved therapeutics for treating atherosclerotic cardiovascular diseases.

SUMMARY OF THE INVENTION

The compounds of the present invention are useful to modulate PCSK9 activities and represent a series of low-density lipoprotein receptor (LDLR) inducers for treating elevated plasma cholesterol and related conditions. The present invention relates to a series of PCSK9 interacting compounds and their pharmaceutically acceptable derivatives thereof (e.g., salts and solvates), which increase LDLR levels.

A first aspect features a compound having the structure of formula (I)

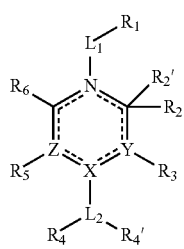

(I)

wherein:
each of Z, X, and Y is independently N, C, CH, or $CH_2$;
=== indicates an optional single or double bond;
$L_1$ is absent,

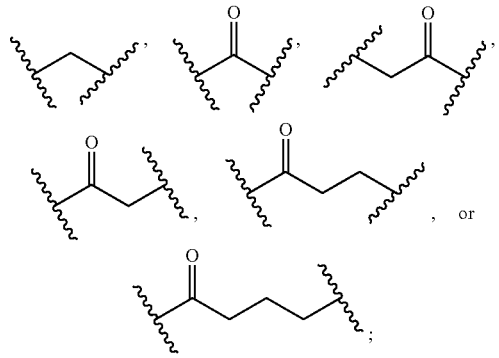
, or $L_2$ is absent,

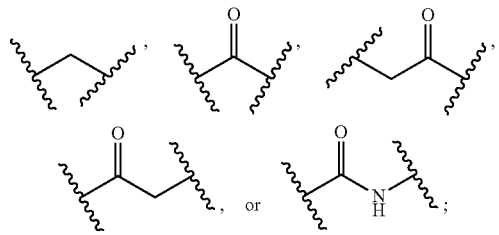
, or $R_1$ is optionally H, optionally substituted $C_1$-$C_4$ alkyl, optionally substituted $C_{2-4}$ acyl, optionally substituted $C_{3-5}$ heterocyclyl, optionally substituted $C_{2-10}$ heteroaryl, or optionally substituted $C_{6-10}$ aryl;

$R_2$ is optionally H,

optionally substituted $C_{1-4}$ alkyl, optionally substituted $C_4$ heteroalkyl, optionally substituted $C_7$ heterocyclylalkyl, optionally substituted $C_{4-5}$ heterocyclyl, optionally substituted $C_{5-9}$ heteroaryl, optionally substituted $C_4$ alkenyl, or optionally substituted $C_6$ aryl;

$R_2'$ is optionally absent; H, or optionally substituted $C_1$ alkyl;

$R_3$ is absent, H,

substituted $C_1$ heteroalkyl, optionally substituted $C_3$ heterocycylalkyl, optionally substituted heterocyclyl, optionally substituted $C_3$ heteroarylalkyl, optionally substituted $C_7$ heteroaryl, optionally substituted $C_6$ aryl, optionally substituted $C_{2-3}$ heteroalkenyl, optionally substituted $C_7$ alkenyl, or optionally substituted amino;

$R_4$ is absent, H, optionally substituted alkyl, optionally substituted $C_6$ arylalkyl, optionally substituted amino, optionally substituted C$_8$ alkyenyl, optionally substituted C$_{4-6}$ heterocyclyl, optionally substituted C$_7$ heteroaryl, optionally substituted C$_{10}$ ether; optionally substituted C$_6$ aryl;

R$_4$' is absent, H, optionally substituted C$_8$ arylalkyl, optionally substituted C$_6$ ether, optionally substituted C$_8$ alkyenyl;

R$_5$ is absent, H, optionally substituted C$_{4-7}$ alkenyl, optionally substituted C$_{11}$ arylalkyl, or optionally substituted C$_3$ heteroalkenyl;

R$_6$ is H, $$\overset{O,}{\|}$$

optionally substituted C$_6$ aryl, optionally substituted C$_5$ heteroaryl, optionally substituted amino, optionally substituted C$_5$ heterocyclylalkyl, or optionally substituted C$_4$ alkyenyl;

R$_1$ and R$_2$, together with the atoms to which each is attached, may be combined to form an optionally substituted C$_6$ aryl, or C$_5$ heterocyclyl;

R$_2$ and R$_2$', together with the atom to which each is attached, may be combined to form an optionally substituted C$_5$ heterocyclyl;

R$_2$ and R$_3$, together with the atoms to which each is attached, may be combined to form an optionally substituted C$_6$ cycloalkyl;

R$_3$ and R$_4$, together with the atoms to which each is attached, may be combined to form an optionally substituted C$_4$ heteroaryl, or an optionally substituted C$_6$ aryl;

R$_4$ and R$_4$, together with the atom to which each is attached, may be combined to form an optionally substituted C$_9$ aryl or optionally substituted C$_{8-9}$ heteroaryl;

R$_4$ and R$_5$, together with the atom to which each is attached, may be combined to form an optionally substituted C$_{3-4}$ heteroaryl, or an optionally substituted C$_6$ aryl; and R$_5$ and R$_6$, together with the atoms to which each is attached, may be combined to form an optionally substituted C$_6$ aryl.

Some embodiments of the first aspect feature a compound having the structure of any one of compounds 1-52 of Table 1, or a pharmaceutically acceptable salt or solvate thereof.

TABLE 1

Exemplified compounds

| # | Compound |
|---|---|
| 1 | |
| 2 | |
| 3 | |

TABLE 1-continued
Exemplified compounds
| # | Compound |
|---|---|
| 4 | 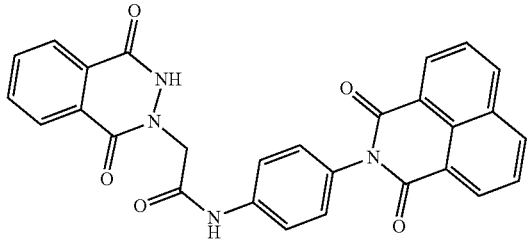 [SMILES: O=C(Cn1[nH]c(=O)c2ccccc2c1=O)Nc1ccc(N2C(=O)c3cccc4cccc(c34)C2=O)cc1] |
| 5 | 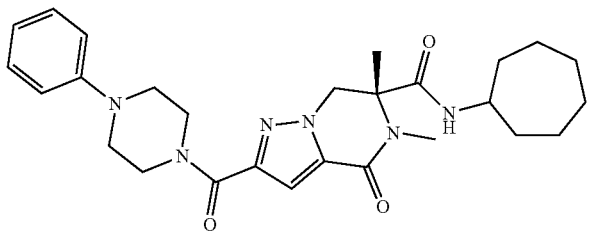 [SMILES: CN1C(=O)c2cc(C(=O)N3CCN(c4ccccc4)CC3)nn2C[C@]1(C)C(=O)NC1CCCCCC1] |
| 6 | 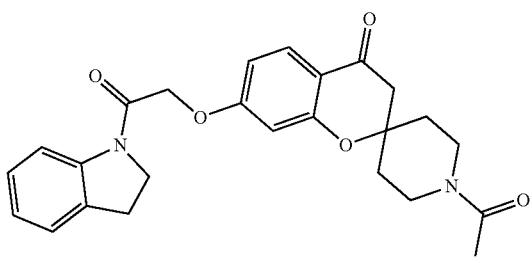 [SMILES: CC(=O)N1CCC2(CC1)CC(=O)c1ccc(OCC(=O)N3CCc4ccccc43)cc1O2] |
| 7 | 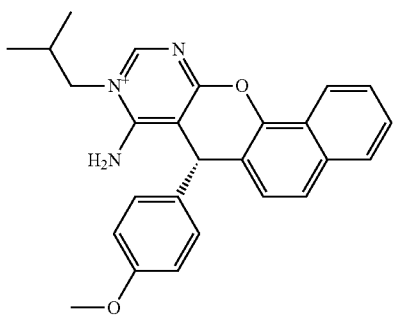 [SMILES: COc1ccc([C@H]2c3ccc4ccccc4c3Oc3nc[n+](CC(C)C)c(N)c32)cc1] |
| 8 | 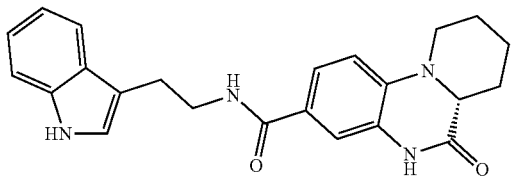 [SMILES: O=C(NCCc1c[nH]c2ccccc12)c1ccc2c(c1)NC(=O)[C@H]1CCCCN21] |
| 9 | 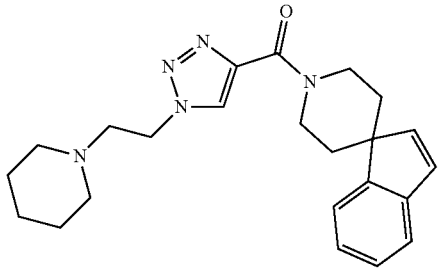 [SMILES: O=C(c1cn(CCN2CCCCC2)nn1)N1CCC2(C=Cc3ccccc32)CC1] |

TABLE 1-continued
Exemplified compounds
| # | Compound |
|---|---|
| 10 | 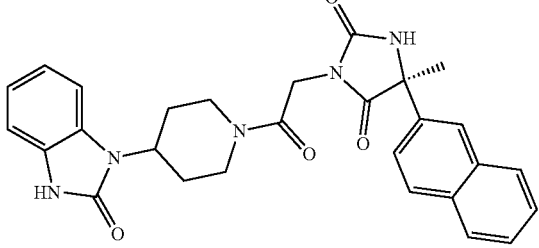 |
| 11 | 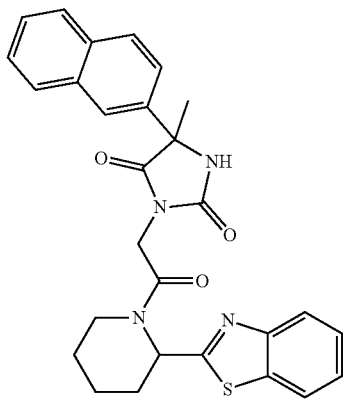 [SMILES: CC1(c2ccc3ccccc3c2)NC(=O)N(CC(=O)N2CCCCC2c2nc3ccccc3s2)C1=O] |
| 12 | 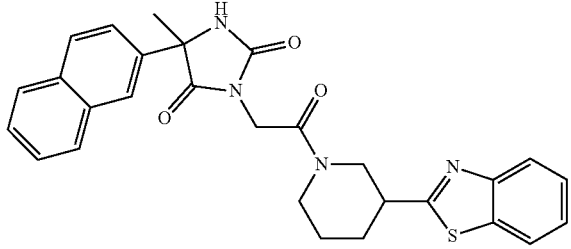 [SMILES: CC1(c2ccc3ccccc3c2)NC(=O)N(CC(=O)N2CCCC(c3nc4ccccc4s3)C2)C1=O] |
| 13 | 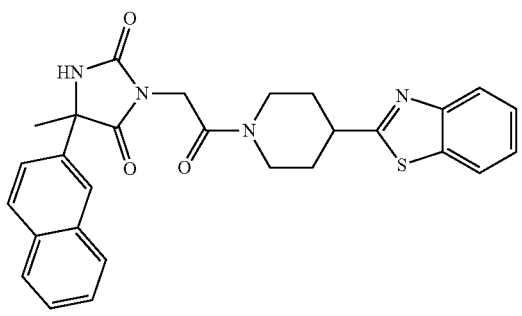 [SMILES: CC1(c2ccc3ccccc3c2)NC(=O)N(CC(=O)N2CCC(c3nc4ccccc4s3)CC2)C1=O] |
| 14 | 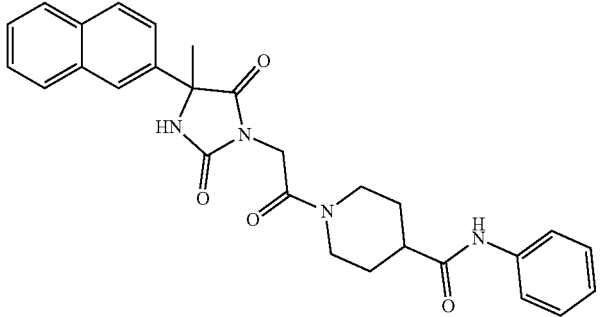 [SMILES: CC1(c2ccc3ccccc3c2)NC(=O)N(CC(=O)N2CCC(C(=O)Nc3ccccc3)CC2)C1=O] |

TABLE 1-continued
Exemplified compounds
| # | Compound |
|---|---|
| 15 | 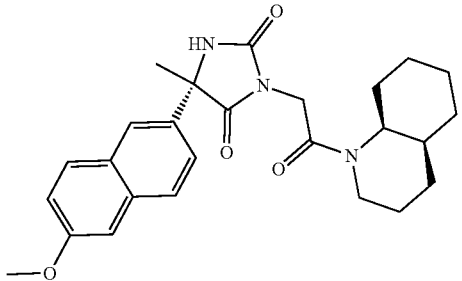 [SMILES: COc1ccc2cc([C@]3(C)NC(=O)N(CC(=O)N4CCC[C@@H]5CCCC[C@@H]54)C3=O)ccc2c1] |
| 16 | 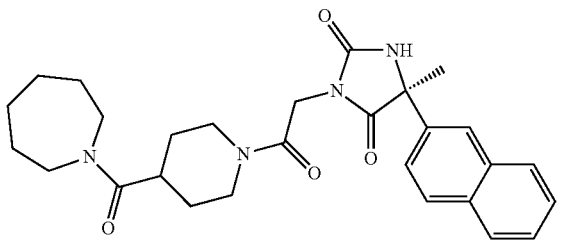 [SMILES: C[C@@]1(c2ccc3ccccc3c2)NC(=O)N(CC(=O)N2CCC(C(=O)N3CCCCCC3)CC2)C1=O] |
| 17 | 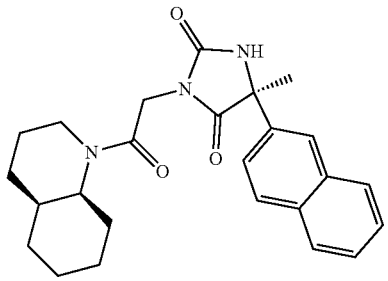 [SMILES: C[C@@]1(c2ccc3ccccc3c2)NC(=O)N(CC(=O)N2CCC[C@@H]3CCCC[C@@H]32)C1=O] |
| 18 | 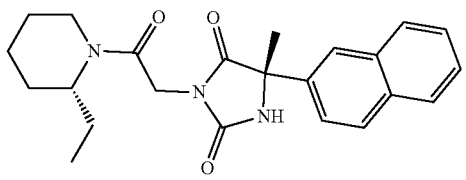 [SMILES: CC[C@@H]1CCCCN1C(=O)CN1C(=O)N[C@@](C)(c2ccc3ccccc3c2)C1=O] |
| 19 | 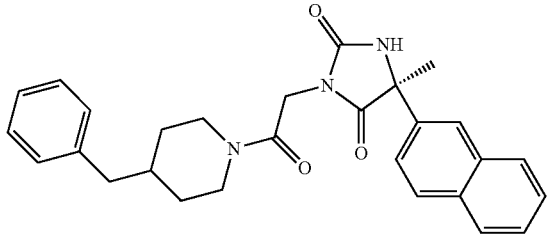 [SMILES: C[C@@]1(c2ccc3ccccc3c2)NC(=O)N(CC(=O)N2CCC(Cc3ccccc3)CC2)C1=O] |
| 20 | 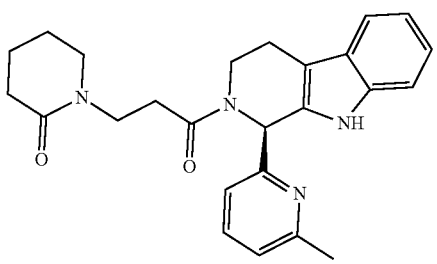 [SMILES: Cc1cccc([C@@H]2c3[nH]c4ccccc4c3CCN2C(=O)CCN2CCCCC2=O)n1] |

TABLE 1-continued
Exemplified compounds
| # | Compound |
|---|---|
| 21 | 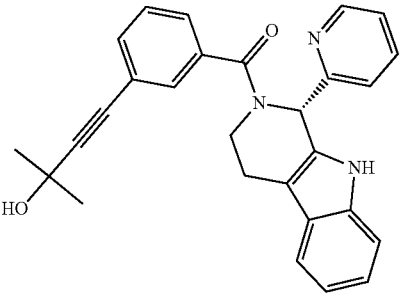 [SMILES: CC(C)(O)C#Cc1cccc(C(=O)N2CCc3c([nH]c4ccccc34)[C@H]2c2ccccn2)c1] |
| 22 | 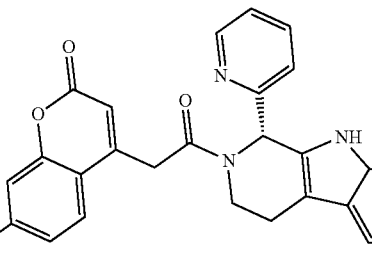 |
| 23 | 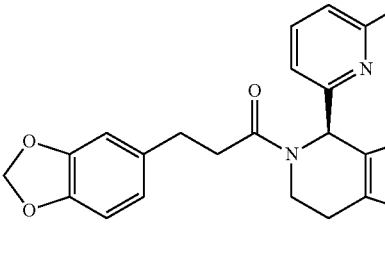 |
| 24 | 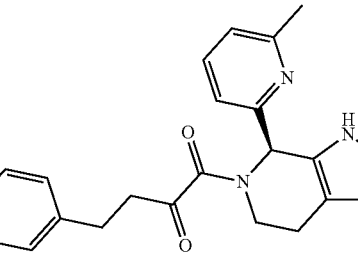 |
| 25 | 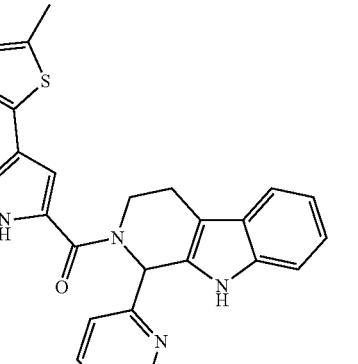 |

TABLE 1-continued
Exemplified compounds
| # | Compound |
|---|---|
| 26 | 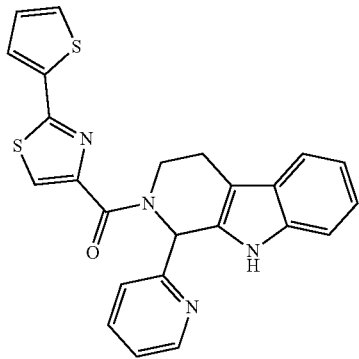 [SMILES: O=C(c1csc(-c2cccs2)n1)N1CCc2c([nH]c3ccccc23)C1c1ccccn1] |
| 27 | 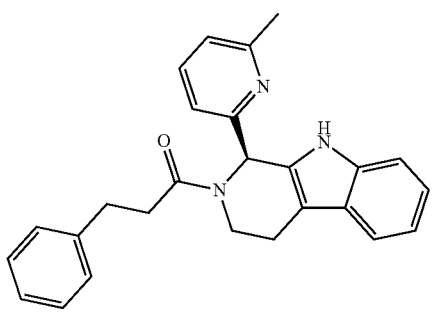 [SMILES: Cc1cccc([C@H]2c3[nH]c4ccccc4c3CCN2C(=O)CCc2ccccc2)n1] |
| 28 | 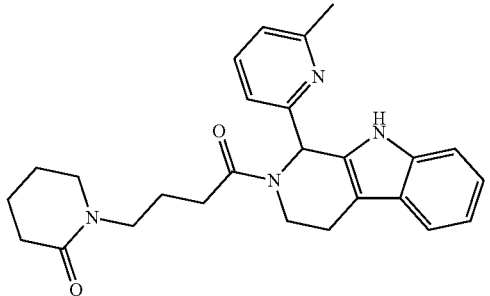 [SMILES: Cc1cccc(C2c3[nH]c4ccccc4c3CCN2C(=O)CCCN2CCCCC2=O)n1] |
| 29 | 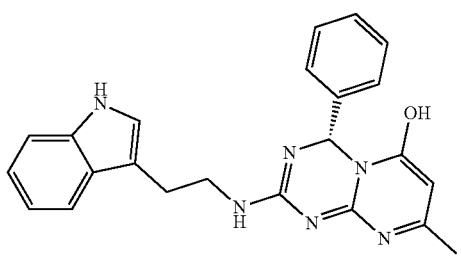 [SMILES: CC1=NC2=NC(NCCc3c[nH]c4ccccc34)=N[C@H](c3ccccc3)N2C(O)=C1] |
| 30 | 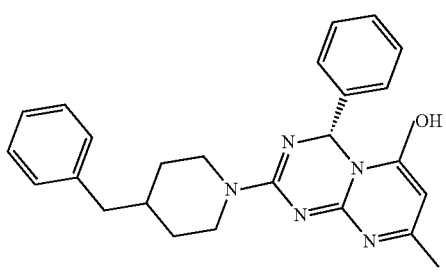 |

TABLE 1-continued

Exemplified compounds

| # | Compound |
|---|---|
| 31 | |
| 32 | |
| 33 | |
| 34 | |
| 35 | |
| 36 | |

TABLE 1-continued
Exemplified compounds
| # | Compound |
|---|---|
| 37 | 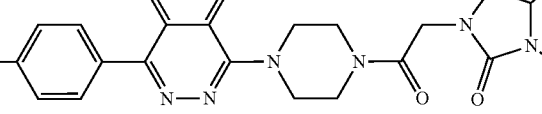 |
| 38 | 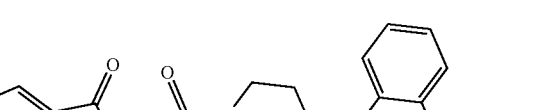 |
| 39 | 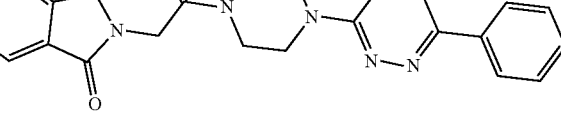 |
| 40 | 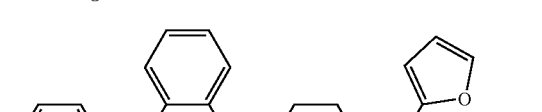 |
| 41 | 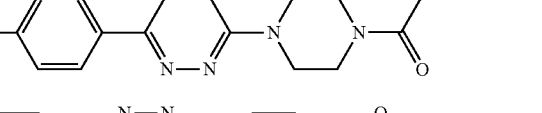 |
| 42 | 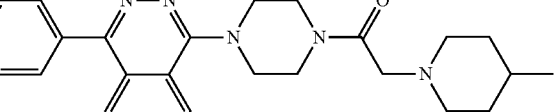 |

TABLE 1-continued
Exemplified compounds
| # | Compound |
|---|---|
| 43 | 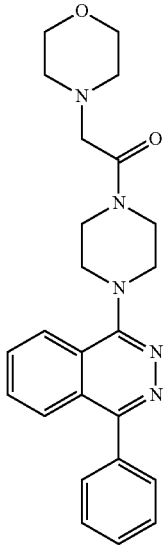 |
| 44 | 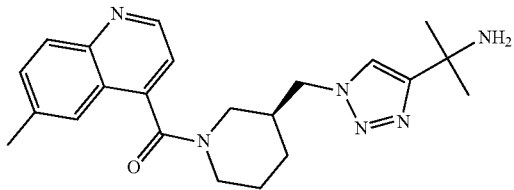 [SMILES: Cc1ccc2nccc(C(=O)N3CCC[C@H](Cn4cc(C(C)(C)N)nn4)C3)c2c1] |
| 45 | 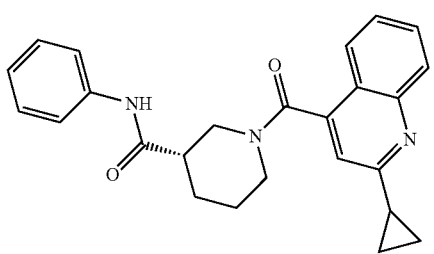 [SMILES: O=C(Nc1ccccc1)[C@H]1CCCN(C(=O)c2cc(C3CC3)nc3ccccc23)C1] |
| 46 | 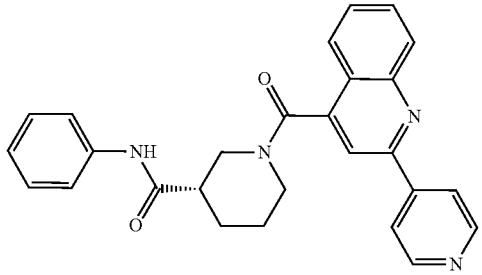 [SMILES: O=C(Nc1ccccc1)[C@H]1CCCN(C(=O)c2cc(-c3ccncc3)nc3ccccc23)C1] |

TABLE 1-continued

Exemplified compounds

| # | Compound |
|---|---|
| 47 | |
| 48 | |
| 49 | |
| 50 | |

TABLE 1-continued
Exemplified compounds
| # | Compound |
|---|---|
| 51 | 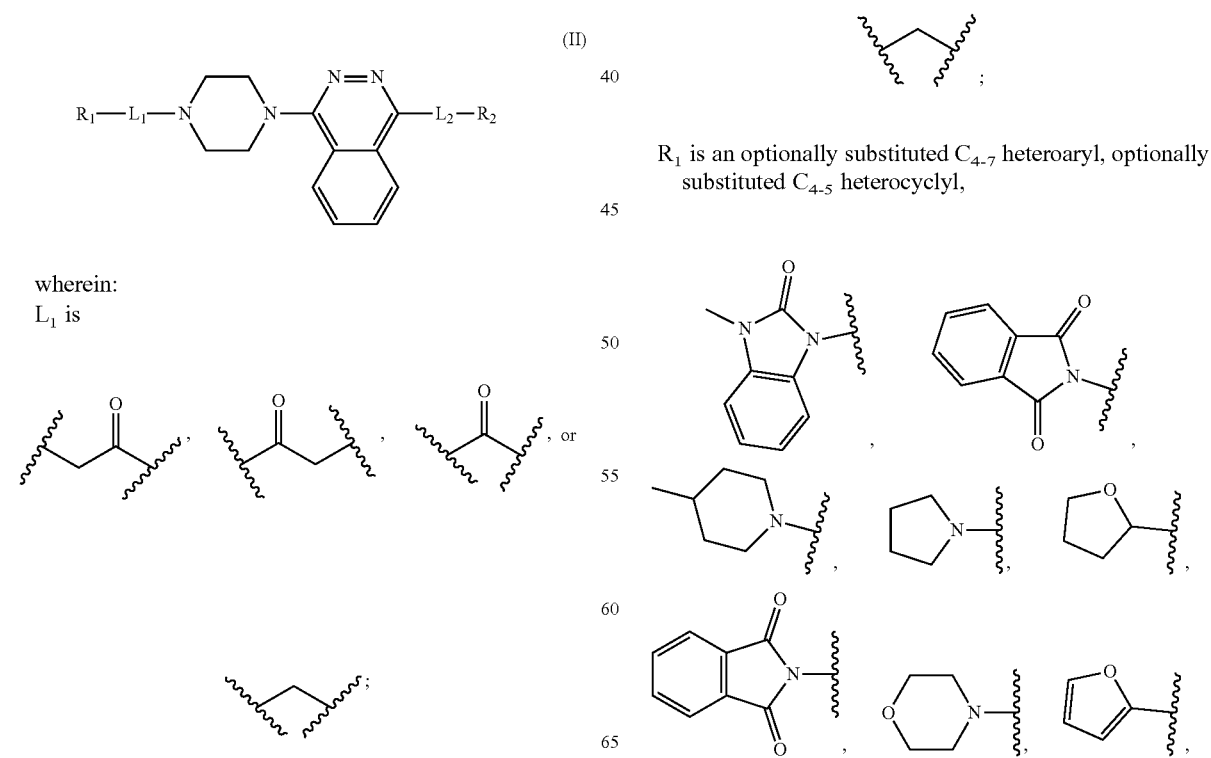 |
| 52 | |
A second aspect features a compound having the structure of formula (II)
(II)
$R_1—L_1—N\underset{}{\frown}N—\text{(phthalazine)}—L_2—R_2$
wherein:
$L_1$ is
[structures], or [structure];
$L_2$ is absent or
[structure];
$R_1$ is an optionally substituted $C_{4-7}$ heteroaryl, optionally substituted $C_{4-5}$ heterocyclyl,
[structures]

-continued

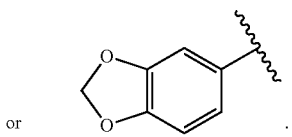

or

In some embodiments, R₁ is

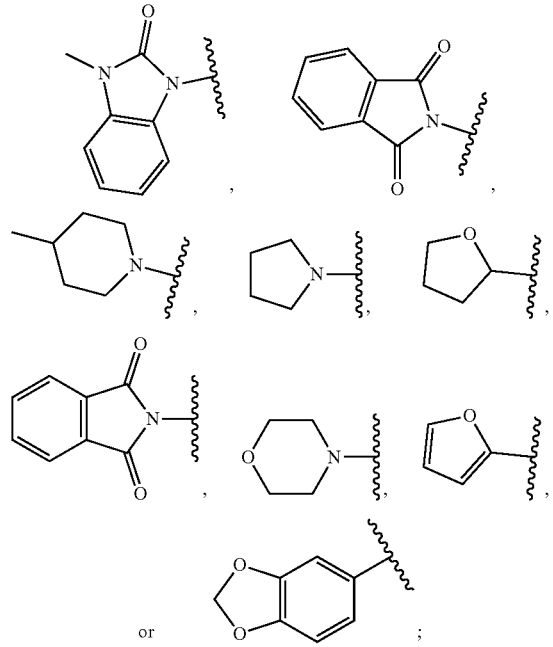

and

R₂ is an optionally substituted C₆ aryl, optionally substituted C₅ heteroaryl,

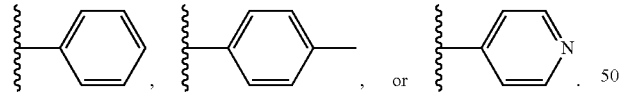

In some embodiments, R₂ is

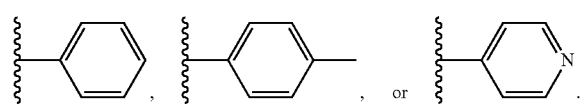

Some embodiments of the second aspect feature a compound having the structure of one of the compounds 1-52 of Table 1, or a pharmaceutically acceptable salt or solvate thereof.

A third aspect features a compound having the structure of formula (III):

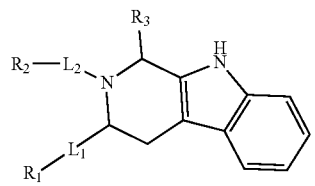

(III)

wherein:

L₁ is

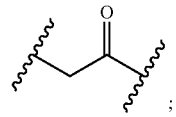 [SMILES: *CC(*)=O]

;

L₂ is

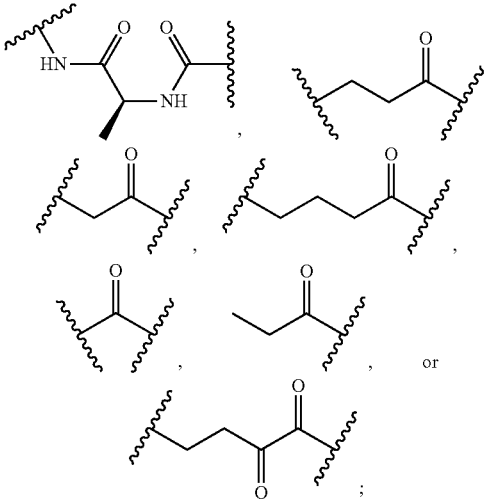

;

R₁ is an optionally substituted C₈ heteroaryl, or

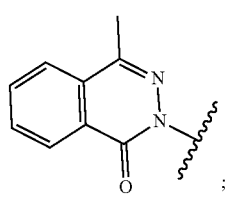 [SMILES: *n1nc(C)c2ccccc2c1=O]

;

In some embodiments, R₁ is

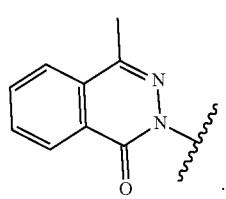 [SMILES: *n1nc(C)c2ccccc2c1=O]

.

R2 is an optionally substituted C$_5$ carbocyclyl, optionally substituted C$_5$ heterocyclyl, optionally N-substituted C$_6$ aryl, optionally substituted C$_{3-9}$ heteroaryl,

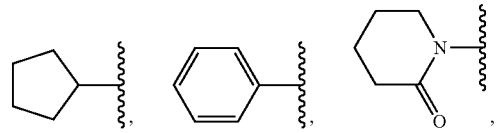

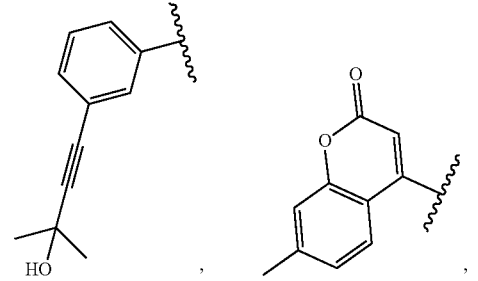, 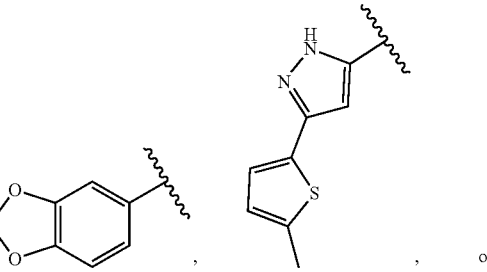, or 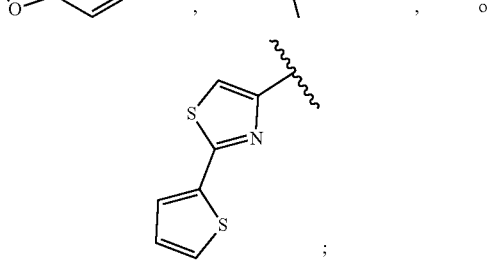;

and

R$_3$ is an optionally substituted C$_1$ alkyl, optionally substituted C$_5$ heteroaryl,

, , or .

In some embodiments, R$_2$ is

, 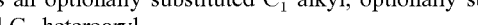, ,

, ,

, , or

;

and

R$_3$ is an optionally substituted C$_1$ alkyl, optionally substituted C$_5$ heteroaryl,

, , or .

In some embodiments, R$_3$ is

, , or .

In some embodiments, R$_2$ and R$_3$, together with the atoms to which each is attached, may be combined to form an optionally substituted C$_8$ aryl. In some embodiments, the optionally substituted C$_8$ aryl is

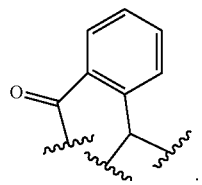 [SMILES: *C(=O)c1ccccc1C(*)*]

Some embodiments of the third aspect feature a compound having the structure of one of the compounds 1-52 of Table 1, or a pharmaceutically acceptable salt or solvate thereof.

A fourth aspect features a compound having the structure of formula (IV):

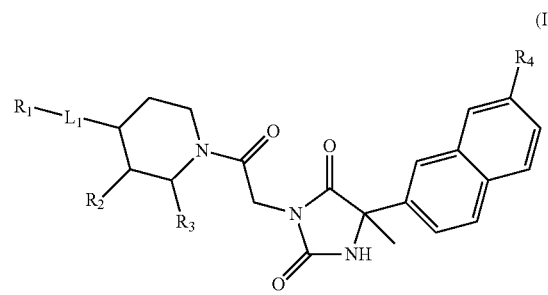

(IV)

wherein:

$L_1$ is

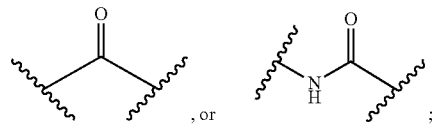

$R_1$ is an optionally substituted $C_7$ heterocyclyl, optionally substituted $C_7$ heteroaryl, optionally substituted $C_6$ aryl,

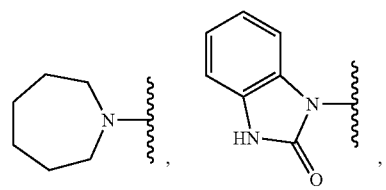

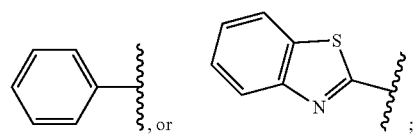

and each or $R_2$ and $R_3$ is an optionally substituted $C_7$ heteroaryl, optionally substituted $C_2$ alkyl,

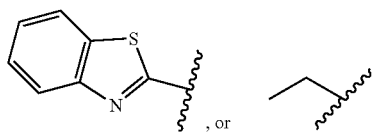

In some embodiments, $R_1$ is,

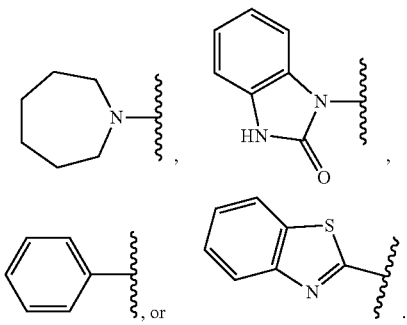

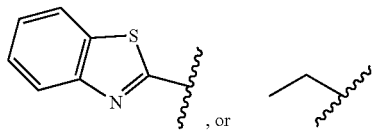

In some embodiments, each of $R_2$ or $R_3$ is

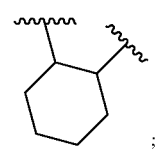

In some embodiments, $R_2$ and $R_3$, together with the atoms to which each is attached, may be combined to form an optionally substituted $C_6$ cycloalkyl. In some embodiments, the optionally substituted $C_6$ cycloalkyl is

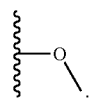

and $R_4$ is absent or (O-substituent structure)

Some embodiments of the fourth aspect feature a compound having the structure of one of the compounds 1-52 of Table 1, or a pharmaceutically acceptable salt or solvate thereof.

A fifth aspect features a compound having the structure of formula (V):

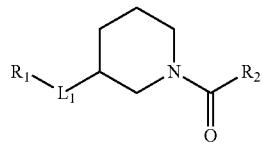
(V)
wherein:
L₁ is
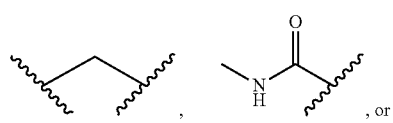
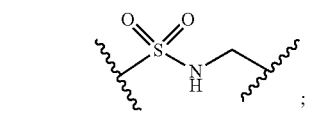
R₁ is an optionally substituted C₆ aryl, an optionally substituted C₂-C₆ heterocyclyl,
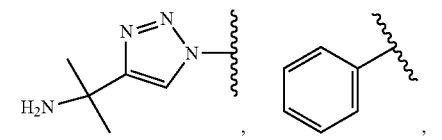
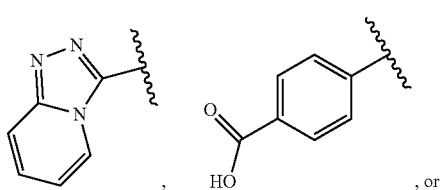
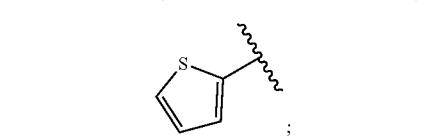
and
R₂ is an optionally substituted C₆ aryl, optionally substituted C₉ heterocyclyl,
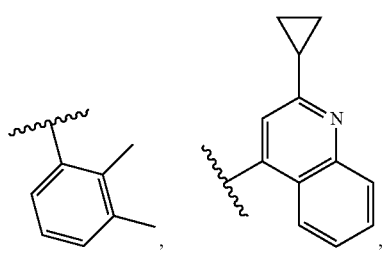
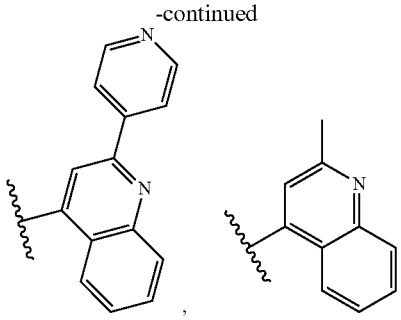
In some embodiments, R₁ is
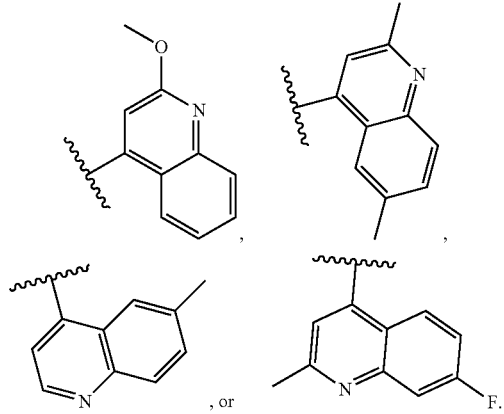
and
R₂ is an optionally substituted C₆ aryl, optionally substituted C₉ heterocyclyl,
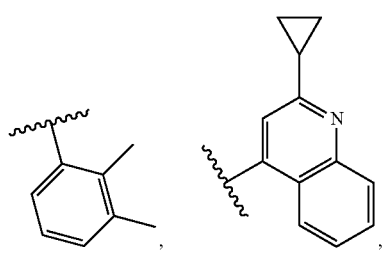

-continued

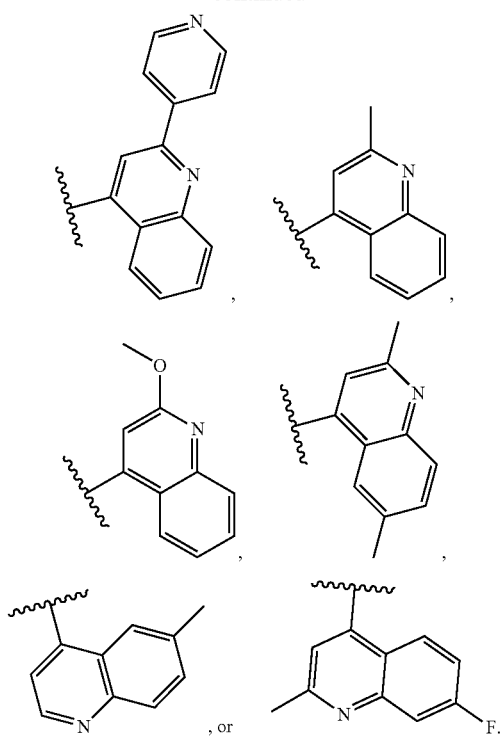

In some embodiments, R₂ is

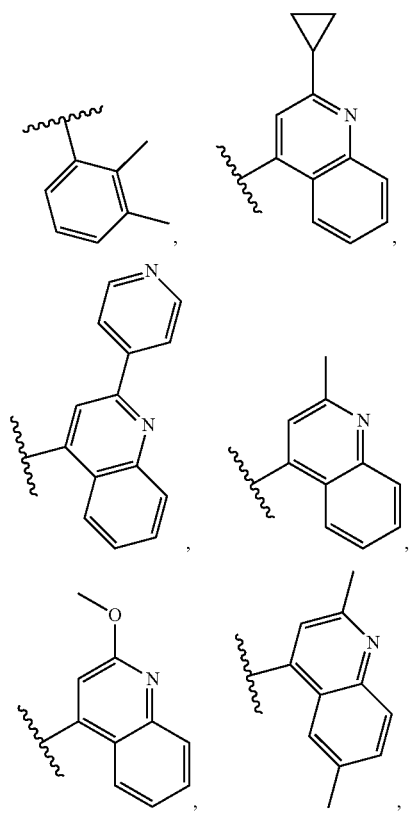

-continued

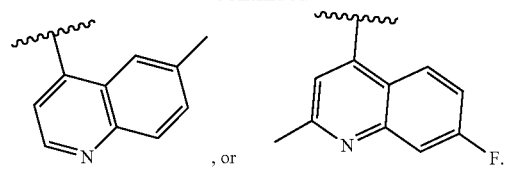
, or

Some embodiments of the fifth aspect feature a compound having the structure of one of the compounds 1-52 of Table 1, or a pharmaceutically acceptable salt or solvate thereof.

A sixth aspect features a compound having the structure of formula (VI):

$$\text{(VI)}$$

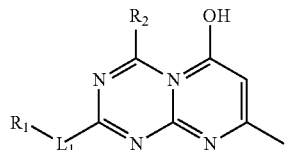

wherein:

L₁ is

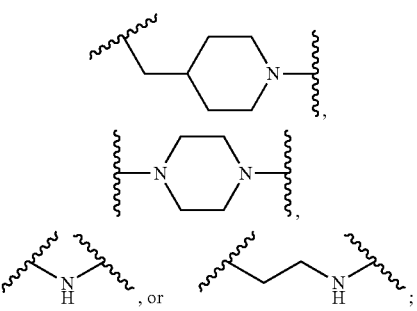
, or and

R₁ is an optionally substituted C₆ aryl, optionally substituted C₈ heteroaryl,

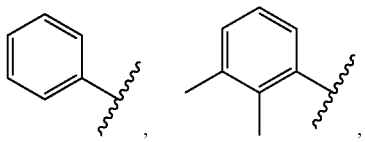
,

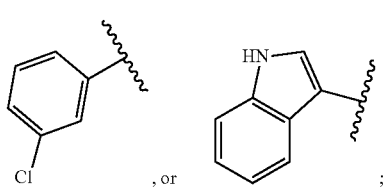
, or ;

and R₂ is an optionally substituted C₅ heteroaryl, an optionally substituted C₆ aryl,

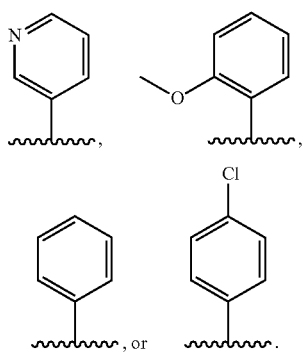

In some embodiments, $R_1$ is

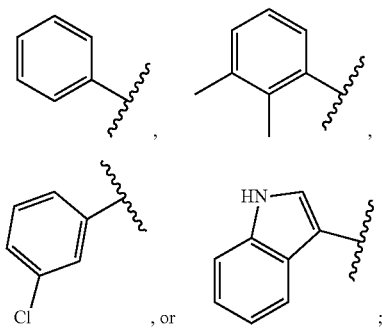

and $R_2$ is an optionally substituted $C_5$ heteroaryl, an optionally substituted $C_6$ aryl,

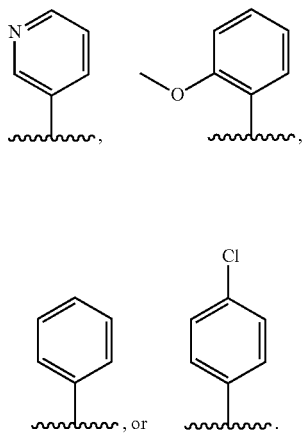

In some embodiments, $R_2$ is

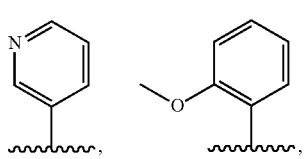

-continued

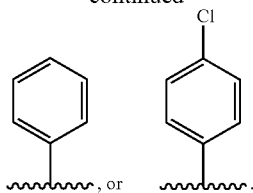

Some embodiments of the sixth aspect feature a compound having the structure of one of the compounds 1-52 of Table 1, or a pharmaceutically acceptable salt or solvate thereof.

Another aspect features a pharmaceutical composition or pharmaceutically acceptable formulation containing a therapeutically effective amount of at least one compound (e.g., such as one or more of compounds 1-52 of Table 1, or a compound of Formula I, II, III, IV, V, or VI) or a pharmaceutically acceptable salt or solvate thereof. In some embodiments, the pharmaceutical composition may further include a pharmaceutically acceptable carrier, excipient, or adjuvant.

Other aspects feature methods of lowering cholesterol level (e.g., elevated cholesterol level) in a subject in need thereof (e.g., in bloodstream of a subject in need thereof) by administering to the subject a therapeutically effective amount (e.g., a cholesterol lowering amount) of at least one compound of the present invention (e.g., such as one or more of compounds 1-52 of Table 1, or a compound of Formula I, II, III, IV, V, or VI), or a pharmaceutically acceptable salt, solvate or composition thereof. Further provided are methods of binding PCSK9, modulating PCSK9 activities and inducing LDLR expression and/or LDLR activity in a subject in need thereof (e.g., in a cell, such as a hepatic cell in a subject in need thereof) by administering to the subject a therapeutically effective amount of at least one compound of the present invention (e.g., such as one or more of compounds 1-52 of Table 1, or a compound of Formula I, II, III, IV, V, or VI) or a pharmaceutically acceptable salt, solvate or composition thereof. In some embodiments, the subject has been diagnosed with or is predisposed to (e.g., at a risk of developing) a disease or condition that is caused or mediated by elevated cholesterol level (e.g., an elevated cholesterol associated disease, such as atherosclerosis, hypercholesterolemia (e.g., heterozygous familial hypercholesterolemia or homozygous familial hypercholesterolemia), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure).

Other aspects feature methods of treating, reducing one or more symptoms of, delaying the onset of, and/or reducing the likelihood of occurrence of a disease or condition that is caused or mediated by elevated cholesterol level (e.g., an elevated cholesterol associated disease) in a subject in need thereof by administering to the subject a therapeutically effective amount of at least one compound of the present invention (e.g., such as one or more of compounds 1-52 of Table 1, or a compound of Formula I, II, III, IV, V, or VI), or a pharmaceutically acceptable salt, solvate or composition thereof. In some embodiments, the subject has been diagnosed with a disease or condition that is caused or mediated by elevated cholesterol level (e.g., an elevated cholesterol associated disease). In other embodiments, the subject is predisposed to (e.g., at a risk of developing) a disease or condition that is caused or mediated by elevated cholesterol level (e.g., an elevated cholesterol associated disease). Examples of diseases or conditions that are caused or mediated by elevated cholesterol level (e.g., elevated cholesterol associated diseases) include atherosclerosis, hypercholesterolemia (e.g., heterozygous familial hypercholesterolemia or homozygous familial hypercholesterolemia), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease, and congestive heart failure. In particular, diseases or conditions that are caused or mediated by elevated cholesterol level (e.g., elevated cholesterol associated diseases) include atherosclerosis and hypercholesterolemia.

In some embodiments, any one of the methods featured herein further includes administering to the subject one or more cholesterol lowering agents. In some embodiments, the subject has been treated with one or more cholesterol lowering agents prior to administering a compound of the present invention (e.g., such as one or more of compounds 1-52 of Table 1, or a compound of Formula I, II, III, IV, V, or VI), or a pharmaceutically acceptable salt, solvate or composition thereof. In some embodiments, treatment (e.g., prior treatment) with one or more cholesterol lowering agents does not effectively lower cholesterol level in the subject. Examples of cholesterol lowering agents (e.g., cholesterol lowering agents that can be administered prior to, concurrent with, or after administering one or more compounds of the present invention) include a lipase inhibitor, an 3-hydroxy-3-methyl-glutaryl-coenzyme A (HMG CoA) reductase inhibitor, an HMG CoA synthase inhibitor, an ATP citrate lyase inhibitor, a LDLR degradation inhibitor, a cholesteryl ester transfer protein (CETP) inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a microsomal triglyceride transfer protein (MTP) inhibitor, an ApoB secretion inhibitor, a proprotein convertase subtilisin kexin type 9 (PCSK9) gene expression inhibitor, an anti-PCSK9 antibody, a PCSK9 mRNA silencer, a fibrate, a niacin or a combination of niacin with a statin, an ion-exchange resin, an acyl-coenzyme A:cholesterol acyltransferase (ACAT) inhibitor and a bile acid sequestrant, an HMG-CoA reductase gene expression inhibitor, and an HMG-CoA synthase gene expression inhibitor. In some embodiments, the cholesterol lowering agent (e.g., cholesterol lowering agent that can be administered prior to, concurrent with, or after administering one or more compounds of the present invention) is one or more of atorvastatin, fluvastatin, lovastatin, pravastatin, rosuvastatin, simvastatin, pitavastatin, ezetimibe, a combination of ezetimibe and a statin (e.g. atorvastatin, rosuvastatin, simvastatin), gemfibrozil, fenfibrate, clofibrate, cholestyramine, colestipol, colesevelam, alirocumab, evolocumab, inclisiran, AT04A, lomitapide, or mipomersen. In particular embodiments, the cholesterol lowering agent (e.g., cholesterol lowering agent that can be administered prior to, concurrent with, or after administering one or more compounds of the present invention) is a cholesterol lowering agent listed in Table 3.

In some embodiments, any one of the methods featured herein further includes administering to the subject an agent that increases bioavailability and/or slows metabolism of the one or more compounds of the present invention (e.g., such as one or more of compounds 1-52 of Table 1, or a compound of Formula I, II, III, IV, V, or VI), or a pharmaceutically acceptable salt, solvate or composition thereof. In some embodiments, such agent (e.g., agent that increases bioavailability and/or slows metabolism of the one or more compounds of the present invention) is an inhibitor of at least one isoform of cytochrome P450 (CYP450), such as an inhibitor of CYP1A2, CYP2d6, CYP2C9, CYP2C19 or CYP3A4. In particular embodiments, such agent (e.g., agent that increases bioavailability and/or slows metabolism of the one or more compounds of the present invention) is an inhibitor of CYP3A4 (e.g., nefidipine or ritonavir).

Other aspects feature methods of binding, modulating PCSK9 activities and inducing LDLR expression and/or LDLR activity in a cell (e.g., a hepatic cell) by contacting the cell or circulating PCSK9 with an effective amount of at least one compound of the present invention (e.g., such as one or more of compounds 1-52 of Table 1, or a compound of Formula I, II, III, IV, V, or VI), or a pharmaceutically acceptable salt, solvate or composition thereof. In some embodiments, the method further includes contacting the cell with one or more additional cholesterol lowering agents (e.g., one or more of a lipase inhibitor, an HMG CoA reductase inhibitor, an HMG CoA synthase inhibitor, an ATP citrate lyase inhibitor, a LDLR degradation inhibitor, a CETP inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a MTP inhibitor, an ApoB secretion inhibitor, a PCSK9 gene expression inhibitor, an anti-PCSK9 antibody, a PCSK9 mRNA silencer, a fibrate, a niacin or a combination of niacin with a statin, an ion-exchange resin, an ACAT inhibitor and a bile acid sequestrant, an HMG-CoA reductase gene expression inhibitor, or an HMG-CoA synthase gene expression inhibitor). In some embodiments, the cholesterol lowering agent is one or more of atorvastatin, fluvastatin, lovastatin, pravastatin, rosuvastatin, simvastatin, pitavastatin, ezetimibe, a combination of ezetimibe and a statin (e.g., atorvastatin, rosuvastatin, simvastatin), gemfibrozil, fenfibrate, clofibrate, cholestyramine, colestipol, colesevelam, alirocumab, evolocumab, inclisiran, AT04A, lomitapide, or mipomersen. In particular embodiments, the cholesterol lowering agent is a cholesterol lowering agent listed in Table 3. In some embodiments, the method further includes contacting the cell with an agent that increases bioavailability and/or slows metabolism of the one or more compounds of the present invention (e.g., such as one or more of compounds 1-52 of Table 1, or a compound of Formula I, II, III, IV, V, or VI), or a pharmaceutically acceptable salt, solvate or composition thereof. In some embodiments, such agent (e.g., agent that increases bioavailability and/or slows metabolism of the one or more compounds of the present invention) is an inhibitor of at least one isoform of CYP450, such as an inhibitor of CYP1A2, CYP2d6, CYP2C9, CYP2C19 or CYP3A4. In particular embodiments, such agent (e.g., agent that increases bioavailability and/or slows metabolism of the one or more compounds of the present invention) is an inhibitor of CYP3A4 (e.g., nefidipine or ritonavir). In some embodiments, the cell is in a subject. In some embodiments, the subject has been diagnosed with or is predisposed to (e.g., at a risk of developing) a disease or condition that is caused or mediated by elevated cholesterol level (e.g., an elevated cholesterol associated disease, such as atherosclerosis, hypercholesterolemia (e.g., heterozygous familial hypercholesterolemia or homozygous familial hypercholesterolemia), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure).

Other aspects feature the use of at least one compound of the present invention (e.g., such as one or more of compounds 1-52 of Table 1, or a compound of Formula I, II, III, IV, V, or VI) or a pharmaceutically acceptable salt or solvate thereof for the manufacture of a medicament for: (i) lowering cholesterol in a subject or a cell; (ii) binding and/or modulating activity of PCSK9 and/or inducing expression and/or activity of LDLR in a subject or a cell; and/or (iii) treating, reducing one or more symptoms of, delaying the onset of and/or reducing the likelihood of occurrence of a disease or condition that is caused or mediated by elevated cholesterol level (e.g., an elevated cholesterol associated disease, such as atherosclerosis, hypercholesterolemia (e.g., heterozygous familial hypercholesterolemia or homozygous familial hypercholesterolemia), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure) in a subject.

Other aspects feature at least one compound of the present invention (e.g., such as one or more of compounds 1-52 of Table 1, or a compound of Formula I, II, III, IV, V, or VI) or a pharmaceutically acceptable salt or solvate thereof for use in: (i) lowering cholesterol in a subject or a cell; (ii) binding and/or modulating activity of PCSK9 and/or inducing expression and/or activity of LDLR in a subject or a cell; and/or (iii) treating, reducing one or more symptoms of, delaying the onset of and/or reducing the likelihood of occurrence of a disease or condition that is caused or mediated by elevated cholesterol level (e.g., an elevated cholesterol associated disease, such as atherosclerosis, hypercholesterolemia (e.g., heterozygous familial hypercholesterolemia or homozygous familial hypercholesterolemia), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure) in a subject.

In some embodiments of any one of the methods, use, and compounds for use featured herein, the subject is a mammal (e.g., a human).

In some embodiments of any one of the aspects featuring methods, use, and compounds for use featured herein, the disease or condition that is caused or mediated by elevated cholesterol level (e.g., elevated cholesterol associated disease) is atherosclerosis, hypercholesterolemia (e.g., heterozygous familial hypercholesterolemia or homozygous familial hypercholesterolemia), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure. In particular embodiment of any one of the methods, use, and compounds for use featured herein, the disease or condition that is caused or mediated by elevated cholesterol level (e.g., elevated cholesterol associated disease) is atherosclerosis. Alternatively or additionally, the disease or condition that is caused or mediated by elevated cholesterol level (e.g., elevated cholesterol associated disease) is hypercholesterolemia (e.g., heterozygous familial hypercholesterolemia or homozygous familial hypercholesterolemia).

Definitions

It is to be understood that the terminology employed herein is for the purpose of describing particular embodiments and is not intended to be limiting.

The term "acyl," as used herein, represents a hydrogen or an alkyl group, as defined herein that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group. The term "$C_{1-6}$ alkyl" as used herein means saturated monovalent hydrocarbon radicals having straight or branched moieties and containing from 1 to 6 carbon atoms. Examples of such groups include, but are not limited to, methyl, ethyl, propyl, iso-propyl, n-butyl, iso-butyl, and tert-butyl.

The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —$NH_2$) or a substituted amino (i.e., —$N(R^N)_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_{1-6}$ alkyl $C_{6-10}$ aryl, $C_{1-10}$ alkyl $C_{6-10}$ aryl, or $C_{1-20}$ alkyl $C_{6-10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "cyano," as used herein, represents a —CN group.

The terms "carbocyclyl," as used herein, refer to a non-aromatic $C_{3-12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_{1-6}$ alkyl $C_{2-9}$ heteroaryl, $C_{1-10}$ alkyl $C_{2-9}$ heteroaryl, or $C_{1-20}$ alkyl $C_{2-9}$ heteroaryl). In some embodiments, the alkyl and the heteroaryl each can be further substituted with 1, 2, 3, or 4 substituent groups as defined herein for the respective groups.

The term "heterocyclyl," as used herein, denotes a mono- or polycyclic radical having 3 to 12 atoms having at least one ring containing one, two, three, or four ring heteroatoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_{1-6}$ alkyl $C_{2-9}$ heterocyclyl, $C_{1-10}$ alkyl $C_{2-9}$ heterocyclyl, or $C_{1-20}$ alkyl $C_{2-9}$ heterocyclyl). In some embodiments, the alkyl and the heterocyclyl each can be further substituted with 1, 2, 3, or 4 substituent groups as defined herein for the respective groups.

The term "hydroxyl," as used herein, represents an —OH group.

The term "ether," as used herein, represents an —O—$R^{O1}$ group wherein each of these recited $R^{O1}$ groups can be optionally substituted; and wherein each $R^{O1}$ is, independently, alkyl, or aryl.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, a,a-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

The term "solvate," as used herein, means a pharmaceutically acceptable solvate form of a compound of the present invention that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention, less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

A "pharmaceutically acceptable salt" as used herein means a salt that retains the biological effectiveness of the free acids and bases of the specified derivative, containing pharmacologically acceptable anions or cations, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, valerate salts, and cations, such as sodium, potassium, calcium, magnesium, ammonium, and tetraalkylammonium, among others.

The term "therapeutically effective amount," as used herein, means an amount of a compound of the present invention, or a pharmaceutically acceptable salt, solvate or composition thereof, that, when administered to a subject (e.g., a mammal) in need of such treatment, is sufficient to effect treatment, as defined herein.

The term "pharmaceutically acceptable formulation," or "pharmaceutical composition," as used herein, means a combination of a compound of the invention, or a pharmaceutically acceptable salt or solvate thereof, and a carrier, diluent, excipients, and/or adjuvants that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, carriers, or adjuvants, and formed into tablets, capsules, and the like. Examples of excipients, diluents, carriers, and adjuvants that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as keolin and bentonite; lubricants such as talc, calcium and magnesium stearate and solid polyethylene glycols; and also, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol, liposomes and wool fat. Final pharmaceutical forms may be pills, tablets, powders, lozenges, sachets, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional hypocholesterolemic agents. A pharmaceutically acceptable formulation may also include but is not limited to compounds, other than the compounds of Table I, having a structure such that, upon administration to a recipient or patient, a compound of this invention, active metabolite or residue thereof is directly or indirectly provided.

The term "elevated cholesterol associated disease," as used herein, refers to a disease or condition that is caused or mediated by elevated cholesterol level (e.g., cholesterol level higher than that in a reference subject, such as a healthy subject). An elevated cholesterol associated disease can be caused by cellular and/or organ dysfunction stemming from elevated cholesterol level. Examples of elevated cholesterol associated disease include, but are not limited to atherosclerosis, hypercholesterolemia (e.g., heterozygous familial hypercholesterolemia or homozygous familial hypercholesterolemia), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease, and congestive heart failure. One or more elevated cholesterol associated diseases can be treated by one or more compounds, compositions, and methods described herein.

As used herein, the term "elevated cholesterol level" refers to cholesterol level (e.g., cholesterol level in blood) that is higher in a subject (e.g., a human with an elevated cholesterol associated disease) by 5% or more (e.g., between 5-20%, between 5-50%, between 10-50%, between 10-80%, between 20-80%, or between 20-100% (e.g., 5%, 10%, 15%, 20%, 25%, 30%, 40%, 50%, 60%, 70%, 80%, 90%, 95%, 99%, or more)) compared to a healthy control (e.g., a healthy human). Elevated cholesterol level in a subject (e.g., in bloodstream of a subject) can be reduced by one or more compounds, compositions, and methods described herein.

As used herein, the term "hypercholesterolemia" refers to a condition that is caused or mediated by the presence of high levels of cholesterol in the blood. It is an elevated cholesterol associated disease that is characterized by high blood lipids and hyper-lipoproteinemia or elevated levels of lipoproteins in the blood. Familial hypercholesterolemia is the familial or inherited form of hypercholesterolemia, and is characterized by high cholesterol levels, specifically, very high levels of low-density lipoprotein (LDL) in the blood and early cardiovascular disease. Familial hypercholesterolemia is caused by mutation in the gene for the LDL receptor (LDLR), which is involved in passing LDL from the body. However, mutations in other genes (e.g., PCSK9 and the gene for Apolipoprotein B (ApoB)) can also cause inherited high cholesterol. Heterozygous familial hypercholesterolemia is familial hypercholesterolemia that is inherited from one parent, while homozygous familial hypercholesterolemia is familial hypercholesterolemia that is inherited from both parents. Hypercholesterolemia (e.g., familial hypercholesterolemia, such as heterozygous familial hypercholesterolemia and homozygous familial hypercholesterolemia) can be treated by one or more compounds, compositions, and methods described herein.

The term "coronary artery disease," as used herein, includes atherosclerotic plaque prevention, regression, or stabilization, vulnerable plaque prevention, regression, or stabilization, vulnerable plaque area reduction, arterial calcification (e.g., calcific aortic stenosis), increased coronary artery calcium score, dysfunctional vascular reactivity, vasodilation disorders, coronary artery spasm, first myocardial infarction, myocardia re-infarction, ischemic cardiomyopathy, stent restenosis, PTCA restenosis, arterial restenosis, coronary bypass graft restenosis, vascular bypass restenosis, decreased exercise treadmill time, angina pectoris/chest pain, unstable angina pectoris, exertional dyspnea, decreased exercise capacity, ischemia, silent ischemia, increased severity and frequency of ischemic symptoms, and reperfusion after thrombolytic therapy for acute myocardial infarction.

The term "hypertension," as used herein, is selected, but not limited to the group consisting of lipid disorders with hypertension, systolic hypertension, and diastolic hypertension.

The term "peripheral vascular disease," as used herein, is selected, but not limited to the group consisting of peripheral vascular disease and claudication.

The term "diabetes", as used herein, refers to any of a number of diabetogenic states including type I diabetes, type II diabetes, Syndrome X, Metabolic syndrome, lipid disorders associated with insulin resistance, impaired glucose tolerance, non-insulin dependent diabetes, microvascular diabetic complications, reduced nerve conduction velocity, reduced or loss of vision, diabetic retinopathy, increased risk of amputation, decreased kidney function, kidney failure, insulin resistance syndrome, pluri-metabolic syndrome, central adiposity (visceral)(upper body), diabetic dyslipidemia, decreased insulin sensitization, diabetic retinopathy/neuropathy, diabetic nephropathy/micro and macro angiopathy and micro/macro albuminuria, diabetic cardiomyopathy, diabetic gastroparesis, obesity, increased glycosylated hemoglobin (including HbA1 C), impaired glucose control, impaired renal function (e.g., requiring dialysis, or end stage) and impaired hepatic function (e.g., mild, moderate, or severe).

"Metabolic syndrome," also known as "SyndromeX," refers to a common clinical disorder that is characterized by the presence of increased insulin concentration in association with other disorders including visceral obesity, hyperlipidemia, dyslipidemia, hyperglycemia, hypertension, and potentially hyperuricemis and renal dysfunction.

The terms "treat", "treating", and "treatment" refer to any treatment of a disease or condition that is caused or mediated by elevated cholesterol level (e.g., an elevated cholesterol associated disease) in a subject, such as a mammal, particularly a human, and include: (i) preventing the disease or condition from occurring in a subject that may be predisposed to (e.g., at a risk of developing) the condition or reducing the likelihood of occurrence of the disease or condition in a subject that may be predisposed to (e.g., at a risk of developing) the condition, such that the treatment constitutes prophylactic treatment for the pathologic condition; (ii) modulating or inhibiting the disease or condition, i.e., arresting its development; (iii) delaying the onset of the disease or condition; (iv) relieving or reducing the disease or condition, i.e., causing regression of the disease or condition; or (v) relieving, reducing and/or alleviating the disease or condition or the symptoms resulting from the disease or condition, e.g., relieving or reducing an inflammatory response without addressing the underlying disease or condition.

As used herein, the terms "increase," "increasing," "induce" or "inducing" and "decrease," "decreasing," "reduce" or "reducing" refer to modulating resulting in, respectively, greater or lesser amounts, of function, expression level, occurrence, or activity of a metric relative to a reference. For example, subsequent to administration of one or more compounds described herein, cholesterol level may reduce or decrease in a subject by at least 5% or more (e.g., between 5-20%, between 5-50%, between 10-50%, between 10-80%, between 20-80%, or between 20-100% (e.g., 5%, 10%, 15%, 20%, 25%, 30%, 40%, 50%, 60%, 70%, 80%, 90%, 95%, 99%, or more)) relative to cholesterol level prior to administration of the compounds. Also, subsequent to administration of one or more compounds described herein, one or more symptoms of an elevated cholesterol associated disease may reduce or decrease in a subject by at least 5% or more (e.g., between 5-20%, between 5-50%, between 10-50%, between 10-80%, between 20-80%, or between 20-100% (e.g., 5%, 10%, 15%, 20%, 25%, 30%, 40%, 50%, 60%, 70%, 80%, 90%, 95%, 99%, or more)) relative to the symptoms of the disease prior to administration of the compounds. Furthermore, subsequent to administration of one or more compounds described herein, the likelihood or chance of occurrence of an elevated cholesterol associated disease may reduce or decrease in a subject by at least 5% or more (e.g., between 5-20%, between 5-50%, between 10-50%, between 10-80%, between 20-80%, or between 20-100% (e.g., 5%, 10%, 15%, 20%, 25%, 30%, 40%, 50%, 60%, 70%, 80%, 90%, 95%, 99%, or more)) relative to the likelihood or chance of occurrence of the disease in a reference subject (e.g., a subject to whom the compounds has not been administered).Alternatively, subsequent to administration of one or more compounds described herein, PCSK9 activity, expression and/or LDLR expression and/or activity may increase or induce in a subject by at least 5% or more (e.g., between 5-20%, between 5-50%, between 10-50%, between 10-80%, between 20-80%, or between 20-100% (e.g., 5%, 10%, 15%, 20%, 25%, 30%, 40%, 50%, 60%, 70%, 80%, 90%, 95%, 99%, or more)) relative to PCSK9 binding, modulation of PCSK9 activity, LDLR expression and/or LDLR activity prior to administration of the compounds. Generally, the metric is measured subsequent to administration at a time that the administration has had the recited effect, e.g., at least one week, one month, 3 months, or 6 months, after a treatment regimen has begun. The term "reducing" is used interchangeably with the term "decreasing" herein. The term "increasing" is used interchangeably with the term "inducing" herein.

"Delaying the onset," as used herein, refers to delaying or postponing the onset, start or occurrence of a condition relative to a reference. For example, subsequent to administration of one or more compounds described herein, the onset, start, or occurrence of an elevated cholesterol associated disease in a subject may be delayed or postponed by at least 1 month or more (e.g., 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or more) compared to a reference subject (e.g., a control subject to whom the compound has not been administered).

The term "predisposed to," as used herein refers to being at a higher risk, having a higher chance, or having a higher likelihood of developing a condition or disease relative to a reference. For example, a subject predisposed to an elevated cholesterol associated disease may have a higher (e.g., at least 5% or more (e.g., between 5-20%, between 5-50%, between 10-50%, between 10-80%, between 20-80%, or between 20-100% (e.g., 5%, 10%, 15%, 20%, 25%, 30%, 40%, 50%, 60%, 70%, 80%, 90%, 95%, 99%, or more)) risk, chance, or likelihood of developing the elevated cholesterol associated disease compared to a reference (e.g., a subject who is not predisposed to the disease).

The terms "co-administration", "co-administering", "co-administer", "co-administered", or "combination therapy" as used herein, refer to the administration of a combination of at least a first agent and a second agent or two or more agents according to the present invention. Such co-administration can be performed such that two or multiple agents are part of the same composition or part of the same unitary dosage form. Co-administration also includes administering a first agent and a second agent, or more than two agents separately and as part of the same therapeutic regimen. The agents, if administered separately, need not necessarily be administered at essentially the same time, although they can be if so desired. Thus, co-administration includes, for example, administering a first agent and a second agent as separate dosages or dosage forms, but at the same time. Co-administration also includes separate administration at different times and in any order. Co-administration, as used herein, can include administration of more than one compound featured herein. Co-administration, as used herein, can also include administration of one or more of the featured compounds and an additional cholesterol lowering agent.

The terms "compound of the present invention", "compound of the invention", "compound featured herein", or "featured compound" refer to any of the above-mentioned compounds, as well as those in the Examples that follow, and include those generically described or those described as species. These terms also refer to pharmaceutically acceptable salts or solvates of these compounds (e.g., such as one or more of compounds 1-52 of Table 1), or a pharmaceutically acceptable salt, solvate or composition thereof.

The terms "comprising" and "including" as used herein, are used in their open, non-limiting sense.

TABLE 2

| Abbreviation | Meaning |
| --- | --- |
| AcOH | Acetic acid |
| Ar | Aromatic |
| BSA | Bovine serum albumin |
| DMF | Dimethylformamide |
| DNA | Deoxyribonucleic acid |
| EtOH | Ethyl alcohol |
| G | gram |
| HPLC | High pressure liquid chromatography |
| M | Molar |
| MeOH | Methyl alcohol |
| Mg | Milligram |
| Mp | Melting point |
| Min | Minute |
| mL | Milliliter |
| Mmol | Millimole |
| nM | Nanomolar |
| RNA | Ribonucleic acid |
| THF | Tetrahydrofuran |

TABLE 2-continued

Abbreviations Used

| Abbreviation | Meaning |
| --- | --- |
| LDLR | Low density lipoprotein receptor |
| LDL | Low density lipoprotein |
| PCSK9 | Proprotein Convertase Subtilisin-Kexin 9 |

DETAILED DESCRIPTION

Figure 1:
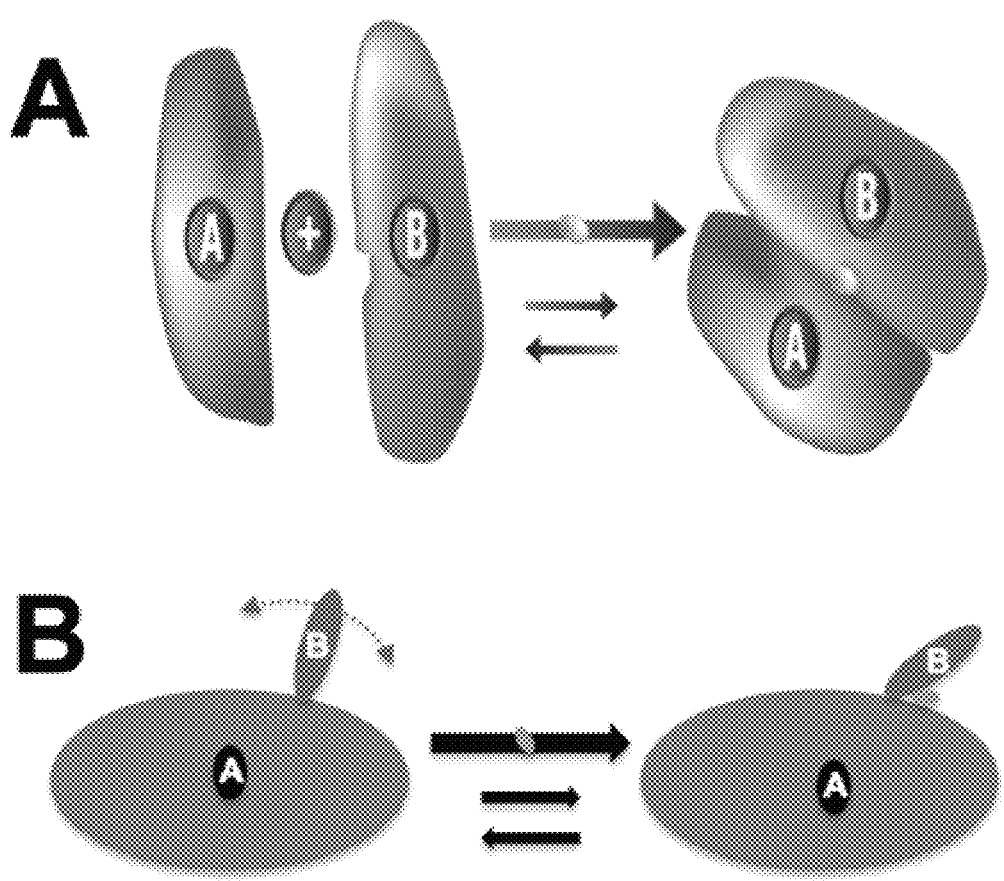
FIG. 1 is a schematic showing an example of how small hyper-interaction modulation (SHIM) affinity for both A and B in a complex can drive the equilibrium and increase stability of the AB complex.

The present disclosure describes compounds 1-52 of Table 1, which are encompassed by Formula I and/or Formula II, III, IV, V, or VI, pharmaceutically acceptable salts or solvates thereof, and pharmaceutical compositions including one or more of the compounds. Also featured herein are methods of synthesis or manufacture of the compounds and use of the compounds in binding to and modulating PCSK9 activity, therefore inducing LDLR expression and activity. Compounds featured herein are useful for lowering total circulating cholesterol, and treating, reducing the symptoms of, reducing the likelihood of occurrence of, delaying the onset of, or delaying the progression of diseases that are associated with elevated cholesterol.

Biochemical data showed that the surface of PCSK9 catalytic domain together with its released N-terminus directly interacts with the first extracellular epidermal growth factor-like repeat (EGF-A) of LDLR, and that the affinity of this interaction greatly increases at acidic pH (Kwon et al., *Proc Natl Acad Sci USA*. 2008; 105(6):1820-1825; Lo Surdo et al., *EMBO reports*. 2011; 12(12):1300-1305). PCSK9-D374Y GOF mutant has a markedly increased affinity to LDLR by allowing a hydrogen bond to form at neutral pH with H306 of the LDLR EGF-A domain, resulting in an extremely severe FH phenotype. Interestingly, removal of the N-terminal acid stretch (aa31-53) of PCSK9 prosegment also strongly increases its binding to LDLR. In addition, it was shown that PCSK9 residue L108 makes van der Waals interactions with the LDLR β-propeller domain, which could be potentiated in L108R, S127R or D129G prosegment PCSK9GOF mutations. Patients harboring the PCSK9 prosegment R46L LOF mutation had-50% reduction in incidence of coronary events owing to a lifelong reduction in LDL-cholesterol of only 15%. It has been found that the R46L variant does not affect PCSK9 endocytosis but has a 2-fold weaker affinity for LDLR resulting in a slight reduction of its capacity to induce LDLR degradation. Loss- or gain-of-function mutations in PCSK9 prosegment (e.g., R46L, S127R, D129G) or CTD (e.g., R496W and H553R), which are not primarily involved in LDLR EGF-A binding, show that those domains also participate in the regulation of PCSK9-induced LDLR degradation by a mechanism for which we possess very little information.

Independently of its catalytic activity (McNutt et al., *J Biol Chem.* 2007; 282(29):20799-20803) PCSK9 binds to LDLR and prevents its cell surface recycling by rerouting the receptor to late endocytic compartments for degradation. So far, two prevailing mechanisms have been proposed to explain the PCSK9-induced LDLR degradation both relying on the essential role of the PCSK9 CTD in the process. Firstly, once in acidic compartments, the affinity of PCSK9 catalytic domain for LDLR EGF-A is greatly increased and could allow interaction of the CTD with the LDLR ligand-binding domain, creating a conformational change in LDLR that would induce its shedding by γ-secretase and its degradation in lysosomes. Secondly, it has been proposed that a putative transmembrane protein would connect PCSK9 via its CTD to cytosolic adaptors in order to target the PCSK9-LDLR complex to lysosomes. Although the exact role of PCSK9 CTD requires more investigations, it has been shown that Annexin A2 or a monoclonal antibody that specifically bind to the CTD both inhibited the PCSK9-induced LDLR degradation (Mayer et al., *J Biol Chem.* 2008; 283(46):31791-31801; Seidah et al., *PLoS One.* 2012; 7(7):e41865; Schiele et al., *J Mol Biol.* 2014; 426(4):843-852).

The increasing elucidation of cellular molecular pathways identifies many defective protein interactions in human diseases, and provides a rationale for pharmacological interference. However, modulation of protein interactions with small molecules remains a most challenging approach for drug discovery. Most current strategies are based on competitive approaches in which inhibitors are intended to block proteins from establishing contacts with their target. These approaches have major weaknesses: (1) macromolecular interactions often involve large hydrophobic interfaces, for which pharmaceutically acceptable compounds cannot effectively compete for such a binding surface; (2) drug targets often belong to families of homologous regulators (such as protein kinases) and so are difficult to block selectively; (3) unbound proteins often lack 'hotspots' for binding small molecules with sufficient affinity and specificity. There are thus very few examples of successful design of inhibitors of a protein-protein interaction and there is clearly a need to develop of new paradigm for structure-based drug design. In the present invention, we used our structure-based algorithm for enhancement rather that inhibition of protein-protein interactions, so call small hyper-interaction modulation (SHIM) compounds. SHIMs bind at the inter-molecular space formed between two interacting molecules making molecular contacts with both molecules and can interfere with the normal function of the complex (FIG. 1). Similar types of complex-binding modulation effects have been observed for some natural compounds that bind at protein-protein or protein-DNA inter-molecular spaces with many well-known examples some of which are very widely used drugs such as FK506, rapamycin, topotecan and many others. In general, A and B are separate proteins that can form a complex or can be intramolecular interactions that undergo conformational transitions leading to changes in relative orientation between A and B as part of regulating the biological activity of a given protein. As an example, B could be a flexible loop that can move relative to the conformationally more stable part of the same molecule (A). In that case, binding of SHIMs can stabilize loop B by restricting its flexibility and preventing conformational transitions relative to A (FIG. 1). In the present invention, we performed virtual high throughput screening using SHIM algorithm to identify compounds in the ZINC library (http://zinc.docking.org/) binding to the inter-molecular cavities of complex-forming molecules to identify drug candidate compounds targeting PCSK9, based on structural data and human natural mutations identified in hyper- or hypocholesterolemic patients suggesting hot spots; herein defined as flexible loops ("SHIM loops").

Compounds

Featured in the disclosure are "hit" SHIM's compounds identified within the ZINC library (a database of commercially available compounds for virtual screening; Sterling and Irwin, *J. Chem. Inf. Model* 2015; Irwin, Sterling, Mysinger, Bolstad, and Coleman, *J. Chem. Inf. Model* 2012, Irwin and Soichet, *J. Chem. Inf. Model* 45:177-82, 2005) as interacting with PCSK9 SHIM's loops (e.g., compounds 1-52 of Table 1), or pharmaceutically acceptable salts or solvates thereof.

The compounds of Table 1 are encompassed by Formula I, II, III, IV, V, and/or IV below:

(a) formula (I):

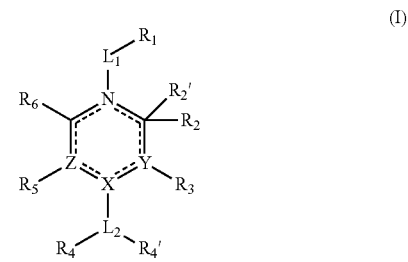

wherein:
each of Z, X, and Y is independently N, C, CH, or CH$_2$;
=== indicates an optional single or double bond;
L$_1$ is absent,

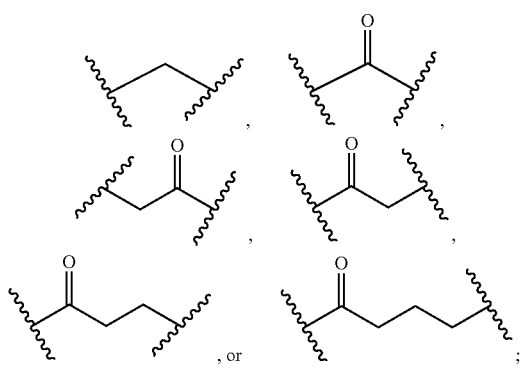

$L_2$ is absent,

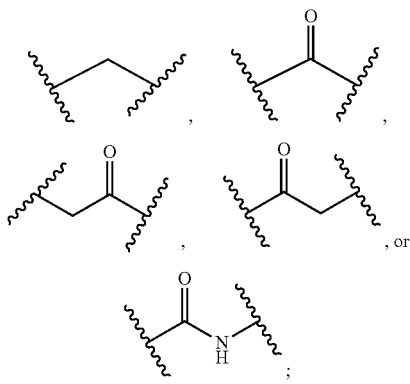

$R_1$ is optionally H, optionally substituted $C_1$-$C_4$ alkyl, optionally substituted $C_{2-4}$ acyl, optionally substituted $C_{3-5}$ heterocyclyl, optionally substituted $C_{2-10}$ heteroaryl, or optionally substituted $C_{6-10}$ aryl;

$R_2$ is optionally H,

optionally substituted $C_{1-4}$ alkyl, optionally substituted $C_4$ heteroalkyl, optionally substituted $C_7$ heterocyclylalkyl, optionally substituted $C_{4-5}$ heterocyclyl, optionally substituted $C_{5-9}$ heteroaryl, optionally substituted $C_4$ alkenyl, or optionally substituted $C_6$ aryl;

$R_2'$ is optionally absent, H, or optionally substituted $C_1$ alkyl;

$R_3$ is absent, H,

optionally substituted $C_{1-4}$ alkyl, optionally substituted $C_1$ acyl, optionally substituted $C_1$ heteroalkyl, optionally substituted $C_3$ heterocycylalkyl, optionally substituted heterocyclyl, optionally substituted $C_3$ heteroarylalkyl, optionally substituted $C_7$ heteroaryl, optionally substituted $C_6$ aryl, optionally substituted $C_{2-3}$ heteroalkenyl, optionally substituted $C_7$ alkenyl, or optionally substituted amino;

$R_4$ is absent, H, optionally substituted alkyl, optionally substituted $C_6$ arylalkyl, optionally substituted amino, optionally substituted $C_8$ alkyenyl, optionally substituted $C_{4-6}$ heterocyclyl, optionally substituted $C_7$ heteroaryl, optionally substituted $C_{10}$ ether; optionally substituted $C_6$ aryl;

$R_4'$ is absent, H, optionally substituted $C_8$ arylalkyl, optionally substituted $C_6$ ether, optionally substituted $C_8$ alkyenyl;

$R_5$ is absent, H, optionally substituted $C_{4-7}$ alkenyl, optionally substituted $C_{11}$ arylalkyl, or optionally substituted $C_3$ heteroalkenyl;

$R_6$ is H,

optionally substituted $C_6$ aryl, optionally substituted $C_5$ heteroacyl, optionally substituted amino, optionally substituted $C_5$ heterocyclylalkyl, or optionally substituted $C_4$ alkyenyl;

$R_1$ and $R_2$, together with the atoms to which each is attached, may be combined to form an optionally substituted $C_6$ aryl, or $C_5$ heterocyclyl;

$R_2$ and $R_2'$, together with the atom to which each is attached, may be combined to form an optionally substituted $C_5$ heterocyclyl;

$R_2$ and $R_3$, together with the atoms to which each is attached, may be combined to form an optionally substituted $C_6$ cycloalkyl;

$R_3$ and $R_4$, together with the atoms to which each is attached, may be combined to form an optionally substituted $C_4$ heteroaryl, or an optionally substituted $C_6$ aryl;

$R_4$ and $R_4'$, together with the atom to which each is attached, may be combined to form an optionally substituted $C_9$ aryl or optionally substituted $C_{8-9}$ heteroaryl;

$R_4$ and $R_5$, together with the atom to which each is attached, may be combined to form an optionally substituted $C_{3-4}$ heteroaryl, or an optionally substituted $C_6$ aryl; and $R_5$ and $R_6$, together with the atoms to which each is attached, may be combined to form an optionally substituted $C_6$ aryl;

(b) formula II:

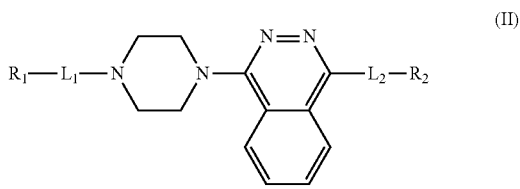

wherein:
$L_1$ is

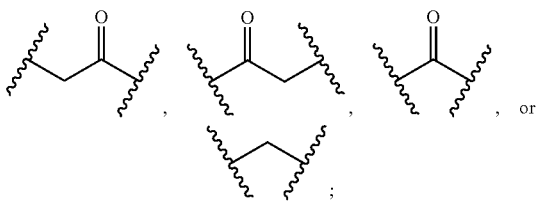

$L_2$ is absent or

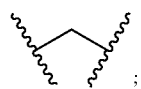

$R_1$ is an optionally substituted $C_{4-7}$ heteroaryl, optionally substituted $C_{4-5}$ heterocyclyl,

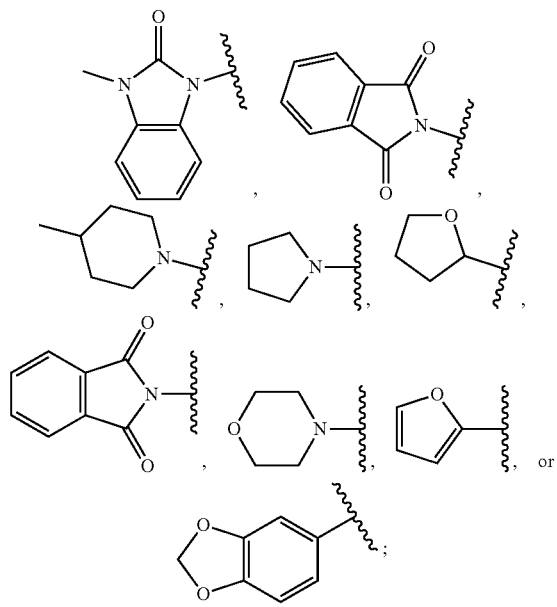

and

R₂ is an optionally substituted $C_6$ aryl, optionally substituted $C_5$ heteroaryl,

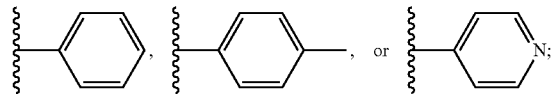

(c) formula III:

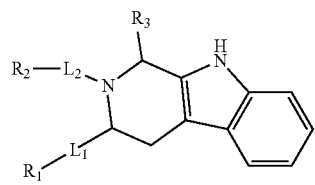

(III)

wherein:

L₁ is

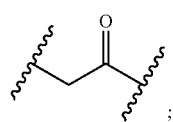

L₂ is

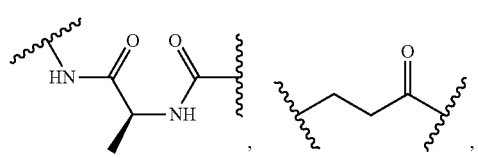

-continued

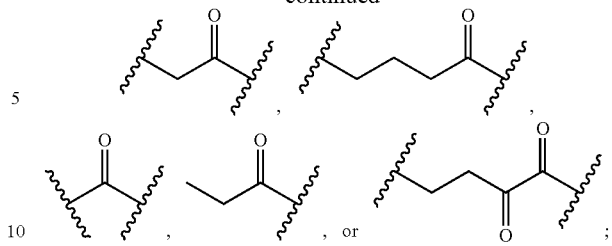

R₁ is an optionally substituted $C_8$ heteroaryl, or

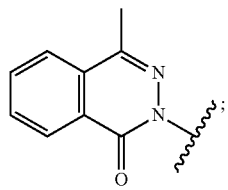 [SMILES: *n1nc(C)c2ccccc2c1=O]

R2 is an optionally substituted $C_5$ carbocyclyl, optionally substituted $C_5$ heterocyclyl, optionally substituted $C_6$ aryl, optionally substituted $C_{3-9}$ heteroaryl,

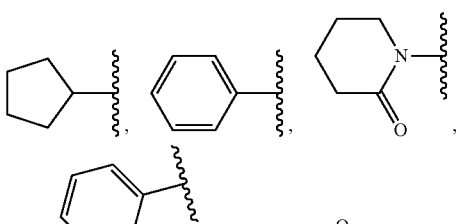

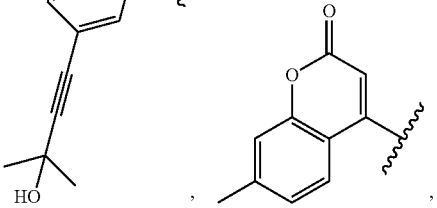

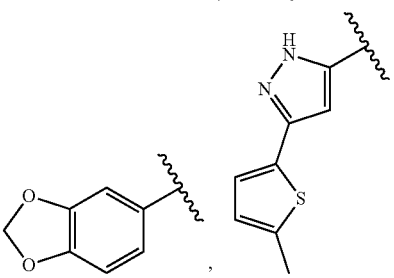

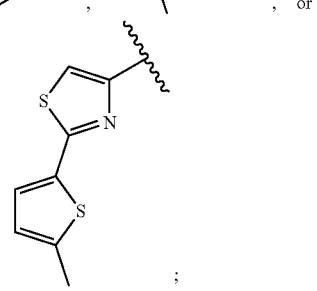

R₃ is an optionally substituted $C_1$ alkyl, optionally substituted $C_5$ heteroaryl,

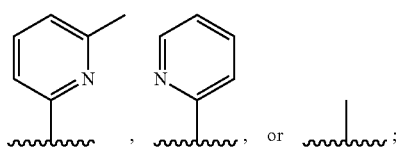, or ;

and

R₂ and R₃, together with the atoms to which each is attached, may be combined to form an optionally substituted C₈ aryl;

(d) formula IV:

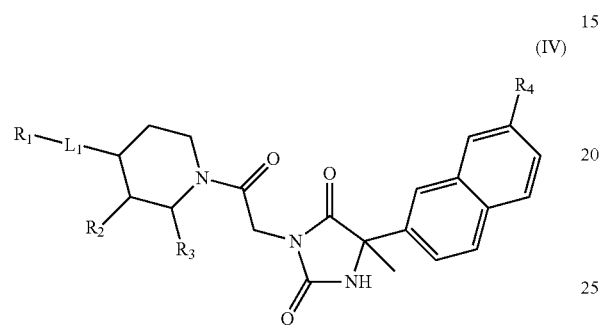

(IV)

wherein:

L₁ is

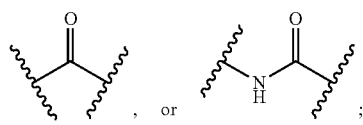

R₁ is an optionally substituted C₇ heterocyclyl, optionally substituted C₇ heteroaryl, optionally substituted C₆ aryl,

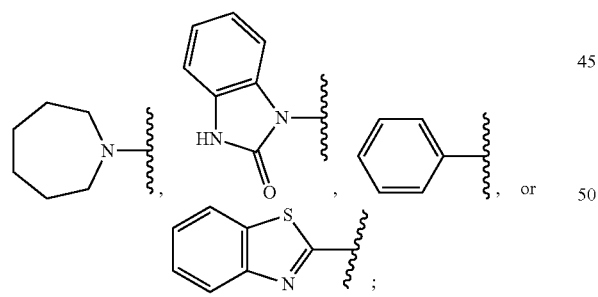

Each or R₂ and R₃ is an optionally substituted C₇ heteroaryl, optionally substituted C₂ alkyl,

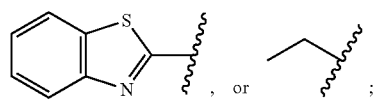

R₂ and R₃, together with the atoms to which each is attached, may be combined to form an optionally substituted C₆ cycloalkyl; and R₄ is absent or

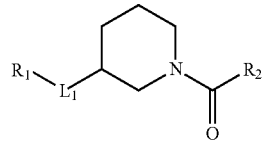;

(e) formula V:

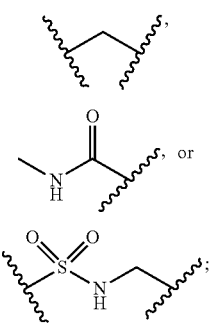

(V)

wherein:

L₁ is

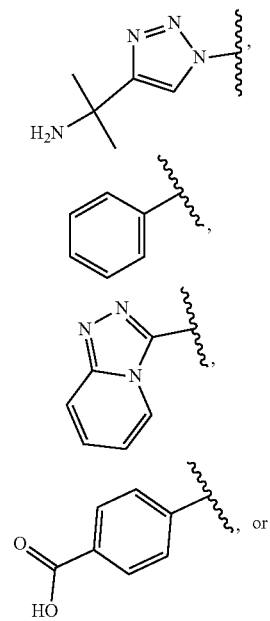

R₁ is an optionally substituted C₆ aryl, an optionally substituted C₂-C₆ heterocyclyl,

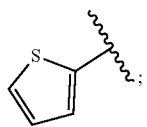
and
R₂ is an optionally substituted C₆ aryl, optionally substituted C₉ heterocyclyl,
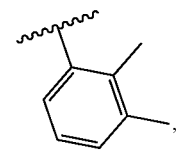
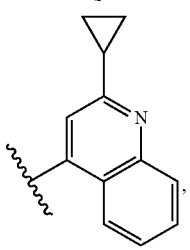
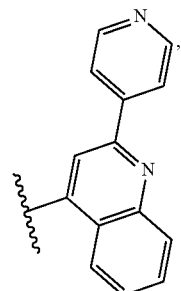
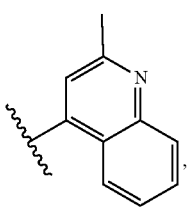
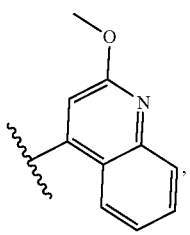
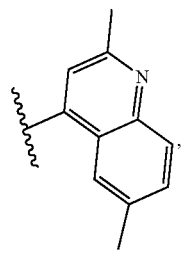
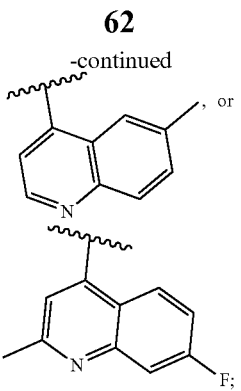
(f) formula VI:
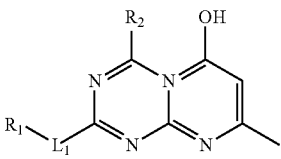
(VI)
wherein:
L₁ is
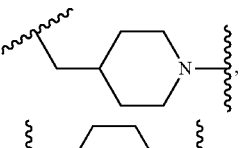
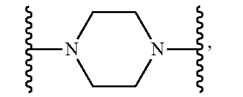
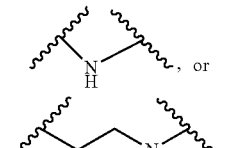
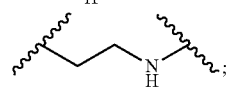
R₁ is an optionally substituted C₆ aryl, optionally substituted C₈ heteroaryl,
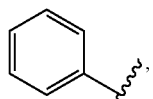
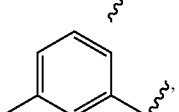
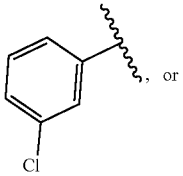

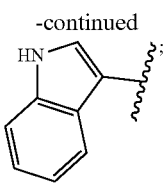

and

R₂ is an optionally substituted $C_5$ heteroaryl, an optionally substituted $C_6$ aryl,

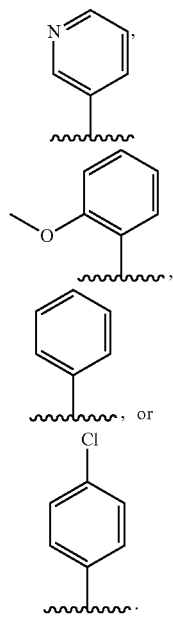

Pharmaceutical Composition

Pharmaceutical compositions contemplated herein include at least one compound of the present invention, and pharmaceutically acceptable salts, solvate or composition thereof, with a pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, liposomes and wool fat.

Compounds of the present invention that are basic may be prepared as a salt using suitable methods known in the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or methanesulfonic acid; and the like.

It is understood by those skilled in the art that the compounds of the present invention, salts, or solvates thereof may exist in different crystal or polymorphic forms that are within the scope of the present invention and specified formulas.

Basic compounds of the present invention can form a variety of salts with various inorganic and organic acids. Although such salts must be pharmaceutically acceptable for administration to animals, it is common practice to first isolate the compound of the present invention as a pharmaceutically unacceptable salt and then convert to a free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol.

Compounds of the present invention that are acidic may be prepared as a salt using suitable methods known in the art, including treatment of the free acid with an inorganic or organic base, such as an amine (primary, secondary, or tertiary); an alkali metal or alkaline earth metal hydroxide; or the like. Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

Acidic compounds of the present invention can form base salts with various pharmacologically acceptable cations. Examples of such salts include the alkali metal or alkaline-earth metal salts and particularly, the sodium and potassium salts, which can be prepared using conventional techniques. The chemical bases suitable as reagents in preparing the pharmaceutically acceptable base salts of this invention are those that form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

To treat or reduce the likelihood of occurrence of diseases or conditions caused or mediated by elevated cholesterol (e.g., elevated cholesterol associated diseases), a pharmaceutical composition including at least one of the compounds of the present invention is administered in a pharmaceutically acceptable formulation prepared by combining a therapeutically effective amount of the compound with one or more pharmaceutically suitable carriers including diluents, excipients and auxiliaries that facilitate processing of the active compounds into a pharmaceutically acceptable formulation. Carriers employed may be either solid or liquid. Exemplary solid carriers are lactose, sucrose, talc, gelatin, agar, pectin, acacia, magnesium stearate, stearic acid, and the like. Exemplary liquid carriers are syrup, peanut oil, olive oil, water, and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate, or the like. Further additives or excipients may be added to achieve the desired formulation properties. For example, a bioavailability enhancer, such: as Labrasol®, Gelucire®, or the like, or formulators, such as CHIC (carboxymethylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80 (polyoxyethylene(20)sorbitan monooleate), glycerin, and the like in concentrations ranging from 0-60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Pharmaceutical preparations for oral use can be obtained using a solid excipient in an admixture with the active ingredient (agent), optionally grinding the resulting mixture, and processing the mixture of granules after adding suitable auxiliaries, if desired, to obtain tablets or dragee cores. Suitable excipients include: fillers, such as sugars, including lactose, sucrose, mannitol, or sorbitol; and cellulose preparations, for example, cornstarch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

The pharmaceutical compositions, comprising the compounds of the present invention may also contain suitable solid- or gel-phase carriers or excipients. These carriers and excipients may provide marked improvement in the bioavailability of poorly soluble drugs. Examples of such carriers or excipients include calcium carbonate, calcium, phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol®, and the like may be used. Further, the pharmaceutical composition may be incorporated into a skin patch for delivery of the drug directly onto the skin.

The compounds of this invention may be modified by appending appropriate functionalities to enhance selective biological properties. Such modifications are known in the art and include those that increase biological penetration into a given biological system (e.g., blood, lymphatic system, central nervous system), increase oral bioavailability, increase solubility to allow administration by injection, alter metabolism, or alter rate of excretion (*Pharmacokinetic Optimization in Drug Research*, Testa, B. et al., 2001, Wiley-VCH, VCHA).

The pharmaceutical compositions of this invention may be administered orally, parenterally, by inhalation spray, topically, rectally, nasally, buccally, vaginally, or via an implanted reservoir, and are preferably administered orally or parenterally. The pharmaceutical compositions of this invention may contain any conventional non-toxic pharmaceutically acceptable carriers, adjuvants or vehicles. The term "parenteral" or "parenterally" as used herein includes sub-cutaneous, intra-cutaneous, intra-venous, intra-muscular, intra-articular, intra-synovial, intra-sternal, intra-thecal, intra-lesional and intracranial injection or infusion techniques.

Pharmaceutical compositions of the invention may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solutions. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions.

Pharmaceutical compositions of the invention may be orally administered in any orally acceptable dosage form including, but not limited to, capsules, tablets, and aqueous suspension and solutions. In the case of tablets for oral administration, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening, flavoring, and/or coloring agents may be added.

Pharmaceutical compositions of the invention may also be administered in the form of suppositories for rectal administration. These compositions can be prepared by mixing a compound of this invention with a suitable non-irritating excipient that is solid at room temperature but liquid at the rectal temperature and therefore will melt in the rectum to release the active components. Such materials include, but are not limited to, cocoa butter, beeswax, and polyethylene glycols.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage

Methods of treatment, their dosage levels and requirements featured herein may be selected by those of ordinary skill in the art from available methods and techniques.

It will be appreciated that the actual dosages of the compounds of this invention (e.g., such as one or more of compounds 1-52 of Table 1 or a compound of Formula I, II, III, IV, V, or VI) or a pharmaceutically acceptable salt or solvate thereof will vary according to the particular compound being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals, preferably between 0.01 and about 25 mg/kg body weight per day, and more preferably between about 0.5 and about 25 mg/kg body weight per day of the active ingredient compound are useful in the prevention and treatment of elevated cholesterol, including high circulating LDL.

Furthermore, the pharmaceutically acceptable formulations of the present invention may contain a compound of the present invention, or a pharmaceutically acceptable salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 mg to about 500 mg, or from about 100 mg to about 500 mg. Additionally, the pharmaceutically acceptable formulations of the present invention may contain a compound of the present invention, or a pharmaceutically acceptable salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

Typically, the pharmaceutical compositions of this invention will be administered from about 1 to about 5 times per day, or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 75% active compound (w/w). Preferably, such preparations contain from about 20% to about 50% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been reduced or alleviated to the desired level, treatment should cease, at least in principle. Patients may, however, require intermittent treatment on a long-term basis, upon any recurrence of disease symptoms, especially for high levels of cholesterol.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the disease (e.g., elevated cholesterol associated disease), the patient's disposition to the disease and the judgment of the treating physician.

With respect to the compounds of the present invention, the particular pharmaceutical formulation, the dosage, and the number of doses given per day to a mammal requiring such treatment are all choices within the knowledge of one of ordinary skill in the art and can be determined without undue experimentation.

Treatment

The compounds of this invention (e.g., such as one or more of compounds 1-52 of Table 1 or a compound of Formula I, II, III, IV, V, or VI) or a pharmaceutically acceptable salt or solvate thereof are also useful as commercial reagents that effectively lower circulating cholesterol. As commercial reagent, the compounds of this invention, and their derivatives, may be derivatized to bind to a stable resin as a tethered substrate for affinity chromatography applications. These and other uses that characterize commercial cholesterol lowering agents will be evident to those of ordinary skill in the art.

The compounds of the present invention can be used alone (monotherapy) or administered in combination with one or more additional cholesterol lowering agents for the treatment of high blood lipids associated diseases, such as diseases or conditions that are caused or mediated by elevated cholesterol level (e.g., elevated cholesterol associated diseases), including, but not limited to, atherosclerosis, hypercholesterolemia (heterozygous and homozygous familial hypercholesterolemia included), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure in a subject (e.g., a mammal, such as a human).

The compounds of this invention ((e.g., such as one or more of compounds 1-52 of Table 1 or a compound of Formula I, II, III, IV, V, or VI) or a pharmaceutically acceptable salt or solvate thereof may be administered in combination with other cholesterol lowering agents (e.g., additional cholesterol lowering agents) that target other steps in the cholesterol metabolism. These agents include, but are not limited to: a lipase inhibitor, an 3-hydroxy-3-methyl-glutaryl-coenzyme A (HMG CoA) reductase inhibitor, an HMG CoA synthase inhibitor, an ATP citrate lyase inhibitor, a LDLR degradation inhibitor, a cholesteryl ester transfer protein (CETP) inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a microsomal triglyceride transfer protein (MTP) inhibitor, an Apolipoprotein B (ApoB) secretion inhibitor, a proprotein convertase subtilisin kexin type 9 (PCSK9) gene expression inhibitor, an anti-PCSK9 antibody, a PCSK9 mRNA silencer, a fibrate, niacin or a combination of niacin with a statin, an ion-exchange resin, an acyl-coenzyme A:cholesterol acyltransferase (ACAT) inhibitor and a bile acid sequestrant, an HMG-CoA reductase gene expression inhibitor, and an HMG-CoA synthase gene expression inhibitor.

Combination therapies according to this invention may exert an additive or combined effect on reduction of elevated cholesterol because each therapeutic agent of the combination acts on a different site of cholesterol metabolism. The use of such combination therapies may also advantageously enable a reduction in the dosage of each cholesterol-lowering agent, compared to administration of either agent alone as a monotherapy, while providing an equivalent or better therapeutic or prophylactic effect. Administration of lower doses of each therapeutic agent often reduces or even eliminates side effects or toxicity relative to monotherapy. Furthermore, combination therapies may reduce the potential for the development of undesired side effects to the agents administered compared to monotherapy.

Administration of the compounds of this invention (e.g., such as one or more of compounds 1-52 of Table 1 or a compound of Formula I, II, III, IV, V, or VI) or a pharmaceutically acceptable salt or solvate thereof in combination therapies with other agents to patients may be sequential or concurrent. One or more cholesterol lowering agents (e.g., one or more additional cholesterol lowering agents) may be administered to a subject (e.g., a mammal, such as a human (e.g., a human patient)) prior to, concurrent with, or following the administration of one or more compounds of compounds 1-52 (Table 1) or a compound of Formula I, II, III, IV, V, or VI featured herein. Furthermore, pharmaceutical or prophylactic compositions of this invention may include a combination of cholesterol lowering agent of this invention ((e.g., such as one or more of compounds 1-52 of Table 1 or a compound of Formula I, II, III, IV, V, or VI, featured herein) and another therapeutic or prophylactic agent, such as one or more additional cholesterol lowering agents.

In some embodiments, a subject (e.g., a mammal, such as a human (e.g., a human patient)) may have been treated with one or more additional cholesterol lowering agents prior to administering one or more compounds of the present invention (e.g., such as one or more of compounds 1-52 of Table 1 or a compound of Formula I, II, III, IV, V, or VI) or a pharmaceutically acceptable salt or solvate thereof. In some embodiments, treatment (e.g., prior treatment) with one or more additional cholesterol lowering agents may not effectively lower cholesterol level in the subject.

Some embodiments of the current disclosure describe methods of docking, binding, modulating PCSK9 level and/or activity and therefore inducing LDLR expression and/or its activity in a cell (e.g., a hepatic cell), such as a cell in a subject (e.g., a hepatic cell in a subject) by contacting the cell with an effective amount of at least one compound of the present invention (e.g., such as one or more of compounds 1-52 of Table 1 or a compound of Formula I, II, III, IV, V, or VI) or a pharmaceutically acceptable salt or solvate thereof. Such methods may further include contacting the cell with one or more additional cholesterol lowering agents (e.g., one or more of a lipase inhibitor, an HMG CoA reductase inhibitor, an HMG CoA synthase inhibitor, an ATP citrate lyase inhibitor, a LDLR degradation inhibitor, a CETP inhibitor, a bile acid absorption inhibitor, a cholesterol absorption inhibitor, a cholesterol synthesis inhibitor, a squalene synthetase inhibitor, a squalene epoxidase or cyclase inhibitor or a combination of both, a MTP inhibitor, an ApoB secretion inhibitor, a PCSK9 gene expression inhibitor, an anti-PCSK9 antibody, a PCSK9 mRNA silencer, a fibrate, a niacin or a combination of niacin with a statin, an ion-exchange resin, an ACAT inhibitor and a bile acid sequestrant, an HMG-CoA reductase gene expression inhibitor, or an HMG-CoA synthase gene expression inhibitor).

Examples of cholesterol lowering agents useful for treating elevated cholesterol, suitable for combination therapies with the compounds of this invention (e.g., such as one or more of compounds 1-52 of Table 1 or a compound of Formula I, II, III, IV, V, or VI), and/or suitable for treating subjects (e.g., mammals, such as humans (e.g., human patients) prior to administration of compounds of this invention are listed in Table 3 below.

TABLE 3

Cholesterol Lowering Agents

| Drug Type | Generic name (brand name) | Indication |
|---|---|---|
| De novo cholesterol synthesis inhibitors (statins or HMG-CoA reductase inhibitors) | Atorvastatin (Lipitor ®), Fluvastatin (Lescol ®, Lescol ® XL), Lovastatin (Mevacor ®, Altoprev ®), Pravastatin (Pravachol ®), Rosuvastatin (Crestor ®), Simvastatin (Zocor ®), Pitavastatin (Livalo ®) | For management as an adjunct to diet to reduce elevated total cholesterol (total-C), LDL cholesterol (LDL-C), Apo B, and TG levels in patients with primary hypercholesterolemia and mixed dyslipidemia. For primary prevention of coronary heart disease and to slow progression of coronary atherosclerosis in patients with coronary heart disease. |
| Inhibitors of intestinal cholesterol absorption (NPC1L1 inhibitors) | Ezetimibe (Zetia ®), Ezetimibe + simvastatin (Vytorin ®) | For use as adjunctive therapy to diet for the reduction of elevated total-C, LDL-C, and Apo B in patients with primary (heterozygous familial and non-familial) hypercholesterolemia |
| PPAR agonists (Fibrates) | Gemfibrozil (Lopid ®), Fenfibrate (Antara ®, Lofibra ®, Tricor ®), Clofibrate (Atromid ®) | For the treatment of primary hyperlipidaemia types IIa, IIb, III, IV and V (Fredrickson classification) corresponding to groups I, II and III of the European Atherosclerosis Society guidelines - when diet alone or improvements in lifestyle such as increased exercise or weight reduction do not lead to an adequate response. Also for the treatment of secondary hyperlipidaemias, e.g., severe hypertriglyceridemias, when sufficient |

TABLE 3-continued

Cholesterol Lowering Agents

| Drug Type | Generic name (brand name) | Indication |
| --- | --- | --- |
| | | improvement does not occur after correction of the underlying disorder (e.g., diabetes mellitus). |
| Bile sequestrants (resins) | Cholestyramine (Questran ®, Prevalite ®), Colestipol (Colestid ®, Flavored Colestid), Colesevelam(Welchol ®) | Indicated as adjunctive therapy to diet for the reduction of elevated serum cholesterol in patients with primary hypercholesterolemia (elevated LDL-C) who do not respond adequately to diet. Also for the relief of pruritus associated with partial biliary obstruction. |
| PCSK9 inhibitors | (i) Monoclonal antibodies: Alirocumab (Praluent ®), and Evolocumab (Repatha ®) (ii) Gene silencers: ALN-PCSsc (Inclisiran) (iii) Vaccines: AT04A | Indicated as an adjunct to diet and maximally tolerated statin therapy in adults who require additional LDL-C lowering due to heterozygous familial hypercholesterolemia or clinical atherosclerotic cardiovascular disease |
| MTP inhibitors | Lomitapide (Juxtapid ®) | Used in homozygous familial hypercholesterolemia patients to reduce LDL-C, total-C, Apo B, and non- high-density lipoprotein cholesterol (non-HDL-C). |
| ApoB antisense oligonucleotides | Mipomersen (Kynamro ®) | Used in patients with homozygous familial hypercholesterolemia as an adjunct to diet and other lipid-lowering medications. |

Furthermore, compounds of the present invention (e.g., such as one or more of compounds 1-52 of Table 1 or a compound of Formula I, II, II, IV, V, or VI) or a pharmaceutically acceptable salt or solvate thereof may be administered in combination with an additional agent or pharmaceutical composition that increases the bioavailability or slows the metabolism of the compounds. Agents or pharmaceutical compositions that may increase the bioavailability or slow the metabolism of the compounds featured herein include inhibitors of at least one isoform of the cytochrome P450 (CYP450) enzymes, preferably inhibitors of CYP1A2, CYP2d6, CYP2C9, CYP2C19, and CYP3A4. Suitable agents that may be used to inhibit CYP3A4 include, but are not limited to, nefidipine and ritonavir. Such combinations may be administered such that a compound or compounds of the present invention are present in a single formulation or in the form of separate formulations that may be administered sequentially with an appropriate period of time in between or simultaneously. The choice of whether to include the compound or compounds of the present invention in the same formulation as the additional agent or agents is within the knowledge of one of ordinary skill in the art.

Some embodiments of the current disclosure describe methods of docking, binding, modulating PCSK9 level and/or activity and therefore inducing LDLR expression and/or its activity in a cell (e.g., a hepatic cell), such as a cell in a subject (e.g., a hepatic cell in a subject) by contacting the cell with an effective amount of at least one compound of the present invention (e.g., such as one or more of compounds 1-52 of Table 1 or a compound of Formula I, II, III, IV, V, or VI) or a pharmaceutically acceptable salt or solvate thereof. Such methods may further include contacting the cell with an additional agent or pharmaceutical composition that increases the bioavailability or slows the metabolism of the compounds. Agents or pharmaceutical compositions that may increase the bioavailability or slow the metabolism of the compounds featured herein include inhibitors of at least one isoform of CYP450 enzymes, preferably inhibitors of CYP1A2, CYP2d6, CYP2C9, CYP2C19 and CYP3A4. Suitable agents that may be used to inhibit CYP3A4 include, but are not limited to, nefidipine and ritonavir.

Therapeutic Effects

Featured herein are compositions and methods for reducing cholesterol level (e.g., cholesterol level in blood) in a subject (e.g., a human, such as a human with an elevated cholesterol associated disease) in need thereof by administering to the subject one or more compounds of this invention ((e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds, Table 3). In certain embodiments, the subject may have elevated cholesterol level, such as cholesterol level (e.g., cholesterol level in blood) that is higher by 5% or more (e.g., between 5-20%, between 5-50%, between 10-50%, between 10-80%, between 20-80%, or between 20-100% (e.g., 5%, 10%, 15%, 20%, 25%, 30%, 40%, 50%, 60%, 70%, 80%, 90%, 95%, 99%, or more)) compared to a healthy control (e.g., a healthy human).One or more compounds of the invention, whether used in monotherapy or in combination therapy, can reduce cholesterol level (e.g., cholesterol level in blood, such as elevated cholesterol level in blood) in a subject (e.g., a subject with an elevated cholesterol associated disease) by at least 5% or more (e.g., between 5-20%, between 5-50%, between 10-50%, between 10-80%, between 20-80%, or between 20-100%) relative to cholesterol level prior to administration of the compounds, or relative to cholesterol level in a reference subject to whom the compounds have not been administered (e.g., a subject with the elevated cholesterol associated disease to whom the compounds have not been administered). In some embodiments, one or more compounds of the invention, whether used in monotherapy or in combination therapy, can reduce cholesterol level in a subject (e.g., a subject with an elevated cholesterol associated disease) by at least 5%, 10%, 15%, 20%, 25%, 30%, 40%, 50%, 60%, 70%, 80%, 90%, 95%, 99%, or more relative to cholesterol level prior to administration of the compounds, or relative to cholesterol level in a reference subject to whom the compounds have not been administered (e.g., a subject with the elevated cholesterol associated disease to whom the compound have not been administered).

Also featured herein are compositions and methods for binding to and/or modulating PCSK9 activity therefore inducing LDLR expression in a cell, such as a cell in a subject (e.g., a human, such as a human with an elevated cholesterol associated disease) or a cell in a culture (e.g., a culture generated from a human (e.g., a human with an elevated cholesterol associated) sample, or a repository of human sample) by contacting the cell with one or more compounds of this invention (e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds). One or more compounds of the invention, whether used in monotherapy or in combination therapy, can induce LDLR expression (e.g., mRNA and/or protein expression) in a cell by at least 5% or more (e.g., between 5-20%, between 5-50%, between 10-50%, between 10-80%, between 20-80%, or between 20-100%) relative to LDLR expression prior to contacting with the compounds, or relative to LDLR expression in a reference cell, such as a control cell that has not been contacted with the compounds. In some embodiments, one or more compounds of the invention, whether used in monotherapy or in combination therapy, can induce LDLR expression in a cell by at least 5%, 10%, 15%, 20%, 25%, 30%, 40%, 50%, 60%, 70%, 80%, 90%, 95%, 99%, or more relative to LDLR expression prior to contacting with the compounds, or relative to LDLR expression in a reference cell, such as a control cell that has not been contacted with the compounds.

Also featured herein are compositions and methods for inducing LDLR activity in a cell, such as a cell in a subject (e.g., a human, such as a human with an elevated cholesterol associated disease) or a cell in a culture (e.g., a culture generated from a human (e.g., a human with an elevated cholesterol associated) sample, or a repository of human sample) by contacting the cell with one or more compounds of this invention (e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds). One or more compounds of the invention, whether used in monotherapy or in combination therapy, can induce LDLR activity in a cell by at least 5% or more (e.g., between 5-20%, between 5-50%, between 10-50%, between 10-80%, between 20-80%, or between 20-100%) relative to LDLR activity prior to contacting with the compounds, or relative to LDLR activity in a reference cell, such as a control cell that has not been contacted with the compounds. In some embodiments, one or more compounds of the invention, whether used in monotherapy or in combination therapy, can induce LDLR activity in a cell by at least 5%, 10%, 15%, 20%, 25%, 30%, 40%, 50%, 60%, 70%, 80%, 90%, 95%, 99%, or more relative to LDLR activity prior to contacting with the compounds, or relative to LDLR activity in a reference cell, such as a control cell that has not been contacted with the compounds.

Additionally, provided herein are compositions and methods for treating one or more elevated cholesterol associated disease (e.g., atherosclerosis, hypercholesterolemia (heterozygous and homozygous familial hypercholesterolemia included), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure) in a subject in need thereof (e.g., a human, such as a human with an elevated cholesterol associated disease) by administering to the subject one or more compounds of this invention (e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds).

Featured herein are compositions and methods for reducing one or more symptoms or indications of an elevated cholesterol associated disease (e.g., atherosclerosis, hypercholesterolemia (heterozygous and homozygous familial hypercholesterolemia included), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure) in a subject (e.g., a human, such as a human with an elevated cholesterol associated disease) in need thereof by administering to the subject one or more compounds of this invention (e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds). One or more compounds of the invention, whether used in monotherapy or in combination therapy, can reduce one or more symptoms or indications of an elevated cholesterol associated disease in a subject (e.g., a subject with the elevated cholesterol associated disease) by at least 5% or more (e.g., between 5-20%, between 5-50%, between 10-50%, between 10-80%, between 20-80%, or between 20-100%) relative to the symptoms or indications prior to administration of the compounds, or relative to the symptoms or indications in a reference subject to whom the compounds have not been administered (e.g., a subject with the elevated cholesterol associated disease to whom the compounds have not been administered). In some embodiments, one or more compounds of the invention, whether used in monotherapy or in combination therapy, can reduce one or more symptoms or indications of an elevated cholesterol associated disease in a subject (e.g., a subject with the elevated cholesterol associated disease) by at least 5%, 10%, 15%, 20%, 25%, 30%, 40%, 50%, 60%, 70%, 80%, 90%, 95%, 99%, or more relative to the symptoms or indications prior to administration of the compounds, or relative to the symptoms or indications in a reference subject to whom the compounds have not been administered (e.g., a subject with the elevated cholesterol associated disease to whom the compounds have not been administered).

Also featured herein are compositions and methods for delaying the onset of an elevated cholesterol associated disease (e.g., atherosclerosis, hypercholesterolemia (heterozygous and homozygous familial hypercholesterolemia included), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure) in a subject (e.g., a human, such as a human predisposed to an elevated cholesterol associated disease) by administering to the subject one or more compounds of this invention (e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds). One or more compounds of the invention, whether used in monotherapy or in combination therapy, can delay the onset of an elevated cholesterol associated disease in a subject (e.g., a human, such as a human predisposed to an elevated cholesterol associated disease) by at least 1 month or more (e.g., 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, or more) relative to a reference subject to whom the compounds have not been administered (e.g., a subject predisposed to the elevated cholesterol associated disease to whom the compounds have not been administered).

Also provided herein are compositions and methods for reducing the likelihood or chance of occurrence of an elevated cholesterol associated disease (e.g., atherosclerosis, hypercholesterolemia (heterozygous and homozygous familial hypercholesterolemia included), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure) in a subject (e.g., a human, such as a human predisposed to an elevated cholesterol associated disease) by administering to the subject one or more compounds of this invention (e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds). One or more compounds of the invention, whether used in monotherapy or in combination therapy, can reduce the likelihood or chance of occurrence of an elevated cholesterol associated disease in a subject (e.g., a human, such as a human predisposed to an elevated cholesterol associated disease) by at least 5% or more (e.g., between 5-20%, between 5-50%, between 10-50%, between 10-80%, between 20-80%, or between 20-100%) relative to a reference subject to whom the compounds have not been administered (e.g., a subject predisposed to the elevated cholesterol associated disease to whom the compounds have not been administered). In some embodiments, one or more compounds of the invention, whether used in monotherapy or in combination therapy, can reduce the likelihood or chance of occurrence of an elevated cholesterol associated disease in a subject (e.g., a human, such as a human predisposed to an elevated cholesterol associated disease) by at least 5%, 10%, 15%, 20%, 25%, 30%, 40%, 50%, 60%, 70%, 80%, 90%, 95%, 99%, or more relative to a reference subject to whom the compounds have not been administered (e.g., a subject predisposed to the elevated cholesterol associated disease to whom the compounds have not been administered).

Also featured herein are compositions and methods for delaying the progression of an elevated cholesterol associated disease (e.g., atherosclerosis, hypercholesterolemia (heterozygous and homozygous familial hypercholesterolemia included), hypertriglyceridemia, diabetic complications, dyslipidemia, hyperlipidemia, hypo-alpha-lipoproteinemia, metabolic syndrome, stroke, vascular dementia, chronic kidney disease, coronary heart disease, coronary artery disease, retinopathy, inflammation, thrombosis, peripheral vascular disease or congestive heart failure) in a subject in need thereof (e.g., a human, such as a human with an elevated cholesterol associated disease) by administering to the subject one or more compounds of this invention (e.g., such as one or more of compounds 1-52 of Table 1 or a compound of Formula I, II, III, IV, V, or VI) or a pharmaceutically acceptable salt or solvate thereof alone (monotherapy) or in combination (combination therapy) with one or more additional agents (e.g., cholesterol lowering agents and/or agents that increase the bioavailability or slow the metabolism of the compounds). One or more compounds of the invention, whether used in monotherapy or in combination therapy, can delay the progression of an elevated cholesterol associated disease in a subject (e.g., a subject with the elevated cholesterol associated disease) by at least 5% or more (e.g., between 5-20%, between 5-50%, between 10-50%, between 10-80%, between 20-80%, or between 20-100%) relative to the progression prior to administration of the compounds, or relative to progression in a reference subject to whom the compounds have not been administered (e.g., a subject with the elevated cholesterol associated disease to whom the compounds have not been administered). In some embodiments, one or more compounds of the invention, whether used in monotherapy or in combination therapy, can delay the progression of an elevated cholesterol associated disease in a subject (e.g., a subject with the elevated cholesterol associated disease) by at least 5%, 10%, 15%, 20%, 25%, 30%, 40%, 50%, 60%, 70%, 80%, 90%, 95%, 99%, or more relative to the progression prior to administration of the compounds, or relative to progression in a reference subject to whom the compounds have not been administered (e.g., a subject with the elevated cholesterol associated disease to whom the compounds have not been administered).

EXAMPLES

The following examples are put forth to provide those of ordinary skill in the art with a description of how the compounds described herein may be synthesized and used, and how the methods featured herein may be evaluated. The examples are intended to be purely exemplary of the invention and are not intended to limit the scope of the claims.

Example 1

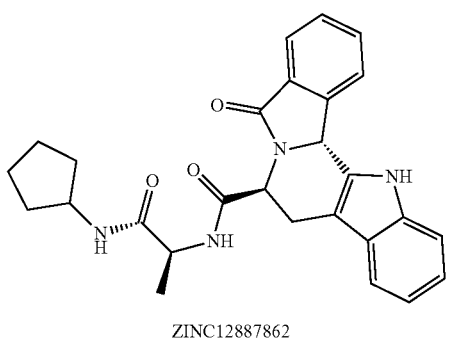

ZINC12887862

(2S)—N-cyclopentyl-2-{[(11 S)-9-oxo-10,20-diaza-pentacyclo[11.7.0.0²,¹⁰.0³,⁸.0¹⁴,¹⁹]icosa-1(13),3,5,7,14,16,18-heptaen-11-yl]formamido}propanamide

Example 2

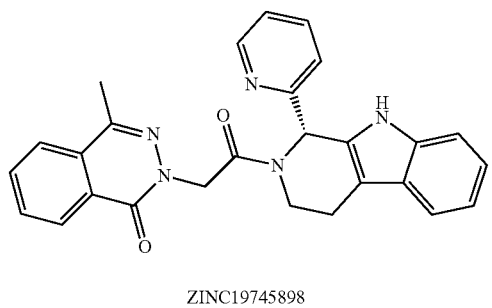 [SMILES: Cc1nn(CC(=O)N2CCc3c([nH]c4ccccc34)[C@H]2c2ccccn2)c(=O)c2ccccc12]

ZINC19745898

4-methyl-2-{2-oxo-2-[1-(2-pyridinyl)-1,3,4,9-tetra-hydro-2H-beta-carbolin-2-yl]ethyl}-1(2H)-phthalazi-none

Example 3

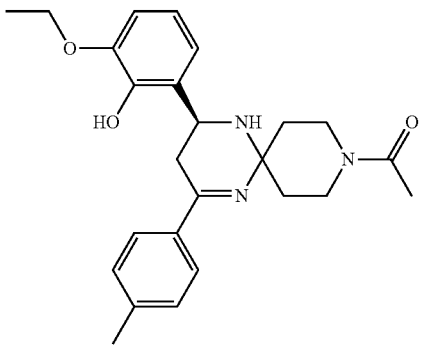

ZINC65298329

1-[4-(3-ethoxy-2-hydroxyphenyl)-2-(4-methylphe-nyl)-1,5,9-triazaspiro[5.5]undec-1-en-9-yl]ethan-1-one

Example 4

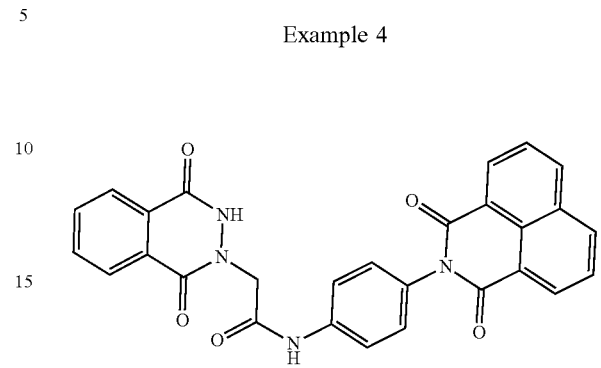

ZINC12631075

2-(1,4-dioxo-1,2,3,4-tetrahydrophthalazin-2-yl)-N-(4-{2,4-dioxo-3-azatricyclo[7.3.1.0^{5,13}]trideca-1(13),5,7,9,11-pentaen-3-yl}phenyl)acetamide

Example 5

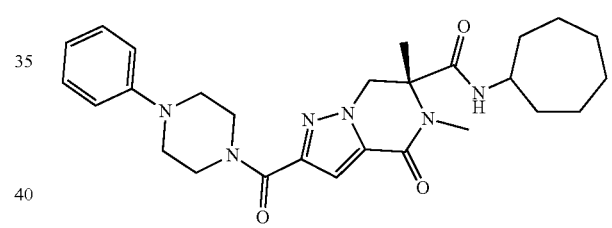

ZINC21875561

N-cycloheptyl-5,6-dimethyl-4-oxo-2-(4-phenylpip-erazine-1-carbonyl)-4H,5H,6H,7H-pyrazolo[1,5-a]pyrazine-6-carboxamide

Example 6

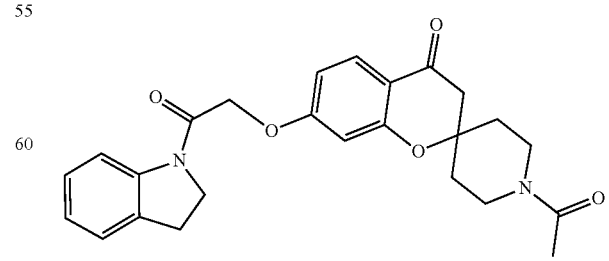

ZINC13720736

1'-acetyl-7-[2-(2,3-dihydro-1H-indol-1-yl)-2-oxoethoxy]-3,4-dihydrospiro[1-benzopyran-2,4'-piperidin]-4-one Example 7

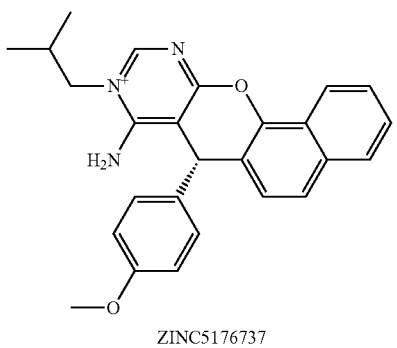 [SMILES: COc1ccc([C@H]2c3ccc4ccccc4c3Oc3nc[n+](CC(C)C)c(N)c32)cc1]

ZINC5176737

11-(4-methoxyphenyl)-14-(2-methylpropyl)-18-oxa-14,16-diazatetracyclo[8.8.0.02,7.012,17]octadeca-1(10),2,4,6,8,12(17),15-heptaen-13-imin Example 8

ZINC21938238

N-[2-(1H-indol-3-yl)ethyl]-6-oxo-5,6a,7,8,9,10-hexahydropyrido[1,2-a]quinoxaline-3-carboxamide Example 9

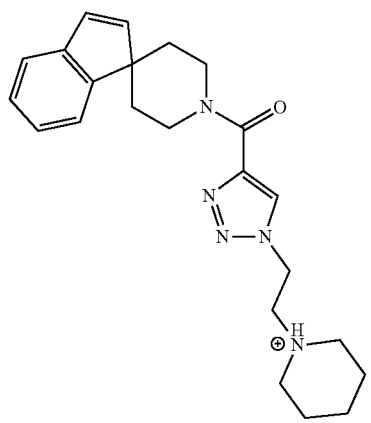

ZINC12053848

1'-{1-[2-(piperidin-1-yl)ethyl]-1H-1,2,3-triazole-4-carbonyl}spiro[indene-1,4'-piperidine]

Example 10

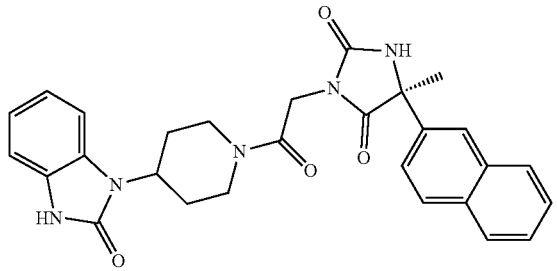

ZINC9952814

5-methyl-5-(naphthalen-2-yl)-3-{2-oxo-2-[4-(2-oxo-2,3-dihydro-1H-1,3-benzodiazol-1-yl)piperidin-1-yl]ethyl}imidazolidine-2,4-dione Example 11

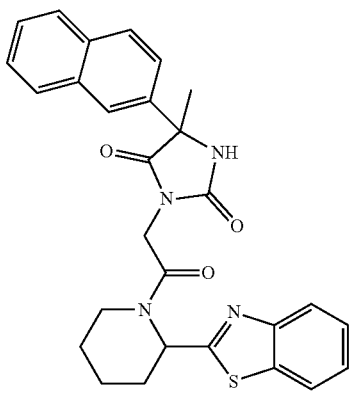

ZINC12684966

3-{2-[2-(1,3-benzothiazol-2-yl)piperidin-1-yl]-2-oxoethyl}-5-methyl-5-(naphthalen-2-yl)imidazolidine-2,4-dione Example 12

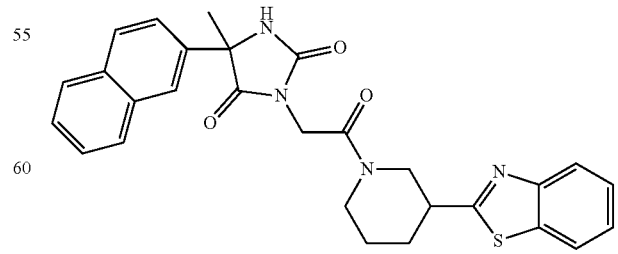

ZINC8733746

81

3-{2-[3-(1,3-benzothiazol-2-yl)piperidin-1-yl]-2-oxoethyl}-5-methyl-5-(naphthalen-2-yl)imidazolidine-2,4-dione Example 13

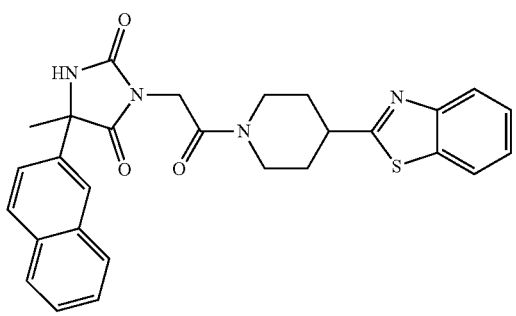

ZINC12690904

3-{2-[4-(1,3-benzothiazol-2-yl)piperidin-1-yl]-2-oxoethyl}-5-methyl-5-(naphthalen-2-yl)imidazolidine-2,4-dione Example 14

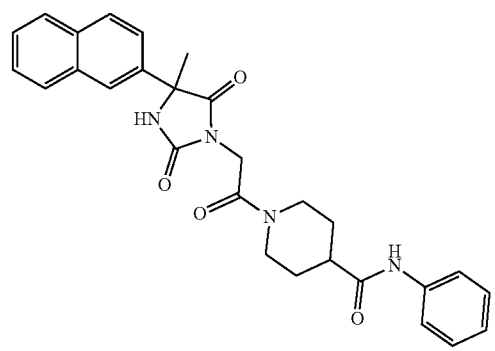

ZINC9642355

1-[2-[4-methyl-4-(2-naphthyl)-2,5-dioxo-imidazolidin-1-yl]acetyl]-N-phenyl-piperidine-4-carboxamide Example 15

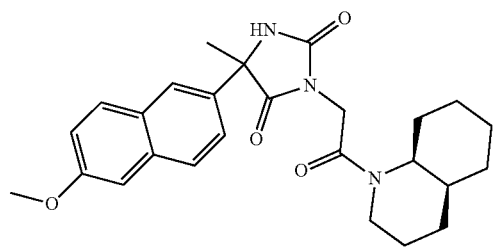

ZINC9992451

82

3-[2-(decahydroquinolin-1-yl)-2-oxoethyl]-5-(6-methoxynaphthalen-2-yl)-5-methylimidazolidine-2,4-dione Example 16

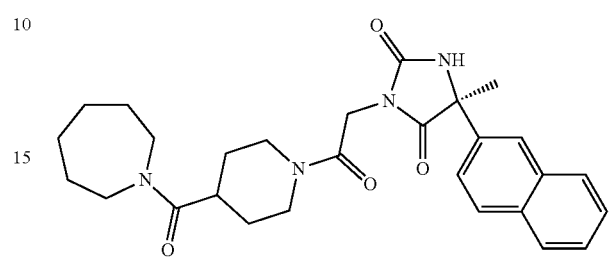

ZINC13165149

3-{2-[4-(azepane-1-carbonyl)piperidin-1-yl]-2-oxoethyl}-5-methyl-5-(naphthalen-2-yl)imidazolidine-2,4-dione Example 17

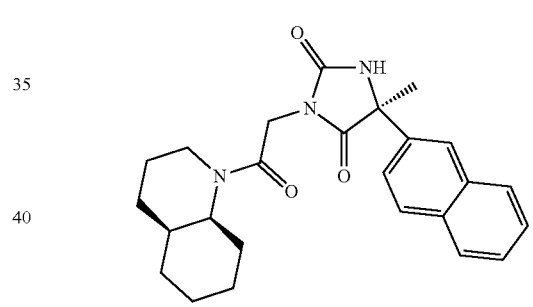

ZINC8189705

3-[2-(decahydroquinolin-1-yl)-2-oxoethyl]-5-methyl-5-(naphthalen-2-yl)imidazolidine-2,4-dione Example 18

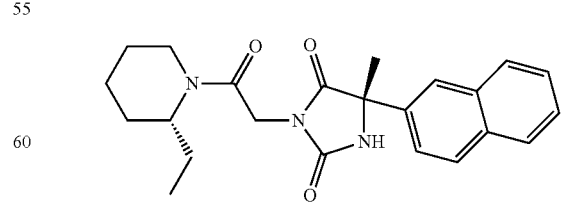

ZINC3336902

3-[2-(2-ethylpiperidin-1-yl)-2-oxoethyl]-5-methyl-5-(naphthalen-2-yl)imidazolidine-2,4-dione Example 19

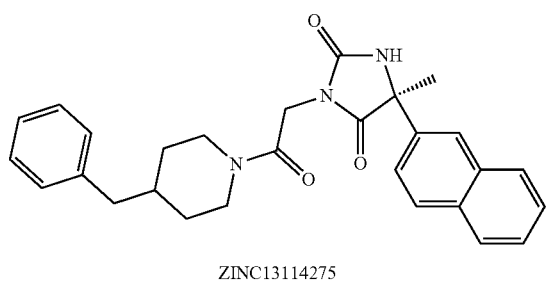 [SMILES: C[C@@]1(c2ccc3ccccc3c2)NC(=O)N(CC(=O)N2CCC(Cc3ccccc3)CC2)C1=O]

ZINC13114275

3-[2-(4-benzylpiperidin-1-yl)-2-oxoethyl]-5-methyl-5-(naphthalen-2-yl)imidazolidine-2,4-dione Example 20

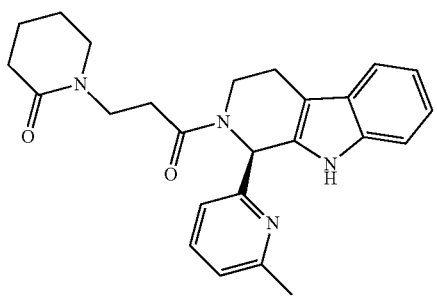

ZINC11937135

1-{3-[1-(6-methylpyridin-2-yl)-1H,2H,3H,4H,9H-pyrido[3,4-b]indol-2-yl]-3-oxopropyl}piperidin-2-one Example 21

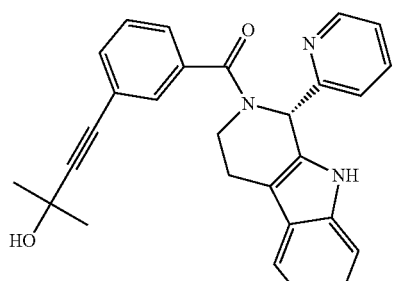

ZINC12373423

2-methyl-4-{3-[1-(pyridin-2-yl)-1H,2H,3H,4H,9H-pyrido[3,4-b]indole-2-carbonyl]phenyl}but-3-yn-2-ol Example 22

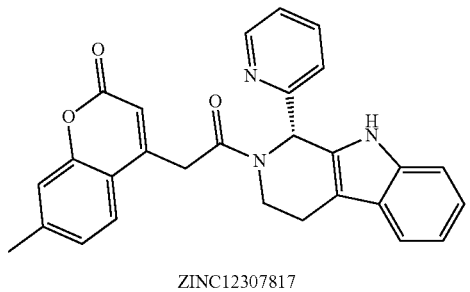 [SMILES: Cc1ccc2c(CC(=O)N3CCc4c([nH]c5ccccc45)[C@H]3c3ccccn3)cc(=O)oc2c1]

ZINC12307817

7-methyl-4-{2-oxo-2-[1-(pyridin-2-yl)-1H,2H,3H,4H,9H-pyrido[3,4-b]indol-2-yl]ethyl}-2H-chromen-2-one Example 23

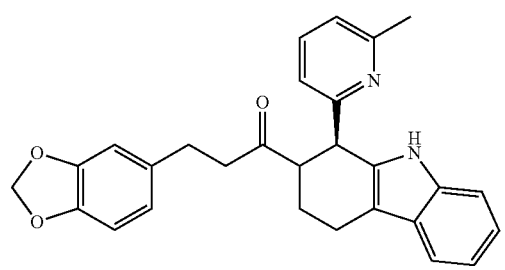

ZINC11666179

3-(1,3-benzodioxol-5-yl)-1-[(1S)-1-(6-methylpyridin-2-yl)-1,3,4,9-tetrahydropyrido[3,4-b]indol-2-yl]propan-1-one Example 24

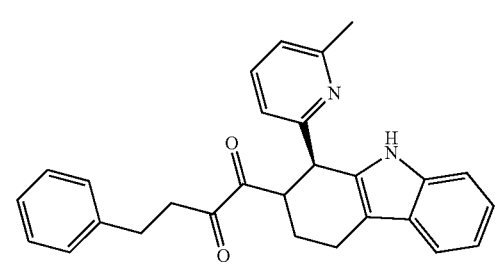

ZINC11934986

85

1-[1-(6-methylpyridin-2-yl)-1H,2H,3H,4H,9H-
pyrido[3,4-b]indol-2-yl]-4-phenylbutane-1,2-dione Example 25

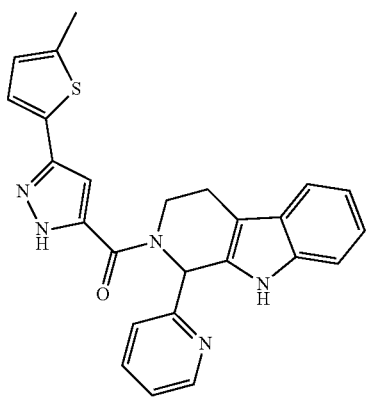

ZINC11820141

2-{[3-(5-methyl-2-thienyl)-1H-pyrazol-5-yl]carbo-
nyl}-1-(2-pyridinyl)-2,3,4,9-tetrahydro-1H-beta-
carboline Example 26

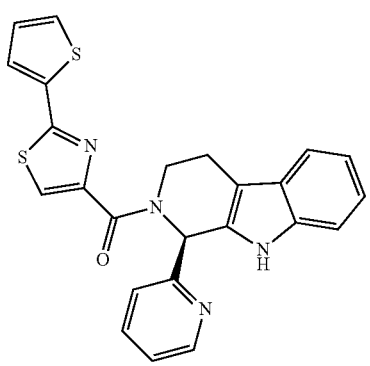

ZINC11818047

86

1-(2-pyridinyl)-2-{[2-(2-thienyl)-1,3-thiazol-4-yl]
carbonyl}-2,3,4,9-tetrahydro-1H-beta-carboline Example 27

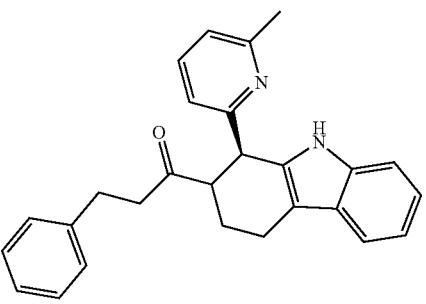

ZINC11937972

1-[1-(6-methylpyridin-2-yl)-1H,2H,3H,4H,9H-
pyrido[3,4-b]indol-2-yl]-3-phenylpropan-1-one Example 28

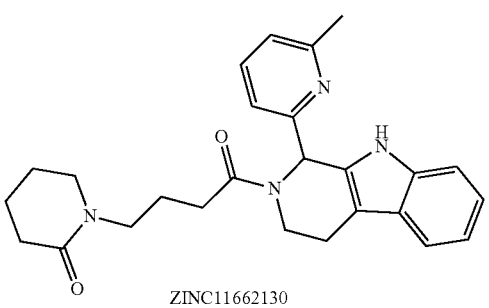 [SMILES: Cc1cccc(C2c3[nH]c4ccccc4c3CCN2C(=O)CCCN2CCCCC2=O)n1]

ZINC11662130

1-{4-[1-(6-methylpyridin-2-yl)-1H,2H,3H,4H,9H-
pyrido[3,4-b]indol-2-yl]-4-oxobutyl}piperidin-2-one Example 29

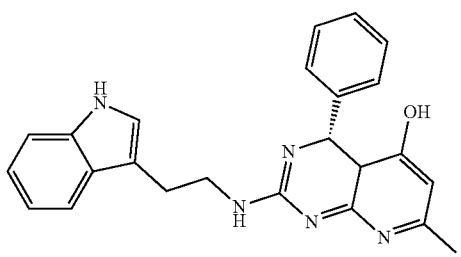

ZINC20028282

87

2-{[2-(1H-indol-3-yl)ethyl]amino}-8-methyl-4-phenyl-4H-pyrimido[1,2-a][1,3,5]triazin-6-ol Example 30

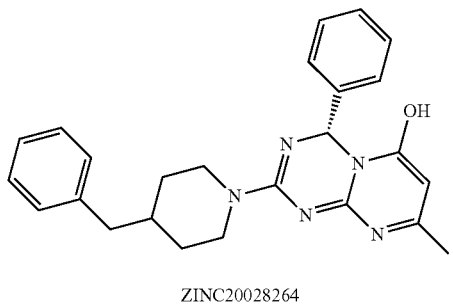 [SMILES: CC1=NC2=NC(N3CCC(Cc4ccccc4)CC3)=N[C@H](c3ccccc3)N2C(O)=C1]

ZINC20028264

2-(4-benzylpiperidin-1-yl)-8-methyl-4-phenyl-4H-pyrimido[1,2-a][1,3,5]triazin-6-ol Example 31

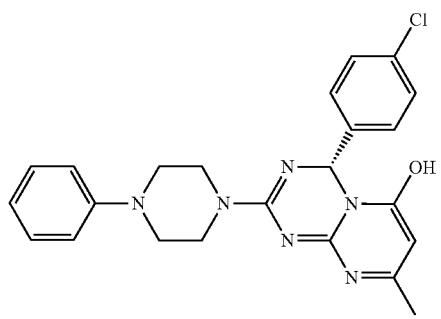

ZINC20028274

4-(4-chlorophenyl)-8-methyl-2-(4-phenylpiperazin-1-yl)-4H-pyrimido[1,2-a][1,3,5]triazin-6-ol Example 32

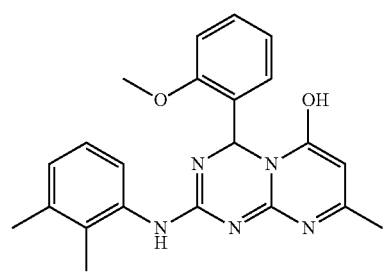

ZINC13592097

88

2-[(2,3-dimethylphenyl)amino]-4-(2-methoxyphenyl)-8-methyl-4H-pyrimido[1,2-a][1,3,5]triazin-6-ol Example 33

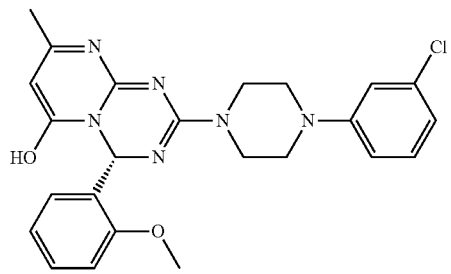

ZINC20028279

2-[4-(3-chlorophenyl)piperazin-1-yl]-4-(2-methoxyphenyl)-8-methyl-1,4-dihydro-6H-pyrimido[1,2-a][1,3,5]triazin-6-ol Example 34

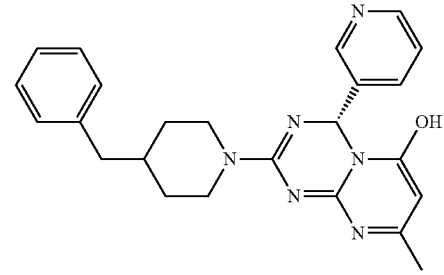

ZINC20028266

2-(4-benzylpiperidin-1-yl)-8-methyl-4-(pyridin-3-yl)-4H-pyrimido[1,2-a][1,3,5]triazin-6-ol Example 35

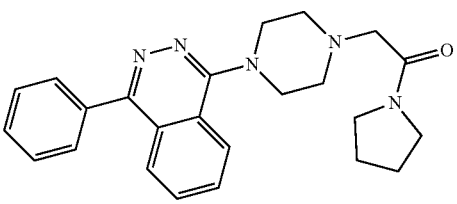

ZINC32719983

2-[4-(4-phenylphthalazin-1-yl)piperazin-1-yl]-1-(pyrrolidin-1-yl)ethan-1-one

Example 36

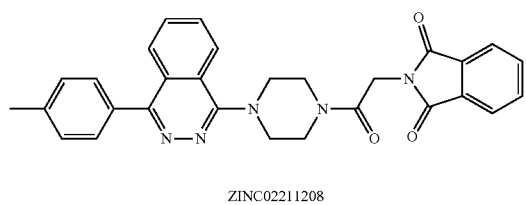 [SMILES: Cc1ccc(-c2nnc(N3CCN(C(=O)CN4C(=O)c5ccccc5C4=O)CC3)c3ccccc23)cc1]

ZINC02211208

2-(2-{4-[4-(4-methylphenyl)phthalazin-1-yl]piperazin-1-yl}-2-oxoethyl)-2,3-dihydro-1H-isoindole-1,3-dione Example 37

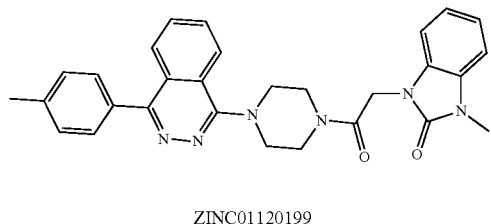

ZINC01120199

1-methyl-3-(2-{4-[4-(4-methylphenyl)phthalazin-1-yl]piperazin-1-yl}-2-oxoethyl)-2,3-dihydro-1H-1,3-benzodiazol-2-one Example 38

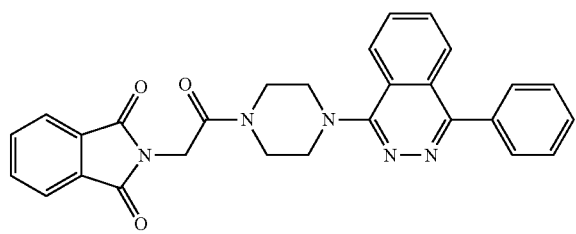

ZINC02393309

2-{2-oxo-2-[4-(4-phenylphthalazin-1-yl)piperazin-1-yl]ethyl}-2,3-dihydro-1H-isoindole-1,3-dione Example 39

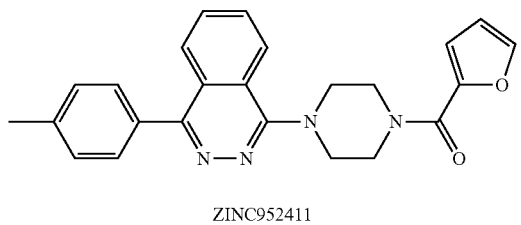 [SMILES: Cc1ccc(-c2nnc(N3CCN(C(=O)c4ccco4)CC3)c3ccccc23)cc1]

ZINC952411

1-[4-(furan-2-carbonyl)piperazin-1-yl]-4-(4-methylphenyl)phthalazine

Example 40

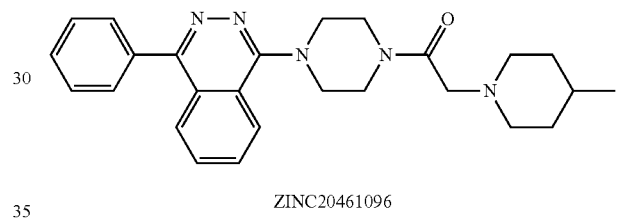

ZINC20461096

2-(4-methylpiperidin-1-yl)-1-[4-(4-phenylphthalazin-1-yl)piperazin-1-yl]ethan-1-one Example 41

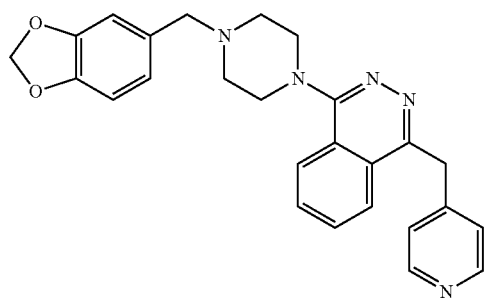

ZINC33315029

91

1-{4-[(2H-1,3-benzodioxol-5-yl)methyl]piperazin-1-yl}-4-[(pyridin-4-yl)methyl]phthalazine Example 42

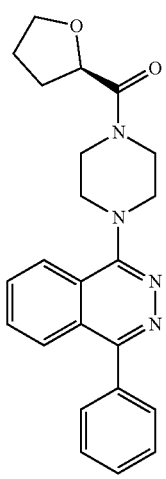

ZINC33010963

1-[4-(oxolane-2-carbonyl)piperazin-1-yl]-4-phenylphthalazine

Example 43

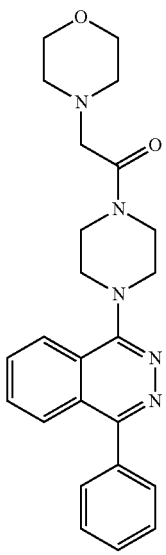

ZINC4196819

92

2-(morpholin-4-yl)-1-[4-(4-phenylphthalazin-1-yl)piperazin-1-yl]ethan-1-one

Example 44

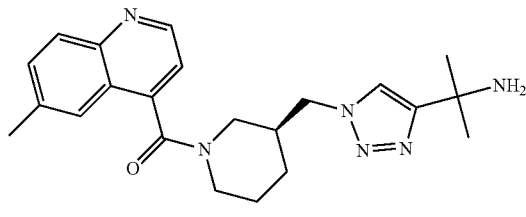

ZINC48319756

2-[1-({1-[(6-methylquinolin-4-yl)carbonyl]piperidin-3-yl}methyl)-1H-1,2,3-triazol-4-yl]propan-2-amine Example 45

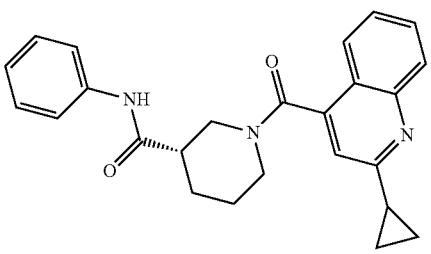

ZINC12935015

1-(2-cyclopropylquinoline-4-carbonyl)-N-phenylpiperidine-3-carboxamide

Example 46

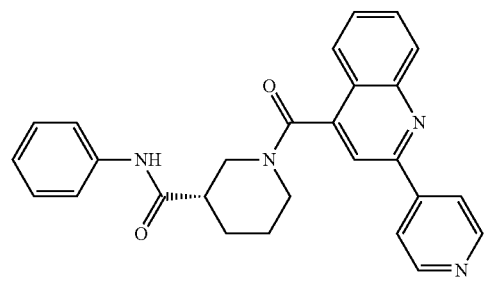

ZINC17823320

N-phenyl-1-[2-(pyridin-4-yl)quinoline-4-carbonyl]
piperidine-3-carboxamide

Example 47

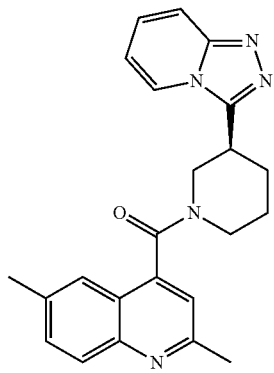

ZINC40050317

2,6-dimethyl-4-(3-{[1,2,4]triazolo[4,3-a]pyridin-3-
yl}piperidine-1-carbonyl)quinoline Example 48

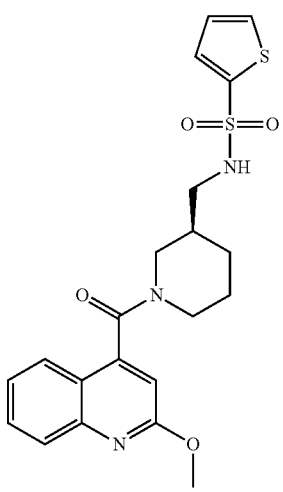

ZINC12577975

N-{[1-(2-methoxyquinoline-4-carbonyl)piperidin-3-
yl]methyl}thiophene-2-sulfonamide Example 49

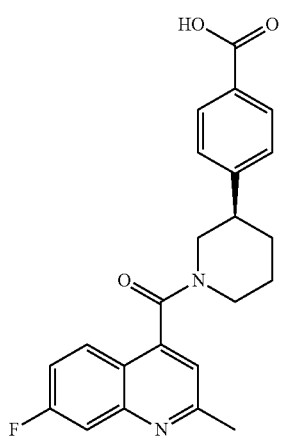

ZINC95382164

4-[1-(7-fluoro-2-methylquinoline-4-carbonyl)piperi-
din-3-yl]benzoic acid

Example 50

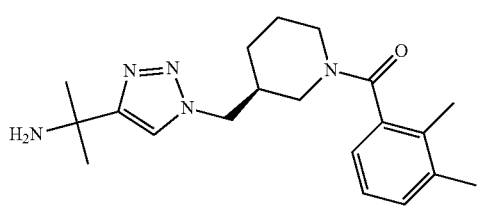

ZINC48441266

2-(1-{[1-(2,3-dimethylbenzoyl)piperidin-3-yl]
methyl}-1H-1,2,3-triazol-4-yl)propan-2-amine Example 51

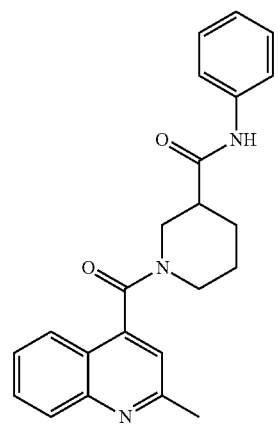

ZINC9112445

1-(2-methylquinoline-4-carbonyl)-N-phenylpiperi-
dine-3-carboxamide

Example 52

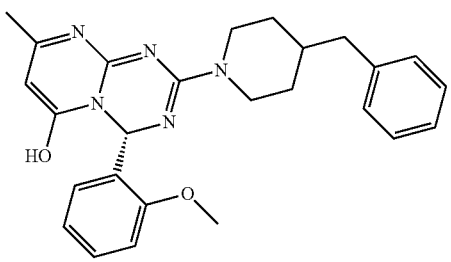

ZINC20345702

2-(4-benzylpiperidin-1-yl)-4-(2-methoxyphenyl)-8-
methyl-4H-pyrimido[1,2-a][1,3,5]triazin-6-ol Example 53

SHIM screen. SHIM compounds were designed using the small hyper-interaction modulation (SHIM) method, essentially as described previously (Cai et al., 2008), but with modifications in certain steps of the method including development of compound database for virtual screening, selection of targeted binding pockets and development of optimized scoring function. SHIMs compounds were selected as they can form a ternary SHIM-A-B complex with complex-forming molecules (or parts of a molecules) A (in this case conformationally stable part of PCSK9) and B (flexible SHIM loop) in such a way that in the ternary complex, SHIM compounds are making contacts with both the stable part and the targeted SHIM PCSK9 loop (FIG. 1).

Example 54

Figure 2:
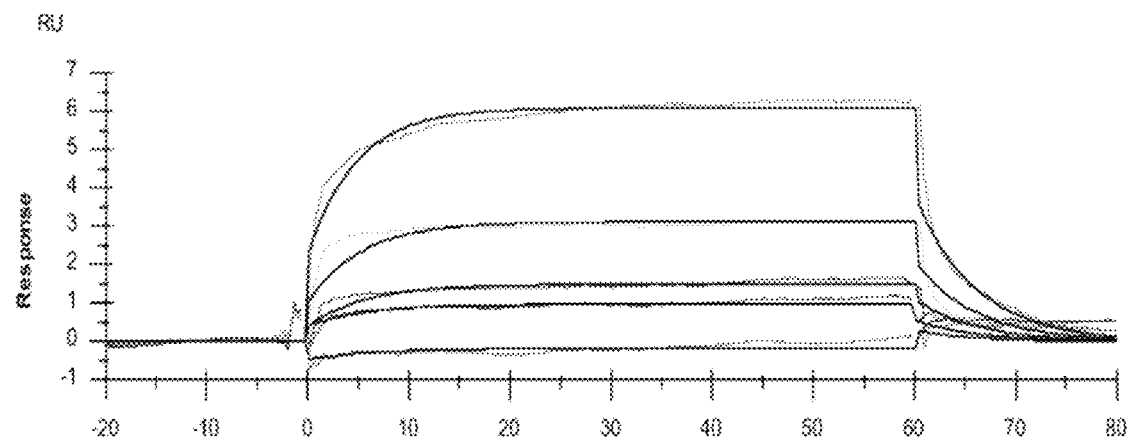
FIG. 2 is a series of two surface plasmon spectroscopy sensorgrams obtained for compounds 10 and 26 and corresponding to the affinity data listed in Table 4.
Figure 2:
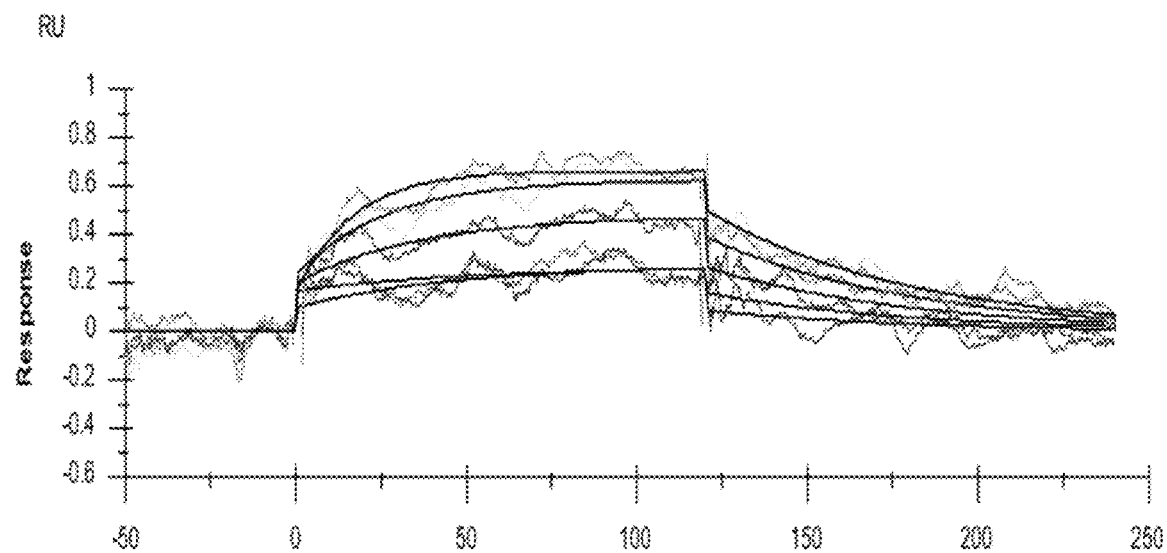
Figure 3:
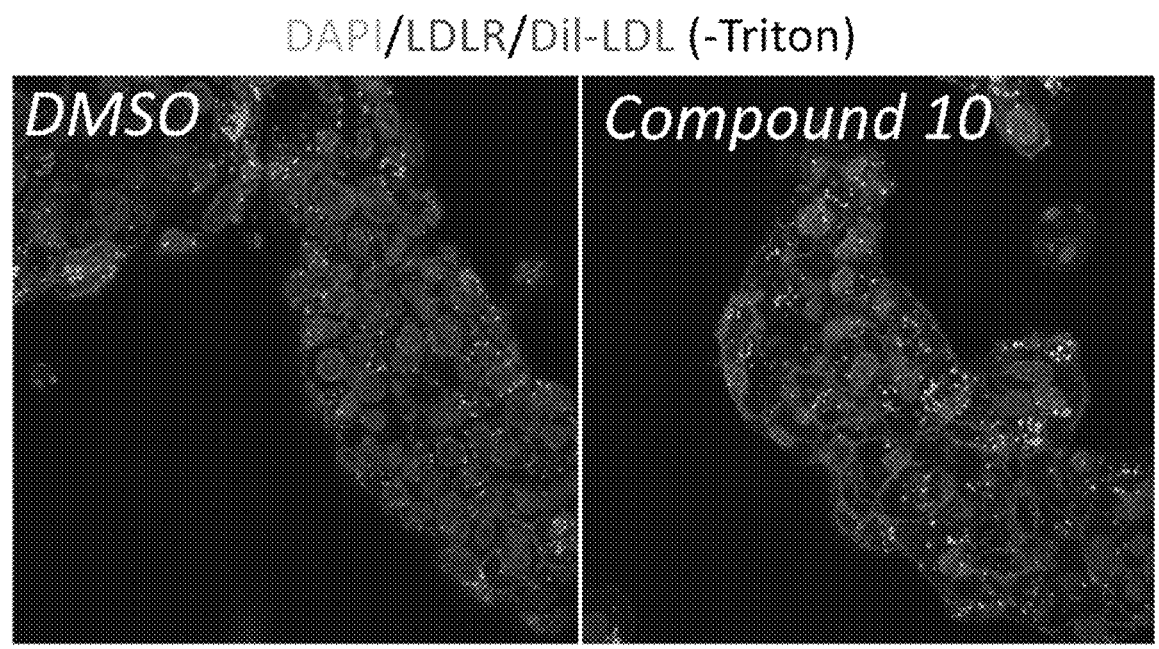
FIG. 3 is a series of two images showing cell surface LDLR expression and DiI-LDL internalization in human hepatic HepG2 cells following treatment with Compound 10 or DMSO (used as vehicle).
Figure 4:
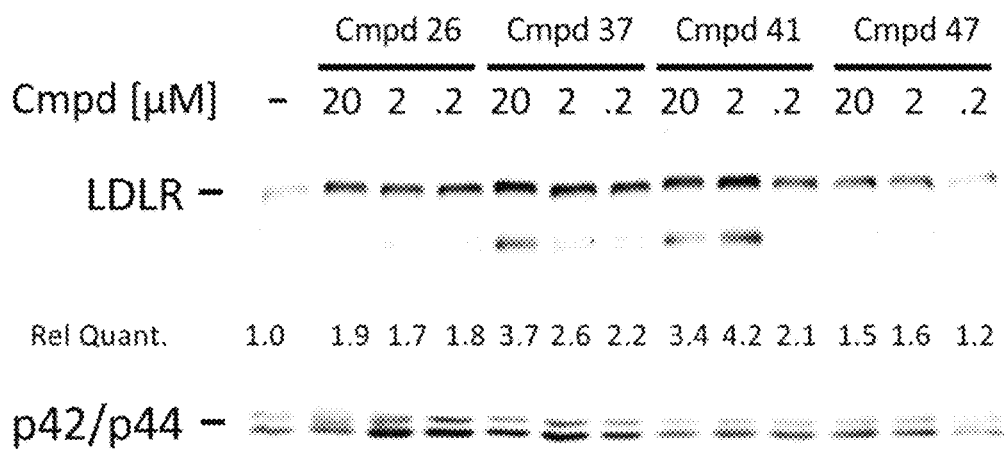
FIG. 4 is an image and a graph of Western Blot analysis of LDLR protein levels and MTT cytotoxicity assay in HepG2 treated for 18h in the presence of 0.2, 1, 2, 5, 10, 20, 50, 100, or 500 μM of compounds 26, 37, 41, 47, or 10, or DMSO (n=3). At each concentration of compound, the order of compounds shown, from left to right, is as follows: DMSO, compound 26, compound 37, compound 41, compound 47, and compound 10.
Figure 4:
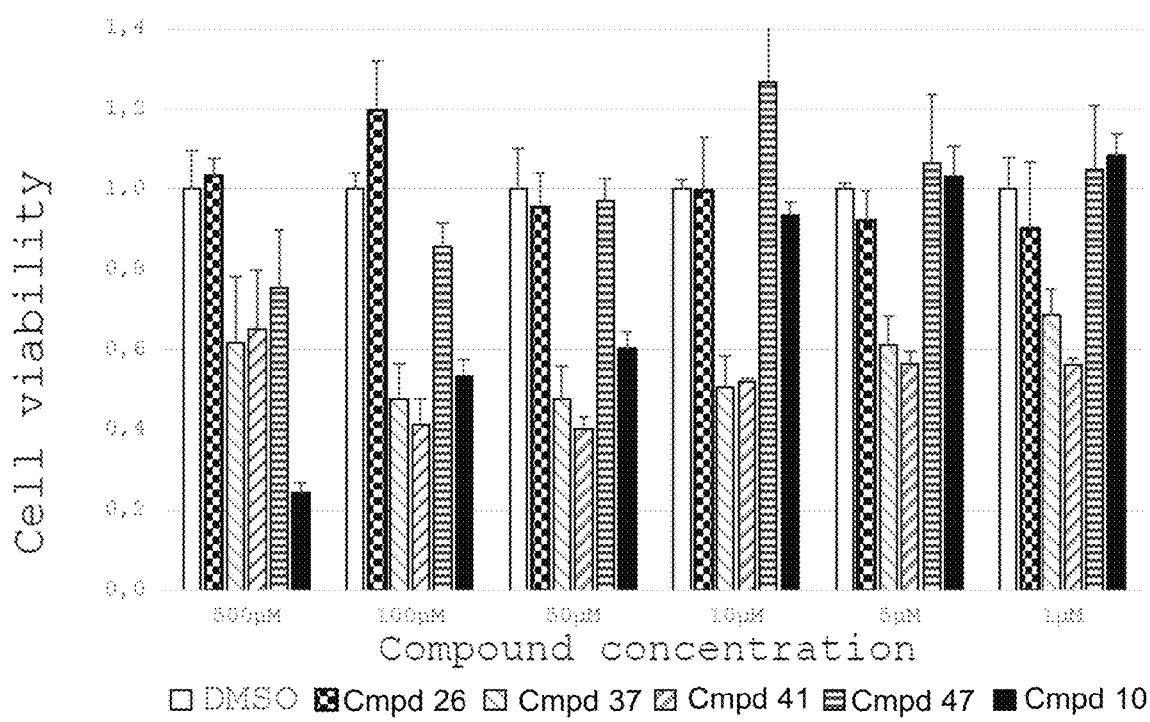
Figure 5:
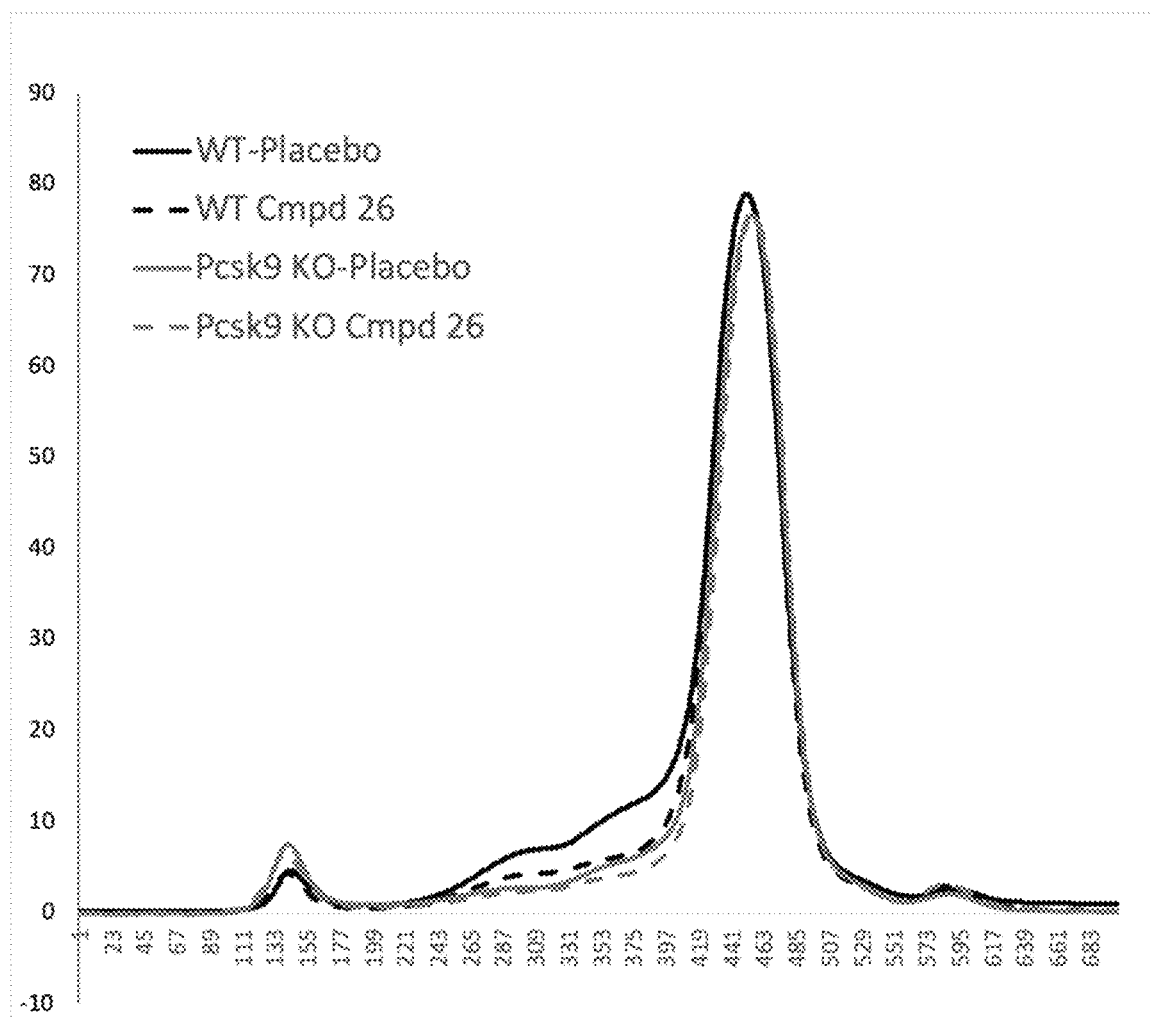
FIG. 5 is a graph showing Plasma Lipoprotein Cholesterol Profiles of hypercholesterolemic C57BL/6 and Pcsk9 KO mice following oral gavage of vehicle (placebo) or 40 mg/kg/day of Compound 26 for 10 days (pooled samples of n=4 to 5) analyzed by Fast Protein Liquid Chromatography (FPLC).

Studies of SHIM compounds—PCSK9 interactions. Binding of affinity of SHIM compounds has been determined using surface plasmon spectroscopy on a Biacore T200 (GE Healthcare). Biotinylated PCSK9 (ACRO Biosystems) at 1 µg/mL has been captured on a chip on which streptavidin has been immobilized with amine-directed chemistry according to the manufacturer's instructions (6000 RU) to a density of 6000 RU in PBS-P (potassium buffered saline, 0.005% Tween 20, pH7.4) buffer with 1% DMSO. SHIMs at 10, 3.3, 1.1, 0.33 and 0.11 uM were injected at 30 uL/min. The data were fitted to 1:1 Langmuir binding model using Bioeval 4.3 software (GE Healthcare) to obtain the KD values. Double reference method of analysis was used with the reference channel containing a reference biotinylated protein captured at 6000 RU. The measured values for the selected examples are shown in Table 4 and sensorgrams for compounds 10 and 26 are shown in FIG. 2.

Example 55

Cell culture, treatments and cell viability assay. For phenotypic screening of PCSK9 modulators and/or LDLR small molecule inducers, human HepG2 cells were incubated overnight in conditioned media containing chemical compounds resuspended in DMSO at concentration ranging from 0.2 µM to 20 µM. For cell viability assay, cells have been seeded into 96-well plates and incubated at confluency overnight with 1, 5, 10, 50, 100 or 500 µM of given compounds in phenol red-free conditioned media (catalog no. 319-051-CL, Wisent). Following incubation, media have been replaced and cells incubated for 4 h with 100 µL of phenol red-free DMEM containing 0.5 mg/mL of MTT (3-[4,5-dimethylthiazol-2-yl]-2,5-diphenyltetrazolium bromide; thiazolyl blue; catalog no. M5655, Sigma-Aldrich), following manufacturer's instructions. Arbitrary units of cell viability of a given example have been determined relative to equal volume of DMSO (vehicle) for each concentration used.

Example 56

Western Blot Analysis, Immunocytochemistry and LDLR Activity Assay. Following incubation, cells were washed three times in phosphate-buffered saline (PBS) and lysed in radioimmune precipitation assay buffer (50 mM Tris/HCl, pH 8.0, 1% (v/v) Nonidet P-40, 0.5% sodium deoxycholate, 150 mM NaCl, and 0.1% (v/v) SDS) supplemented with a complete protease inhibitor mixture (catalog no. 11 697 498 001, Roche Applied Science). Proteins were separated by SDS polyacrylamide gel electrophoresis, blotted on nitrocellulose membranes (Bio-Rad), blocked incubated with indicated antibodies as described (Poirier S, et al., Cell Rep, 2015). For immunocytochemistry analysis, cells were permeabilized or not with 0.1% Triton X-100/PBS for 10 min, and incubated with 150 mM glycine, blocked and incubated with indicated primary and secondary antibodies. Immunofluorescence analyses were performed with an Olympus FluoView FV10i confocal microscope (Poirier et al., Cell Rep. 2015; 13(10):2064-2071). For LDLR activity assay, HepG2 cells were incubated overnight without or with a given compound in the presence of 5 µg/ml fluorescent labelled DiI-LDL (Alfa Aesar, Cat. #J65330) and co-stained for LDLR if applicable, as described (Poirier et al., J Biol Chem. 2009; 284(42):28856-28864). Immunofluorescence analyses were performed with an Olympus FluoView FV10i confocal microscope.

Example 57

Animal studies. All animal studies were approved by the Montreal Heart Institute (MHI) Animal Care and Ethical committee. For in vivo proof-of-concept animal studies, wild-type C57BL/6 or Pcsk9 knockout male mice were fed on Western diet containing 48.5% w/w carbohydrate, 21.2% w/w fat, 17.3% w/w protein and 0.2% w/w cholesterol (catalog no. TD.88137, Envigo) for 14 days. Chemical compounds were mixed in DMSO/propylene glycol/water; 1:7:2 (v/v) and administered by oral gavage at 0 (vehicle) or 40 mg/kg/day for 10 days in mice on Western diet. Plasma lipoprotein cholesterol profiles were obtained from 100 µL of pooled plasma injected on a Superose 6 10/300 GL (catalog no. 17-5172-01, GE Life Sciences) and eluted with PBS at a flow rate of 0.1 mL per min at 4° C. mounted on a AKTA explorer system (GE Healthcare). Serum aspartate aminotransferase (AST), alanine transaminase (ALT), insulin, glucose and complete hematology tests were measured by the Montreal Heart Institute biochemical clinical chemistry platform according to manufacturer's recommendations.

TABLE 4

Binding affinity of SHIM compounds as determined using surface plasmon resonance spectroscopy.

| Compound # | Range tested | ka (M−1 sec−1) | kd (sec−1) | KD (M) |
|---|---|---|---|---|
| 10 | 0.5-10 uM | 3.33E+4 | 0.19 | 5.8E−6 |
| 14 | 0.5-10 uM | 1.45E+4 | 0.19 | 1.38E−5 |
| 16 | 0.5-10 uM | 2.28E+4 | 0.09 | 3.88E−6 |
| 19 | 0.5-10 uM | NB | NB | NB |
| 26 | 0.5-10 uM | 1.04E+5 | 1.14 | 1.1E−5 |
| 47 | 0.5-10 uM | 2.51E+3 | 0.03 | 1.2E−5 | ka - association rate constant;
kd - dissociation rate constant;
KD - equilibrium dissociation constant;
NB - no binding detected in the tested range

TABLE 5

Relative LDLR Protein Levels Following Treatment with Exemplified Compounds

| Ex. No | ZINC No | Chemical Name | LDLR Fold |
|---|---|---|---|
| 1 | ZINC12887862 | (2S)-N-cyclopentyl-2-{[(11S)-9-oxo-10,20-diazapentacyclo[11.7.0.0$^{2,10}$.0$^{3,8}$.0$^{14,19}$]icosa-1(13),3,5,7,14,16,18-heptaen-11-yl]formamido}propanamide | 1.2 ± 0.2 |
| 2 | ZINC19745898 | 4-methyl-2-{2-oxo-2-[1-(2-pyridinyl)-1,3,4,9-tetrahydro-2H-beta-carbolin-2-yl]ethyl}-1(2H)-phthalazinone | 1.0 ± 0.5 |
| 3 | ZINC65298329 | 1-[4-(3-ethoxy-2-hydroxyphenyl)-2-(4-methylphenyl)-1,5,9-triazaspiro[5.5]undec-1-en-9-yl]ethan-1-one | 1.8 ± 0.6 |
| 4 | ZINC12631075 | 2-(1,4-dioxo-1,2,3,4-tetrahydrophthalazin-2-yl)-N-(4-{2,4-dioxo-3-azatricyclo[7.3.1.0^{5,13}]trideca-1(13),5,7,9,11-pentaen-3-yl}phenyl)acetamide | 1.6 ± 0.2 |
| 5 | ZINC21875561 | N-cycloheptyl-5,6-dimethyl-4-oxo-2-(4-phenylpiperazine-1-carbonyl)-4H,5H,6H,7H-pyrazolo[1,5-a]pyrazine-6-carboxamide | 0.8 ± 0.0 |
| 6 | ZINC13720736 | 1'-acetyl-7-[2-(2,3-dihydro-1H-indol-1-yl)-2-oxoethoxy]-3,4-dihydrospiro[1-benzopyran-2,4'-piperidin]-4-one | 0.8 ± 0.3 |
| 7 | ZINC05176737 | 11-(4-methoxyphenyl)-14-(2-methylpropyl)-18-oxa-14,16-diazatetracyclo[8.8.0.02,7.012,17]octadeca-1(10),2,4,6,8,12(17),15-heptaen-13-imin | 0.0 ± 0.0 |
| 8 | ZINC21938238 | N-[2-(1H-indol-3-yl)ethyl]-6-oxo-5,6a,7,8,9,10-hexahydropyrido[1,2-a]quinoxaline-3-carboxamide | 1.0 ± 0.2 |
| 9 | ZINC12053848 | 1'-{1-[2-(piperidin-1-yl)ethyl]-1H-1,2,3-triazole-4-carbonyl}spiro[indene-1,4'-piperidine] | 0.4 ± 0.1 |
| 10 | ZINC09952814 | 5-methyl-5-(naphthalen-2-yl)-3-{2-oxo-2-[4-(2-oxo-2,3-dihydro-1H-1,3-benzodiazol-1-yl)piperidin-1-yl]ethyl}imidazolidine-2,4-dione | 3.0 ± 1.2 |
| 11 | ZINC12684966 | 3-{2-[2-(1,3-benzothiazol-2-yl)piperidin-1-yl]-2-oxoethyl}-5-methyl-5-(naphthalen-2-yl)imidazolidine-2,4-dione | 1.5 ± 0.4 |
| 12 | ZINC08733746 | 3-{2-[3-(1,3-benzothiazol-2-yl)piperidin-1-yl]-2-oxoethyl}-5-methyl-5-(naphthalen-2-yl)imidazolidine-2,4-dione | 1.8 ± 0.6 |
| 13 | ZINC12690904 | 3-{2-[4-(1,3-benzothiazol-2-yl)piperidin-1-yl]-2-oxoethyl}-5-methyl-5-(naphthalen-2-yl)imidazolidine-2,4-dione | 1.5 ± 0.7 |
| 14 | ZINC09642355 | 1-[2-[4-methyl-4-(2-naphthyl)-2,5-dioxo-imidazolidin-1-yl]acetyl]-N-phenyl-piperidine-4-carboxamide | 2.0 ± 0.7 |
| 15 | ZINC09992451 | 3-[2-(decahydroquinolin-1-yl)-2-oxoethyl]-5-(6-methoxynaphthalen-2-yl)-5-methylimidazolidine-2,4-dione | 1.1 ± 0.6 |
| 16 | ZINC13165149 | 3-{2-[4-(azepane-1-carbonyl)piperidin-1-yl]-2-oxoethyl}-5-methyl-5-(naphthalen-2-yl)imidazolidine-2,4-dione | 2.1 ± 1.2 |
| 17 | ZINC08189705 | 3-[2-(decahydroquinolin-1-yl)-2-oxoethyl]-5-methyl-5-(naphthalen-2-yl)imidazolidine-2,4-dione | 1.2 ± 0.6 |

TABLE 5-continued

Relative LDLR Protein Levels Following
Treatment with Exemplified Compounds

| Ex. No | ZINC No | Chemical Name | LDLR Fold |
|---|---|---|---|
| 18 | ZINC03336902 | 3-[2-(2-ethylpiperidin-1-yl)-2-oxoethyl]-5-methyl-5-(naphthalen-2-yl)imidazolidine-2,4-dione | 1.4 ± 0.7 |
| 19 | ZINC13114275 | 3-[2-(4-benzylpiperidin-1-yl)-2-oxoethyl]-5-methyl-5-(naphthalen-2-yl)imidazolidine-2,4-dione | 1.0 ± 0.5 |
| 20 | ZINC11937135 | 1-{3-[1-(6-methylpyridin-2-yl)-1H,2H,3H,4H,9H-pyrido[3,4-b]indol-2-yl]-3-oxopropyl}piperidin-2-one | 1.4 |
| 21 | ZINC12373423 | 2-methyl-4-{3-[1-(pyridin-2-yl)-1H,2H,3H,4H,9H-pyrido[3,4-b]indole-2-carbonyl]phenyl}but-3-yn-2-ol | 1.0 |
| 22 | ZINC12307817 | 7-methyl-4-{2-oxo-2-[1-(pyridin-2-yl)-1H,2H,3H,4H,9H-pyrido[3,4-b]indol-2-yl]ethyl}-2H-chromen-2-one | 1.4 |
| 23 | ZINC11666179 | 3-(1,3-benzodioxol-5-yl)-1-[(1S)-1-(6-methylpyridin-2-yl)-1,3,4,9-tetrahydropyrido[3,4-b]indol-2-yl]propan-1-one | 1.2 |
| 24 | ZINC11934986 | 1-[1-(6-methylpyridin-2-yl)-1H,2H,3H,4H,9H-pyrido[3,4-b]indol-2-yl]-4-phenylbutane-1,2-dione | 1.6 |
| 25 | ZINC11820141 | 2-{[3-(5-methyl-2-thienyl)-1H-pyrazol-5-yl]carbonyl}-1-(2-pyridinyl)-2,3,4,9-tetrahydro-1H-beta-carboline | 1.1 |
| 26 | ZINC11818047 | 1-(2-pyridinyl)-2-{[2-(2-thienyl)-1,3-thiazol-4-yl]carbonyl}-2,3,4,9-tetrahydro-1H-beta-carboline | 1.9 ± 0.5 |
| 27 | ZINC11937972 | 1-[1-(6-methylpyridin-2-yl)-1H,2H,3H,4H,9H-pyrido[3,4-b]indol-2-yl]-3-phenylpropan-1-one | 1.0 |
| 28 | ZINC11662130 | 1-{4-[1-(6-methylpyridin-2-yl)-1H,2H,3H,4H,9H-pyrido[3,4-b]indol-2-yl]-4-oxobutyl}piperidin-2-one | 1.0 |
| 29 | ZINC20028282 | 2-{[2-(1H-indol-3-yl)ethyl]amino}-8-methyl-4-phenyl-4H-pyrimido[1,2-a][1,3,5]triazin-6-ol | 0.9 |
| 30 | ZINC20028264 | 2-(4-benzylpiperidin-1-yl)-8-methyl-4-phenyl-4H-pyrimido[1,2-a][1,3,5]triazin-6-ol | 0.6 |
| 31 | ZINC20028274 | 4-(4-chlorophenyl)-8-methyl-2-(4-phenylpiperazin-1-yl)-4H-pyrimido[1,2-a][1,3,5]triazin-6-ol | 1.1 |
| 32 | ZINC13592097 | 2-[(2,3-dimethylphenyl)amino]-4-(2-methoxyphenyl)-8-methyl-4H-pyrimido[1,2-a][1,3,5]triazin-6-ol | 0.8 |
| 33 | ZINC20028279 | 2-[4-(3-chlorophenyl)piperazin-1-yl]-4-(2-methoxyphenyl)-8-methyl-1,4-dihydro-6H-pyrimido[1,2- a][1,3,5]triazin-6-ol | 1.0 |
| 34 | ZINC20028266 | 2-(4-benzylpiperidin-1-yl)-8-methyl-4-(pyridin-3-yl)-4H-pyrimido[1,2-a][1,3,5]triazin-6-ol | 1.0 |
| 35 | ZINC32719983 | 2-[4-(4-phenylphthalazin-1-yl)piperazin-1-yl]-1-(pyrrolidin-1-yl)ethan-1-one | 0.9 |
| 36 | ZINC02211208 | 2-(2-{4-[4-(4-methylphenyl)phthalazin-1-yl]piperazin-1-yl}-2-oxoethyl)-2,3-dihydro-1H-isoindole-1,3-dione | 0.8 |
| 37 | ZINC01120199 | 1-methyl-3-(2-{4-[4-(4-methylphenyl)phthalazin-1-yl]piperazin-1-yl}-2-oxoethyl)-2,3-dihydro-1H-1,3-benzodiazol-2-one | 1.0 |
| 38 | ZINC02393309 | 2-{2-oxo-2-[4-(4-phenylphthalazin-1-yl)piperazin-1-yl]ethyl}-2,3-dihydro-1H-isoindole-1,3-dione | 0.9 |
| 39 | ZINC00952411 | 1-[4-(furan-2-carbonyl)piperazin-1-yl]-4-(4-methylphenyl)phthalazine | 0.9 |
| 40 | ZINC20461096 | 2-(4-methylpiperidin-1-yl)-1-[4-(4-phenylphthalazin-1-yl)piperazin-1-yl]ethan-1-one | 0.9 |
| 41 | ZINC33315029 | 1-{4-[(2H-1,3-benzodioxol-5-yl)methyl]piperazin-1-yl}-4-[(pyridin-4-yl)methyl]phthalazine | 0.7 |
| 42 | ZINC33010963 | 1-[4-(oxolane-2-carbonyl)piperazin-1-yl]-4-phenylphthalazine | 0.6 |
| 43 | ZINC04196819 | 2-(morpholin-4-yl)-1-[4-(4-phenylphthalazin-1-yl)piperazin-1-yl]ethan-1-one | 0.9 |
| 44 | ZINC48319756 | 2-[1-({1-[(6-methylquinolin-4-yl)carbonyl]piperidin-3-yl}methyl)-1H-1,2,3-triazol-4-yl]propan-2-amine | 1.2 |

TABLE 5-continued

Relative LDLR Protein Levels Following Treatment with Exemplified Compounds

| Ex. No | ZINC No | Chemical Name | LDLR Fold |
|---|---|---|---|
| 45 | ZINC12935015 | 1-(2-cyclopropylquinoline-4-carbonyl)-N-phenyl-piperidine-3-carboxamide | 1.2 |
| 46 | ZINC17823320 | N-phenyl-1-[2-(pyridin-4-yl)quinoline-4-carbonyl]piperidine-3-carboxamide | 1.1 |
| 47 | ZINC40050317 | 2,6-dimethyl-4-(3-{[1,2,4]triazolo[4,3-a]pyridin-3-yl}piperidine-1-carbonyl)quinoline | 1.6 |
| 48 | ZINC12577975 | N-{[1-(2-methoxyquinoline-4-carbonyl)piperidin-3-yl]methyl}thiophene-2-sulfonamide | 1.0 |
| 49 | ZINC95382164 | 4-[1-(7-fluoro-2-methylquinoline-4-carbonyl)piperidin-3-yl]benzoic acid | 1.6 |
| 50 | ZINC48441266 | 2-(1-{[1-(2,3-dimethylbenzoyl)piperidin-3-yl]methyl}-1H-1,2,3-triazol-4-yl)propan-2-amine | 1.1 |
| 51 | ZINC09112445 | 1-(2-methylquinoline-4-carbonyl)-N-phenylpiperidine-3-carboxamide | 1.2 |
| 52 | ZINC20345702 | 2-(4-benzylpiperidin-1-yl)-4-(2-methoxyphenyl)-8-methyl-4H-pyrimido[1,2-a][1,3,5]triazin-6-ol | 0.7 |

TABLE 6

Efficacy and Safety of Compound 26 in hypercholesterolemic mice

| Treatment (genotype) | N | TC (mmol/L) | HDL-C (mmol/L) | TG (mmol/L) | nonHDL-C (mmol/L) | LDL-C (measured) (mmol/L) | LDL-C (pooled plasma) (FPLC AUC) (Fold Change %) | Glucose (mmol/L) | ALT (U/L) | AST (U/L) | ΔBody Weight (D 10 − D 0) (%) |
|---|---|---|---|---|---|---|---|---|---|---|---|
| Placebo (C57BL/6 WT) | 4 | 3.77 ± 0.26 | 3.40 ± 0.30 | 0.92 ± 0.15 | 0.37 ± 0.12 | 0.46 ± 0.13 | — | 15.1 ± 2.2 | 20 ± 3 | 61 ± 2 | 102 ± 4 |
| Cmpd 26 (C57BL/6 WT) | 5 | 3.57 ± 0.26 | 3.33 ± 0.12 | 0.93 ± 0.14 | 0.24 ± 0.13 | 0.36 ± 0.04 | −39% | 14.0 ± 1.2 | 21 ± 5 | 83 ± 21 | 103 ± 2 |
| Placebo (C57BL/6 Pcsk9 KO) | 4 | 3.31 ± 0.32 | 3.18 ± 0.29 | 0.83 ± 0.10 | 0.13 ± 0.11 | 0.28 ± 0.06 | −50% | 15.2 ± 2.1. | 25 ± 10 | 67 ± 14 | 103 ± 5 |
| Cmpd 26 (C57BL/6 Pcsk9 KO) | 4 | 3.03 ± 0.31 | 3.00 ± 0.28 | 0.90 ± 0.08 | 0.04 ± 0.12 | 0.23 ± 0.03 | −61% | 16.3 ± 1.0 | 24 ± 10 | 67 ± 10 | 99 ± 3 |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

The invention claimed is:

1. A method of lowering cholesterol levels in a subject in need thereof, the method comprising administering to the subject a therapeutically effective amount of a compound having the structure of compound 26:

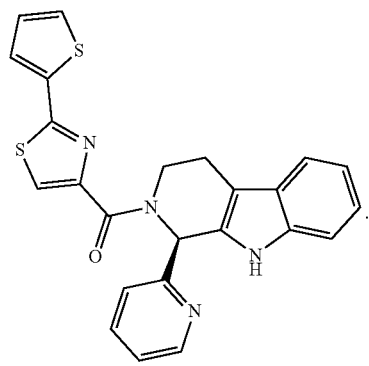 [SMILES: O=C(c1csc(-c2cccs2)n1)N1CCc2c([nH]c3ccccc23)[C@H]1c1ccccn1]

2. A method of binding, modulating PCSK9 activity, and inducing expression of low density lipoprotein receptor (LDLR) in a subject in need thereof, the method comprising administering to the subject a therapeutically effective amount of a compound having the structure of compound 26:

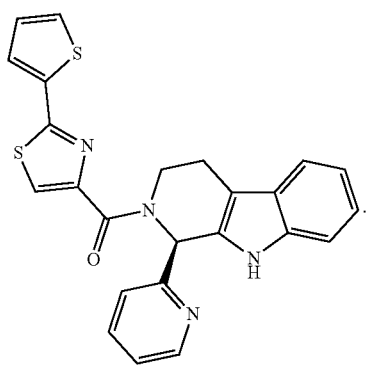 [SMILES: O=C(c1csc(-c2cccs2)n1)N1CCc2c([nH]c3ccccc23)[C@H]1c1ccccn1]

3. The method of claim 2, wherein modulating PCSK9 activity comprises altered subcellular trafficking, decreased PCSK9 binding to LDLR, or decreased PCSK9-induced LDLR degradation.

4. The method of claim 2, wherein the expression is protein expression.

5. A method of treating hypercholesterolemia in a subject in need thereof, the method comprising administering to the subject a therapeutically effective amount of a compound having the structure of compound 26:

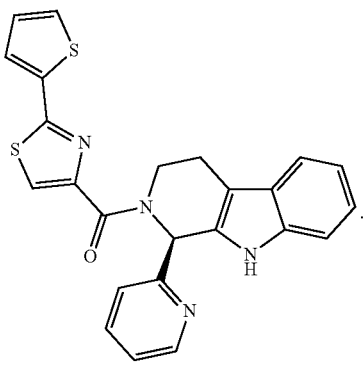 [SMILES: O=C(c1csc(-c2cccs2)n1)N1CCc2c([nH]c3ccccc23)[C@H]1c1ccccn1]

* * * * *